US011103321B2

(12) United States Patent
Braun et al.

(10) Patent No.: US 11,103,321 B2
(45) Date of Patent: Aug. 31, 2021

(54) DEVICE FOR ROBOT-ASSISTED SURGERY

(71) Applicant: avateramedical GmbH, Jena (DE)

(72) Inventors: Marcus Braun, Weil im Schonbuch (DE); Stephan Barber, Stuttgart (DE); Marcel Seeber, Jena (DE)

(73) Assignee: avateramedical GmbH

(*) Notice: Subject to any disclaimer, the term of this patent is extended or adjusted under 35 U.S.C. 154(b) by 489 days.

(21) Appl. No.: 15/527,139

(22) PCT Filed: Nov. 17, 2015

(86) PCT No.: PCT/EP2015/076769
§ 371 (c)(1),
(2) Date: May 16, 2017

(87) PCT Pub. No.: WO2016/083189
PCT Pub. Date: Jun. 2, 2016

(65) Prior Publication Data
US 2017/0348063 A1    Dec. 7, 2017

(30) Foreign Application Priority Data

Nov. 27, 2014   (DE) ...................... 10 2014 117 407.0

(51) Int. Cl.
*A61B 34/35*    (2016.01)
*A61B 46/10*    (2016.01)
(Continued)

(52) U.S. Cl.
CPC .............. *A61B 34/35* (2016.02); *A61B 34/30* (2016.02); *A61B 34/37* (2016.02); *A61B 46/10* (2016.02);
(Continued)

(58) Field of Classification Search
CPC ................ A61B 34/35; A61B 1/00018; A61B 2560/0443; B25J 19/0075
See application file for complete search history.

(56) References Cited

U.S. PATENT DOCUMENTS 5,036,446 A    7/1991  Quintanilla et al.
6,716,215 B1   4/2004  David et al.
(Continued)

FOREIGN PATENT DOCUMENTS

CN    101340852 A    1/2009
CN    101918073 A    12/2010
(Continued)

*Primary Examiner* — Vicky A Johnson
(74) *Attorney, Agent, or Firm* — McGarry Bair PC

(57) ABSTRACT

A device for robot-assisted surgery with at least one coupling unit (100) of a manipulator arm (16) comprising a first transmitting means (102). A sterile cover (38) comprising a sterile lock (200) serves to shield the manipulator arm (16) from a sterile area (39). The sterile lock (200) is connectable both to the coupling unit (100) and to the sterile unit (400). The sterile lock (200) has at least one lock flap (208, 210) which in a closed state shields the first transmitting means (102) in a sterile manner. The sterile unit (400) comprising a second transmitting means (406) has sterile flaps (402, 404) which in a closed state shield the second transmitting means (406) in a sterile manner. When connecting the sterile unit (400) to the sterile lock (200) the lock flap (208, 210) and the sterile flap (402, 404) are opened so that a direct transmission between the first transmitting means (102) and the second transmitting means (406) is possible. When separating the sterile unit (400) from the sterile lock (200) the lock flaps (208, 210) and the sterile flap (402, 404) are each automatically closed and locked so that they shield the first transmitting means (102) and the second transmitting
(Continued)

means (406) from the sterile area (39). Further, the invention relates to a sterile lock (200) and a method for robot-assisted surgery.

19 Claims, 30 Drawing Sheets

(51) Int. Cl.
*A61B 90/00* (2016.01)
*A61B 34/37* (2016.01)
*A61B 34/30* (2016.01)
*B25J 19/00* (2006.01)
*A61B 90/30* (2016.01)
*A61B 1/00* (2006.01)
*A61B 18/12* (2006.01)
*A61B 17/00* (2006.01)

(52) U.S. Cl.
CPC ........... *A61B 90/37* (2016.02); *B25J 19/0075* (2013.01); *A61B 1/00018* (2013.01); *A61B 1/00165* (2013.01); *A61B 18/12* (2013.01); *A61B 2017/00477* (2013.01); *A61B 2034/301* (2016.02); *A61B 2090/306* (2016.02); *A61B 2560/0443* (2013.01)

(56) References Cited

U.S. PATENT DOCUMENTS

| | | | |
|---|---|---|---|
| 7,666,191 | B2 | 2/2010 | Orban, III et al. |
| 8,074,657 | B2 | 12/2011 | Scott et al. |
| 2003/0216723 | A1* | 11/2003 | Shinmura ............... A61B 90/25 606/34 |
| 2004/0049200 | A1 | 3/2004 | Lee et al. |
| 2004/0049205 | A1* | 3/2004 | Lee ......................... A61B 34/71 606/130 |
| 2006/0235436 | A1 | 10/2006 | Anderson et al. |
| 2012/0115007 | A1* | 5/2012 | Felder .................... A61B 46/10 429/121 |
| 2012/0184955 | A1 | 7/2012 | Pivotto et al. |
| 2015/0257842 | A1* | 9/2015 | Dachs, II ............. A61B 90/361 606/130 |
| 2016/0151115 | A1* | 6/2016 | Karguth ............. A61B 1/00149 600/102 |

FOREIGN PATENT DOCUMENTS

| | | |
|---|---|---|
| CN | 102630154 A | 8/2012 |
| CN | 102892376 A | 1/2013 |
| DE | 102006059165 A1 | 8/2007 |
| DE | 102012008535 A1 | 10/2013 |
| WO | 9732534 A1 | 9/1997 |
| WO | 2014/005689 A2 | 6/2013 |

\* cited by examiner

Section A - A

Section B - B

Section C - C

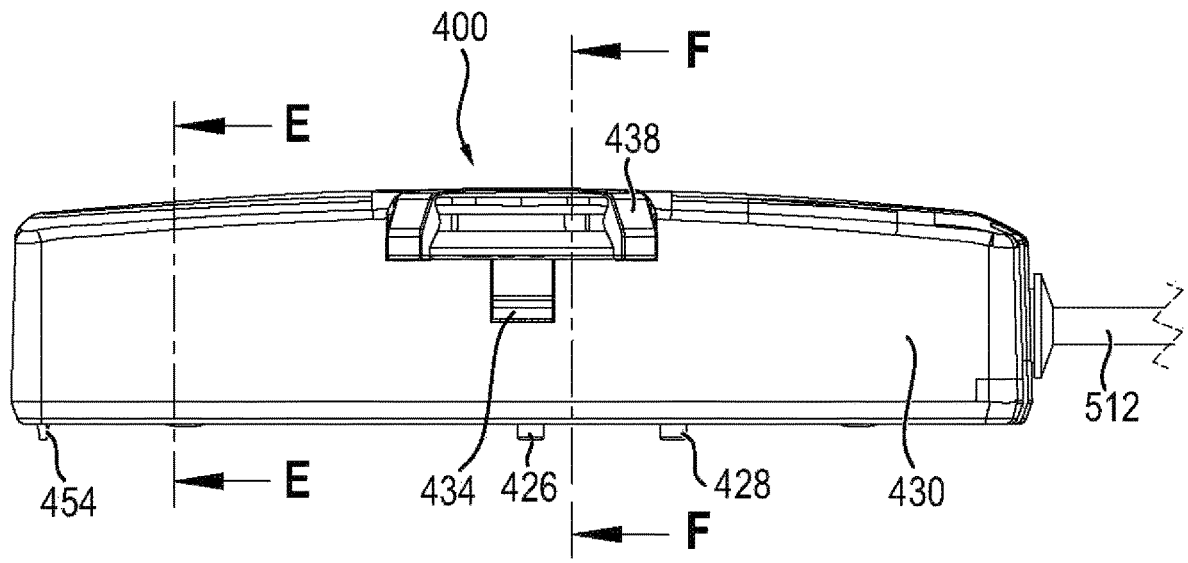
FIG. 17
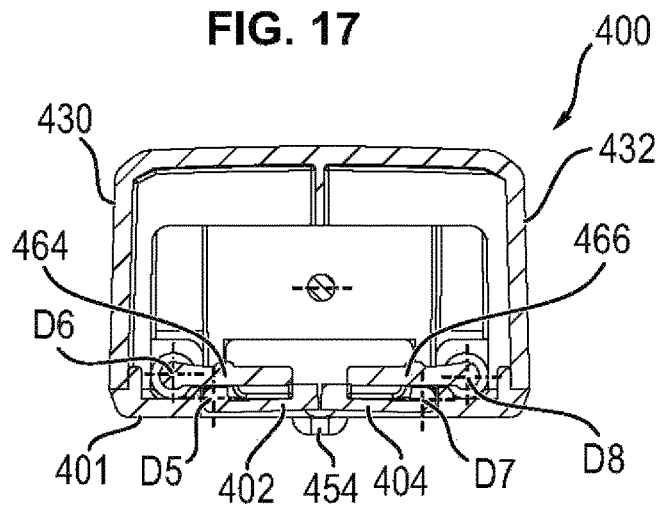
FIG. 18  Section E - E
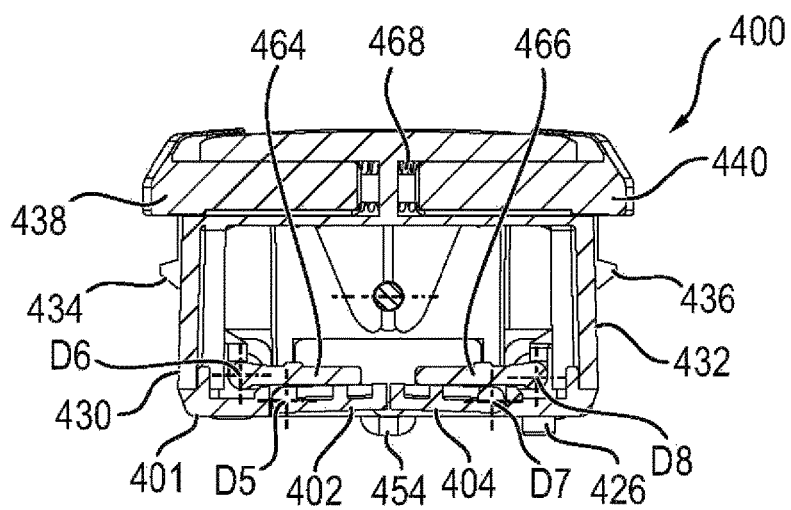
FIG. 19  Section F - F FIG. 23 Section G - G

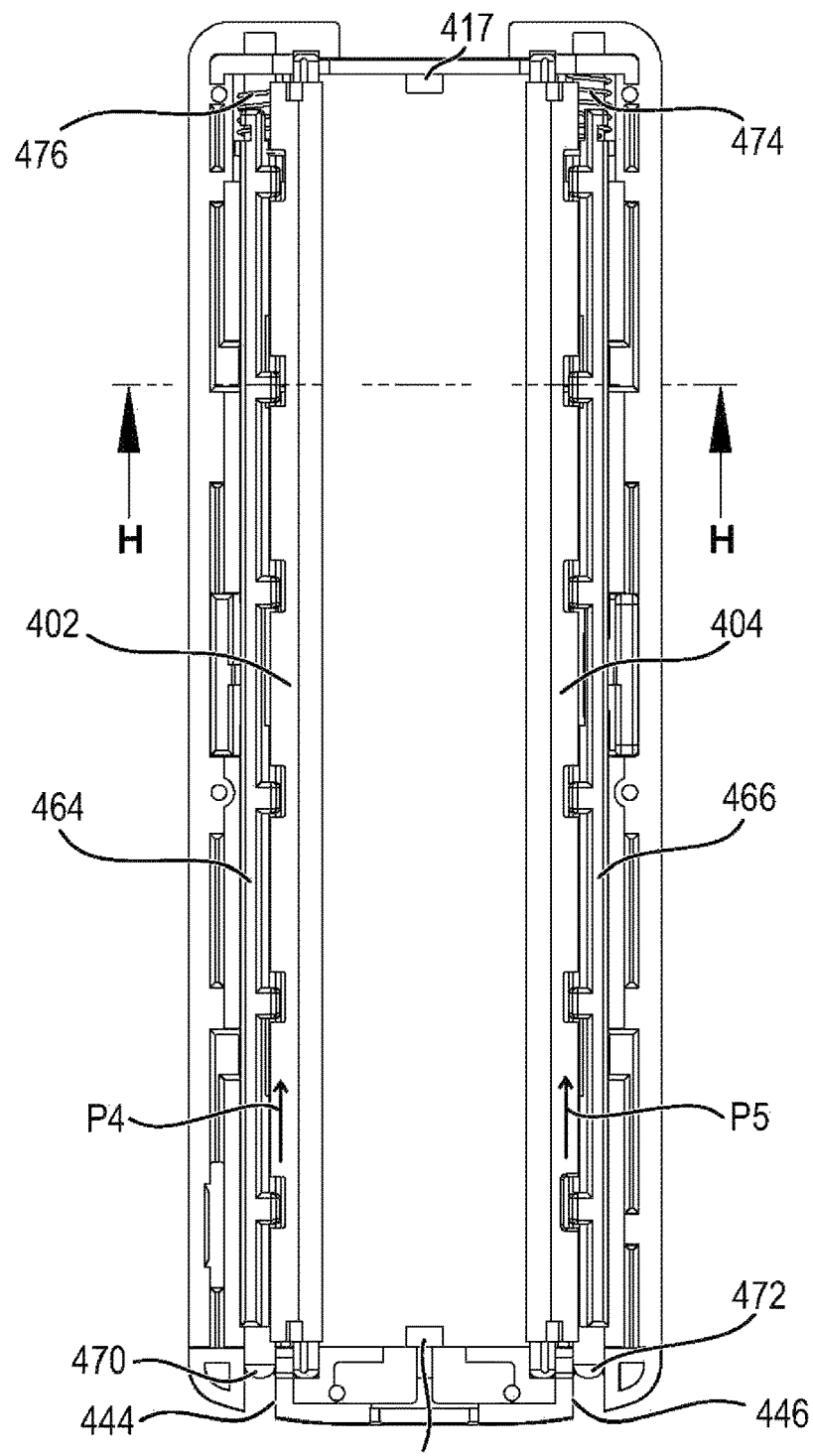
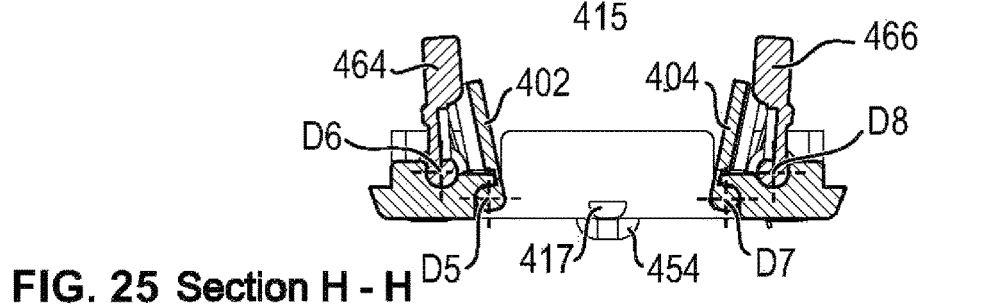
FIG. 24
FIG. 25 Section H - H

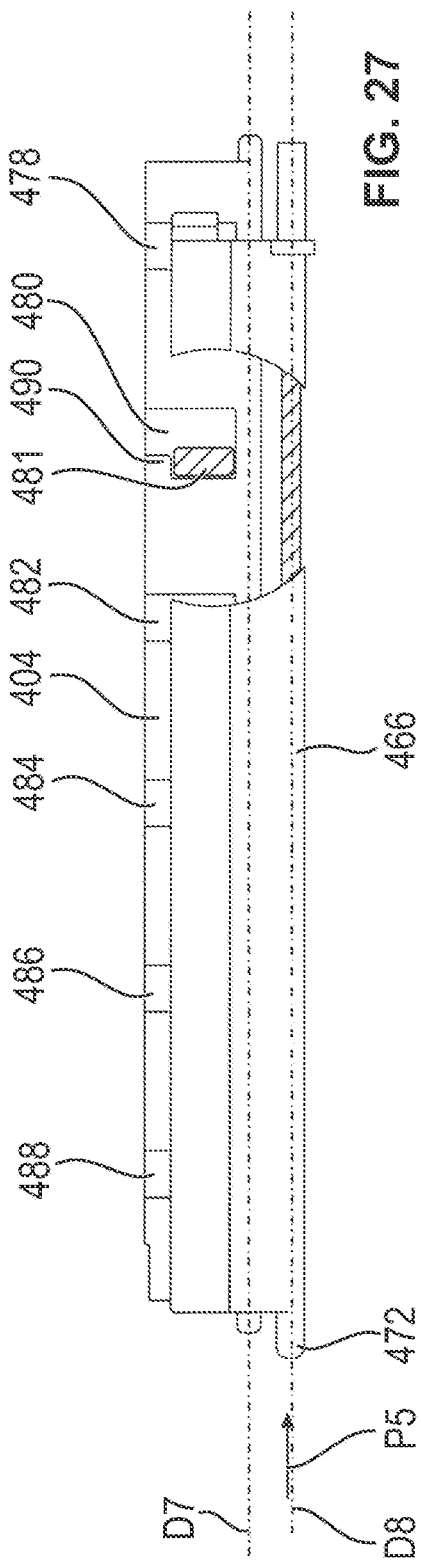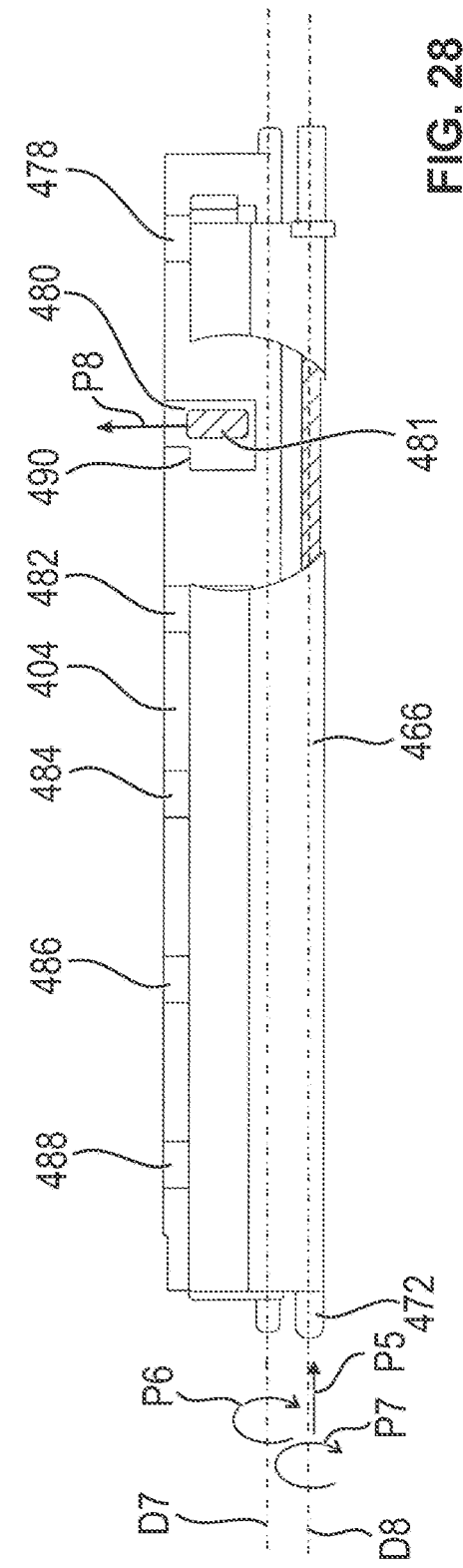

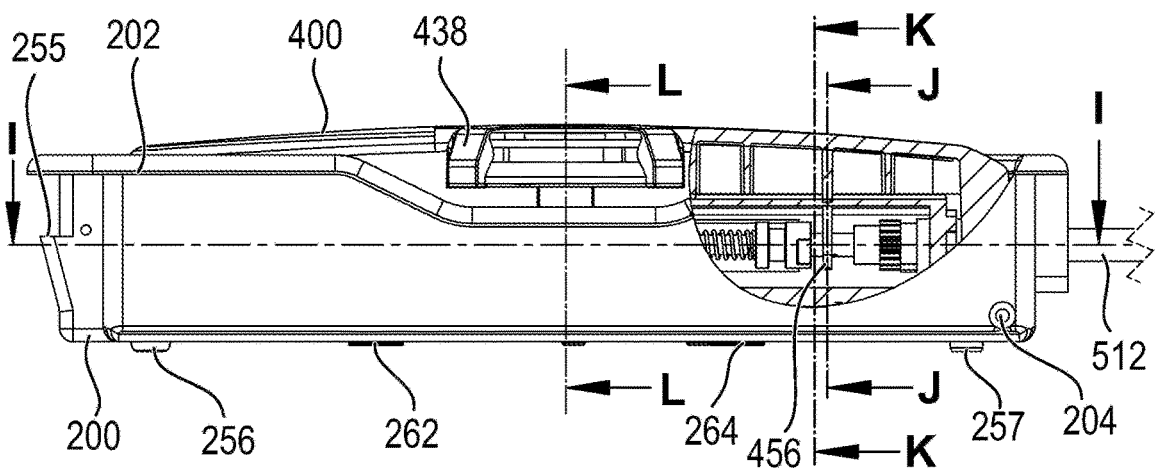
FIG. 30
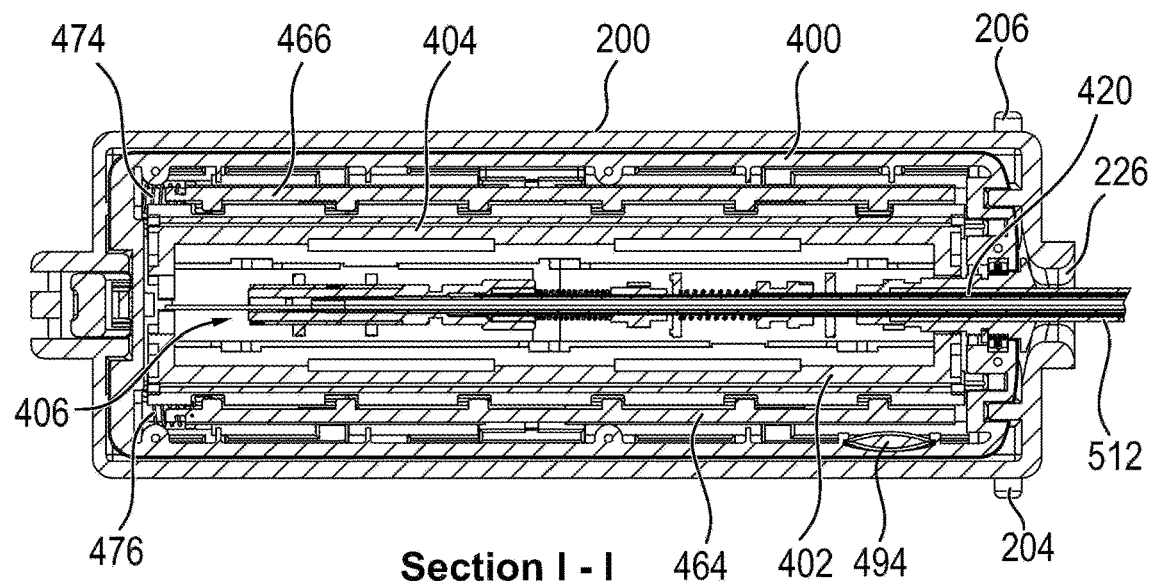
Section I - I
FIG. 31
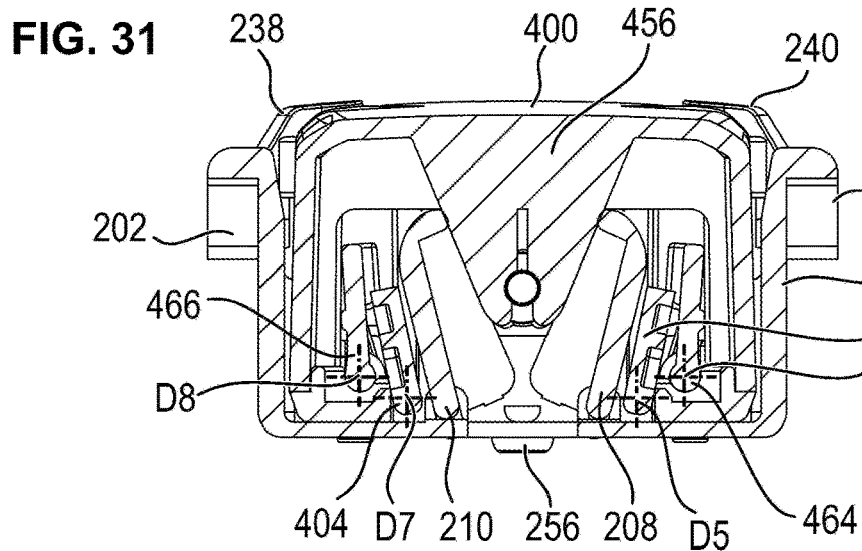
FIG. 32    Section J - J Section K - K Section L - L

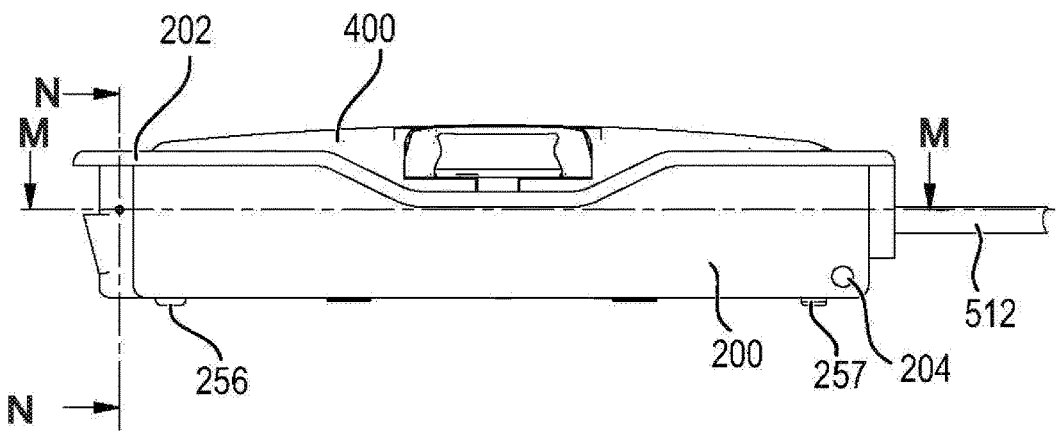
FIG. 36
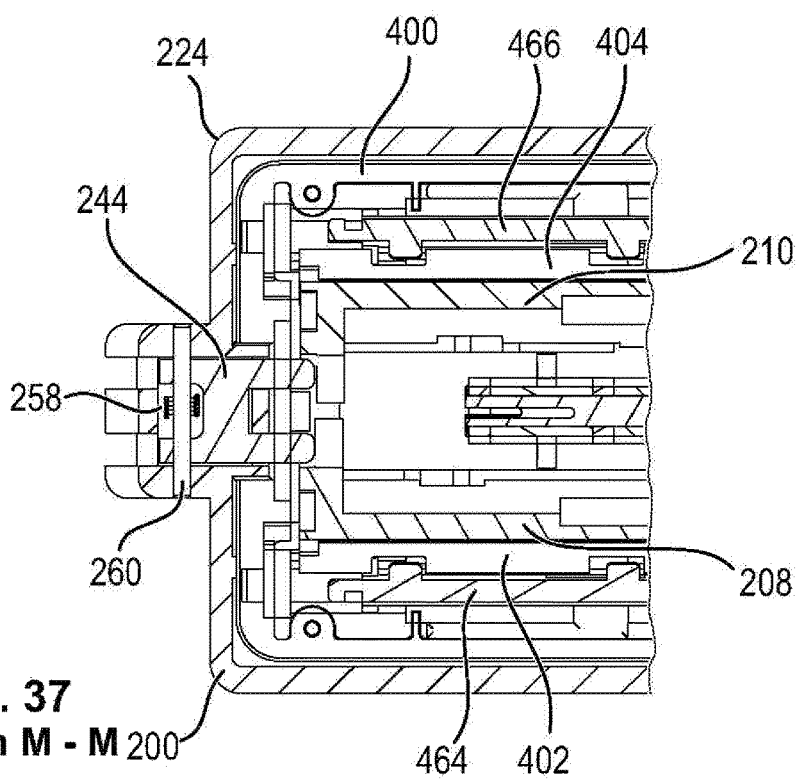
FIG. 37
Section M - M
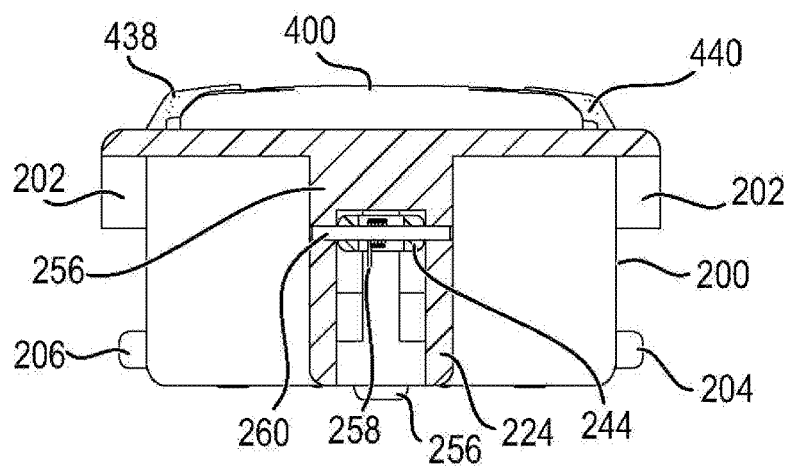
FIG. 38   Section N - N Section O - O Section O - O Section O - O

DEVICE FOR ROBOT-ASSISTED SURGERY

This application is a National Phase application of International Application No. PCT/EP2015/076769, filed Nov. 17, 2015, which claims the benefit of German Patent Application No. 102014117407, filed Nov. 27, 2014, both of which are incorporated herein by reference in their entireties.

The invention relates to a device for robot-assisted surgery, comprising at least one manipulator arm arranged in a non-sterile area and having a coupling unit which has at least a first transmitting means. The device has at least one sterile unit arranged in a sterile area and having at least a second transmitting means and a sterile cover for shielding the manipulator arm from the sterile area. The invention further relates to an arrangement for robot-assisted surgery which comprises such a device for robot-assisted surgery and at least one input device for the input of at least one input command. Further, the invention relates to a sterile lock, in particular for the use in such a device, as well as a method for robot-assisted surgery in which a sterile unit is connectable to a manipulator arm several times in succession.

In minimally-invasive surgery, so-called telemanipulator systems, also referred to as robot-assistance systems, are increasingly used. The sterile surgical field is protected against the non-sterile elements of the telemanipulator system by means of a sterile cover. By means of the sterile cover both a contamination of the sterile surgical field and a contamination of the telemanipulator system by body fluids and/or tissue of the operated patient or of the surgical staff is prevented. This reduces the risk of cross-contamination.

By means of the telemanipulator system surgical instruments and/or endoscopes are controlled in their position and orientation on the basis of user inputs and, in doing so, inevitably come into physical contact with the patient to be operated so that the surgical instruments and/or endoscopes are contaminated with body fluids and/or tissue of the operated patient. At the same time, the surgical instruments have to be coupled mechanically, electrically and/or optically to the telemanipulator system in order to be able to implement an active positioning and orientation of the surgical instrument as well as a desired actuation of a surgical instrument. For this, the surgical instruments, endoscopes or medical devices to be operated have a coupling interface which may be designed as a coupling unit and is also referred to as sterile unit.

The material used during a surgical operation including the employed surgical apparatuses and instruments and the further components of the telemanipulator system can be divided into three categories:

Category 1: The material is sterile and is contaminated during the surgical operation. The material is disposed of after the operation. Thus, there is a one-time use of the material.

Category 2: The material is sterile, is contaminated during the surgical operation and is cleaned and sterilized after the operation. Thus, there is a multiple use of the material. Such materials used multiple times must be designed and produced in accordance with the requirements on a process-capable sterilizability.

Category 3: The material is not sterile. During the surgical operation a contamination of the sterile surgical field is prevented by a sterile cover and over-packaging. At the same time, the non-sterile material is protected against contact with body fluids and/or tissue.

If it is necessary to couple devices of category 1 or category 2 to devices of category 3, then a sterile interface is required which prevents contamination of the devices of category 1 or category 2 by the non-sterile devices of category 3 and, vice versa, prevents a contamination of the devices of category 3 since these are generally technically designed as autoclavable components that cannot be sterilized. The realization of devices as autoclavable components that can be sterilized requires a particular technical design of the device for the sterilization process so that a higher development effort as well as considerable validation effort for proving the effectiveness of the sterilization process are necessary for this. For such a proof, it is in particular necessary, multiple times in succession, to contaminate and sterilize the device and to perform an effectiveness check of the sterilization as well as a functionality check after sterilization. Here, proof has to be furnished that after each sterilization the devices are reliably sterilized and thus could be used again.

From document U.S. Pat. No. 7,666,191 B1, a telemanipulator system is known in which the non-sterile manipulator arms are covered by means of a sterile drape. The coupling unit of the manipulator arm comprises four rotation actuators which are coupled to a first side of a sterile adaptor integrated in the sterile drape. By means of the sterile adaptor, the rotary motions of the four rotation actuators of the coupling unit of the manipulator arm are engaged with four rotatably mounted transmitting means integrated in the sterile adaptor. On the sterile outside surface of the sterile adaptor these sterile transmitting means on the outside surface of the sterile adaptor can be engaged with driven elements of the sterile surgical instrument. Further, via this sterile adaptor electrical signals can be transmitted between the inside and the outside of the sterile adaptor.

Thus, by means of the sterile adaptor it is prevented that the rotation actuators and the electrical connections of the sterile surgical instrument come into direct contact with the rotation actuators and the electrical connections of the coupling unit of the non-sterile manipulator arm. A contamination of the surgical instrument by the contact with non-sterile parts of the manipulator arm is prevented by the sterile adaptor. In this solution it is, however, essential that the sterile adaptor must have rotatably mounted transmitting means as well as transmitting means for transmitting electrical signals, as a result whereof the adaptor is costly in production and is susceptible to interference. In particular, it is costly to guarantee the rotatability of the transmitting means when the transmitting means come into contact with body fluid.

Basically, each element in the chain of functions for coupling the manipulator arm and the instrument is a possible source of errors and involves additional costs. The sterile adapter itself is provided as part of the sterile drape for a one-time use.

From document U.S. Pat. No. 8,074,657 B2, a further sterile adapter is known which comprises an actuator unit for transmitting mechanical energy to a surgical instrument coupled to the sterile adapter.

It is the object of the present invention to specify a device and a method for robot-assisted surgery, in which a sterile coupling of a manipulator arm arranged in a non-sterile area to a sterile unit arranged in a sterile area is easily possible. Further, an arrangement for robot-assisted surgery within a sterile area as well as a sterile lock for coupling a coupling unit of an manipulator arm to a sterile unit are to be specified.

This object is solved by a device for robot-assisted surgery having the features of claim 1 and by an arrangement, by a sterile lock and by a method having the features of the respective independent claim. Advantageous developments of the invention are specified in the dependent claims.

In the invention, in particular by providing a sterile lock which is connectable both to a coupling unit and to a sterile unit, the lock flap is opened, preferably automatically mechanically, when connecting the sterile unit to the sterile lock so that the first transmitting means of the coupling unit and the second transmitting means of the sterile unit are arranged opposite to each other without a further transmitting element being arranged between them. The transmitting means can directly contact each other, or there is a transmission via an air gap between the first transmitting means and the second transmitting means. As a result, when connecting the sterile unit to the sterile lock, the first transmitting means covered by the lock flap in a sterile manner is uncovered for a transmission with the second transmitting means. When separating the sterile unit from the sterile lock, at least the first transmitting means is again shielded in a sterile manner. Preferably, the sterile lock is already connected to the coupling unit when connecting and separating the sterile unit to or from the sterile lock, respectively. Preferably, the sterile lock remains connected to the coupling unit throughout the entire period of time of the surgical operation, wherein the sterile unit can be separated from and re-connected to the coupling unit of the manipulator arm multiple times or can be replaced by a further sterile unit. Further, it is possible to connect the sterile lock to the coupling unit and the sterile unit such that the first transmitting means is directly connected to the second transmitting means, preferably directly engaged therewith.

By means of the invention it is in particular possible to provide the sterile lock without mechanical and/or electrical transmitting means so that both a reliable sterile shielding of the non-sterile manipulator arm and the non-sterile coupling unit as well as a reliable coupling of the first transmitting means to the second transmitting means without any interconnection of further transmitting means, in particular without interconnecting further mechanical transmitting means is possible. The sterile cover in particular comprises a sterile flexible material, such as a sterile foil, and the at least one sterile lock.

It is advantageous when the sterile unit has at least one sterile flap which in a closed state shields the second transmitting means in a sterile manner. When connecting the sterile unit to the sterile lock then each time a movement of the lock flap and the sterile flap from the closed state into the open state takes place so that a direct transmission between the first transmitting means and the second transmitting means through an opening uncovered by the lock flap and the sterile flap in the open state is possible. When separating the sterile unit from the sterile lock, a movement of the lock flap and the sterile flap each time from the open state into the closed state takes place so that after separation the lock flap shields the first transmitting means from the sterile area and the sterile flap shields the second transmitting means from the sterile area.

Preferably, the first transmitting means of the coupling unit comprises at least one drive element and/or at least a first electrical interface and/or at least a first optical interface. The second transmitting means of the sterile unit comprises at least a driven element and/or a second electrical interface and/or at least a second optical interface. The sterile lock is connectable to the coupling unit and the sterile unit such that the at least one drive element is mechanically directly engaged with the at least one driven element. As a result, torques can easily and safely be transmitted between the coupling unit and the sterile unit. If the sterile unit forms part of a surgical instrument unit, by means of the torques transmitted from the coupling unit to the sterile unit the surgical instrument of the instrument unit can be moved and/or actuated in that at least a torque is transmitted from the drive element to the driven element. Alternatively or additionally, the first electrical interface can be coupled to the second electrical interface and/or the first optical interface can be coupled to the second optical interface.

According to the definition in the introductory part of the description, the sterile unit is material of category 1 and 2 and is thus sterile.

Further, it is advantageous when the coupling unit is connectable to a first connecting area of the sterile lock and when the sterile unit is connectable to a second connecting area of the sterile lock. The first connecting area and the second connecting area are preferably arranged on sides of the sterile lock facing away from each other. As a result, an easy coupling and thus an easy handling both of the sterile cover and of the sterile unit before, during and after the surgical operation is possible. Further, it is particularly advantageous when the second connecting area is designed as a receiving area in which the sterile unit is receivable at least in part when it is connected to the second connecting area. As a result, an easy and reliable connection between the sterile unit and the sterile lock can be established. In particular, the sterile unit can at least in part be pressed into the receiving area and be locked therein.

Further, it is advantageous when the sterile lock has a third connecting area with which the flexible cover is connectable, wherein the third connecting area is arranged preferably circumferentially around the sterile lock, in particular on the circumferential surface, preferably between the first and second connecting area. By means of the sterile lock an easy connection of the sterile area and the non-sterile area for coupling the coupling unit to the sterile unit is established, without the sterile unit being contaminated such that it can no longer remain in the sterile area after a separation from the sterile lock.

Preferably, the coupling unit is arranged at the proximal end of the manipulator arm. Alternatively or additionally, the sterile unit forms part of a surgical instrument, an endoscope and/or a medical device, wherein the sterile unit is arranged in particular at the distal end of the surgical instrument, the endoscope and/or the medical device. As a result, the sterile lock can be used for various instruments and devices required during a surgery on a patient without different sterile locks or sterile locks with different modes of action have to be used.

Further, it is advantageous when the first connecting area of the sterile lock is connectable to the coupling unit via a first releasable snap-in connection and the second connecting area of the sterile lock is connectable to the sterile unit via a second releasable snap-in connection. As a result, the sterile lock is reliably connectable to both the coupling unit and the sterile unit and is easily separable from these again so that an easy handling both of the sterile cover with the sterile lock and of the sterile unit, in particular during a surgical operation, is possible.

It is particularly advantageous when the coupling unit comprises at least one coupling sensor which detects the presence of a sterile unit that is correctly connected to the sterile lock. Further, the device has a control unit which only allows a transmission between the first transmitting means and the second transmitting means when a sterile unit that is correctly connected to the sterile lock has been detected by means of the coupling sensor. In a further advantageous embodiment the coupling sensor detects by means of a detection element which is provided on the sterile unit and which, when connected to the sterile lock, projects up into the first connecting area with which the coupling unit is connected, that both the sterile unit is correctly connected to the second connecting area and the coupling unit is correctly connected to the first connecting area. The control unit preferably only enables or only permits a transmission between the first transmitting means and the second transmitting means when the coupling sensor has detected a correct connection between the sterile unit and the second connecting area and the coupling unit and the first connecting area.

In addition, by means of the coupling sensor it can easily be detected whether at least the sterile unit is correctly connected to the sterile lock so that then it can be assumed that the sterile unit is correctly connected to the sterile lock and, via the sterile lock, is correctly connected to the coupling unit of the manipulator arm. As a result, a safe transmission between the first transmitting means and the second transmitting means is possible.

Further, it is advantageous when the coupling unit has several drive elements as a first transmitting means and when the sterile unit has several driven elements as a second transmitting means. The drive elements are then directly mechanically engaged with the driven elements for a mechanical coupling of the coupling unit with the sterile unit when connecting the sterile unit with the sterile lock given a connection of the coupling unit to the sterile lock. Alternatively or additionally, the coupling unit has at least two first electrical contact elements as a first transmitting means and the sterile unit has two second electrical contact elements which are complementary to the first electrical contact elements as a second transmitting means. The first contact elements and the second contact elements establish a direct electrical connection between the coupling unit and the sterile unit when the coupling unit is connected to the sterile lock and when the sterile unit is connected to the sterile lock. This electrical connection can in particular be used for transmitting high-frequency electrical energy, in particular for high-frequency surgery. Thus, the sterile unit can form part of a surgical high-frequency instrument. If several drive elements and several driven elements are provided, different movements and/or actuations of a surgical instrument coupled to the coupling unit via the sterile unit are easily possible.

It is particularly advantageous when the lock flap separates the first connecting area from the second connecting area and when the lock flap automatically opens when the sterile unit is connected to the second connecting area. When separating the sterile unit from the second connecting area, the lock flap automatically closes. As a result, an easy and safe covering of the non-sterile elements of the coupling unit is possible so that contaminations of the sterile area by non-sterile elements of the coupling unit are easily prevented. Here, it is advantageous when the lock flap is automatically unlocked when connecting the sterile unit to the second connecting area and when the lock flap is automatically locked when separating the sterile unit from the second connecting area. As a result, a safe covering of the non-sterile elements of the coupling unit is guaranteed. An inadvertent opening of the lock flap, such as by contact, is effectively prevented easily.

Further, it is advantageous when the sterile flap of the sterile unit covers the at least one second transmitting means and when the sterile flap opens automatically when connecting the sterile unit to the second connecting area, and when the sterile flap automatically closes when separating the sterile unit from the second connecting area. As a result, also the possibly contaminated second transmitting means is safely shielded in a sterile manner when the sterile unit has again been separated from the sterile lock.

Further, it is advantageous when the sterile flap is automatically unlocked when connecting the sterile unit to the second connecting area and when the sterile flap is automatically locked when separating the sterile unit from the second connecting area. By way of the automatic locking and unlocking an inadvertent contact with the second transmitting means of the sterile unit contaminated by a possible contact between the first transmitting means and the second transmitting means is easily prevented in that the second transmitting means are shielded by means of the sterile flap and the latter is safely locked so that an inadvertent contact with the second transmitting means after the separation of the sterile unit from the sterile lock is not possible.

Further, it is advantageous when the sterile outside of the sterile flap is arranged opposite to the sterile outside of the lock flap facing the second connecting area when connecting the sterile unit to the second connecting area, when both the sterile flap and the lock flap are open. It is particularly advantageous when the sterile outsides of the sterile flap and the lock flap face each other in the open state, preferably contact each other. By the facing arrangement of the sterile outside of the lock flap and the sterile outside of the sterile flap a contamination of the outside of the respective other flap is not possible since only the insides can be contaminated by a contact with at least one non-sterile transmitting element.

It is particularly advantageous when the sterile unit forms part of a surgical instrument, the sterile unit in particular being arranged at the distal end of the surgical instrument.

It is particularly advantageous when the sterile cover and/or the sterile lock are made of polyethylene, polyurethane and/or polycarbonate. As a result, both an easy manufacturing of the cover or the sterile lock and an easy and safe handling of the cover and the sterile lock are possible.

The surgical instrument preferably comprises at least one end effector insertable into an orifice of the body of a patient, such as a clamp, a pair of scissors, a grasper, a needle holder, a micro dissector, a clamping device, a staple applier, a rinsing and/or an aspiration device, a cutting blade, a cauterization probe, a catheter and/or a suction nozzle. As a result, the surgical instrument can optionally have different end effectors which can be used for common minimally-invasive surgeries, in particular in laparoscopic surgery. However, also other surgical instruments can be used additionally or alternatively. In particular, the surgical instrument can also be an optical surgical instrument, such as an endoscope, which then has further optical and electrical transmitting means or interfaces, such as electrical contacts for camera control or for image data transmission, optical fiber connections, in particular for illumination.

A second aspect of the invention relates to an arrangement for robot-assisted surgery, in particular to a telerobot-assisted procedure within a sterile field by means of a sterile surgical instrument. This arrangement comprises at least one device according to claim 1 or according to an aforementioned development; a display unit which outputs in real time at least one image of the field of operation in which the end effector of the surgical instrument can be, preferably as an image sequence, and at least one device for the input of at least one input command. The arrangement further has a control unit which positions the manipulator arm and the sterile unit connected via the sterile lock to the coupling unit of the manipulator arm dependent on the input command by means of at least one drive unit. As a result, an easy control of the manipulator arm for positioning the sterile unit and/or an actuation for actuating the sterile unit is easily possible. Preferably, the input device has an actuating element actuatable by a user, such as a surgeon, wherein the input device detects a change of position in space of the actuating element and generates an input command corresponding to the detected change of position in space. Dependent on the input command the control unit generates at least one control command by which the same or a scaled down change of position in space of at least an end of the sterile unit and/or of the surgical instrument, at the distal end of which the sterile unit is arranged, is caused and/or by which an actuation or a reduced actuation of the surgical instrument, at the distal end of which the sterile unit is arranged, is caused. As a result, an easy positioning and/or actuation of the surgical instrument by an operator who is remote from the patient in the operating room or outside the operating room is easily possible. As an output of an image in real time the immediate output of an image detected by means of an image detection unit preferably as a video sequence without delays going beyond the delays occurring during image processing.

Further, it is advantageous when the arrangement has several devices for robot-assisted surgery according to claim 1 or according to a mentioned development. The input device has preferably at least two actuating elements actuatable by a user, wherein the input device detects a change of position in space of each actuating element and generates each time an input command corresponding to the detected change of position in space. Dependent on each input command, the control unit generates at least one control command each by which the same or a scaled up/down change of position in space of at least one end of a surgical instrument, at the distal end of which the sterile unit is arranged, of the device for robot-assisted surgery assigned to the respective actuating element at the point in time of the actuation is caused and/or by which an actuation or a scaled actuation of this surgical instrument is caused. As a result, the operation can be performed with several instruments which are present in the operating field at the same time or which, in the case of laparoscopic surgeries, are present in the abdominal cavity of the patient at the same time.

A third aspect of the invention relates to a sterile lock which is in particular suitable for use in a device for robot-assisted surgery according to claim 1 or a development of this device. The sterile lock has a first connecting area for connecting the sterile unit to a non-sterile coupling unit and a second connecting area for connecting the sterile lock to a sterile unit arranged in a sterile area. The sterile lock further has a circumferential third connecting area for connecting the sterile lock to a flexible sterile cover for separating the sterile area from the non-sterile area. Further, the sterile lock has at least one lock flap which in a closed state closes an opening between the first connecting area and the second connecting area in a sterile manner and in an open state uncovers the opening between the first connecting area and the second connecting area. By way of such a sterile lock, an easy handling of the sterile unit when connecting the latter to the coupling unit is made possible, wherein both the non-sterile transmitting means of the coupling unit are shielded in a sterile manner and a direct coupling of a first transmitting means arranged in the coupling unit to a second transmitting means arranged in the sterile unit is easily possible. In particular, drive elements of the coupling unit and driven elements of the sterile unit can be directly engaged when the lock flap is open.

It is particularly advantageous when the sterile lock is connectable to the sterile unit and to the coupling unit such that at least a drive element of the coupling unit serving as a first transmitting element is mechanically directly engaged with at least one drive element of the sterile unit serving as a second transmitting means. By the direct mechanical engagement, torques can be transmitted from the drive element to the driven element so that a transmission of torques between the non-sterile area and the sterile area through the sterile lock is easily possible without interconnecting further transmitting means. Thus, additional transmitting means for connecting the drive elements and the driven elements are not necessary. Such transmitting means are both susceptible to failure and can only be integrated in a sterile cover in a relatively complex manner.

It is particularly advantageous when the third connecting area of the sterile lock is arranged at an outside of the sterile lock between the first connecting area and the second connecting area. In particular, the third connecting area is arranged circumferentially on a circumferential surface of the sterile lock. The connection between the sterile lock and a sterile flexible covering material can be established via a clamping, Velcro, welding and/or adhesive connection. As a result, the sterile flexible cover material can easily be connected to the outside of the sterile lock so that the cover material together with the sterile lock forms a continuous sterile cover.

For forming a clamping connection, the third connecting area can be designed as a clamping area so that the flexible cover material can be connected to the clamping elements of the third connecting area. Alternatively or additionally, the third connecting area can be formed as an adhesive area by which the sterile flexible covering material is connectable to the third connecting area by means of adhesive. Alternatively or additionally, the sterile flexible covering material can be connected to the third connecting area via a welding connection.

Further, it is advantageous when the lock flap automatically opens when connecting the sterile unit to the first connecting area and when the sterile lock automatically closes again when separating the sterile unit from the first connecting area. The opening and closing of the lock flap preferably takes place mechanically, wherein the lock flap is opened against spring force and can be closed by spring force. Preferably, the lock flap is locked in the closed state so that it cannot be opened by a force on the closed lock flap. As a result, an easy and safe handling of the sterile lock is possible. In particular, non-sterile areas of the coupling unit are covered by means of the lock flap when the sterile unit is not connected to the sterile lock.

A fourth aspect of the invention relates to a method for robot-assisted surgery, in particular by using a device according to claim 1 or an above-described development, an arrangement according to the second aspect of the invention or a development of this arrangement or by using a sterile lock according to the third aspect of the invention or a specified development of this sterile lock. In the method, a manipulator arm arranged in the non-sterile area is shielded from the sterile area by means of a sterile cover and a sterile lock integrated in the cover. A non-sterile coupling unit of the manipulator arm is connected to a first connecting area of the sterile lock. An opening between the first connecting area and a second connecting area of the sterile lock is closed by means of a sterile flap. The lock flap is automatically opened when connecting a sterile unit arranged in a sterile area to the second connecting area of the sterile lock so that a direct transmission between the first transmitting means and the second transmitting means of the sterile unit is possible in case of an open lock flap. By opening the lock flap, the opening between the first connecting area and the second connecting area is open.

The lock flap is automatically closed when separating the sterile unit from the second connecting area, as a result whereof the opening between the first connecting area and the second connecting area is again closed in a sterile manner. The lock flap is again automatically opened when connecting the sterile unit arranged in the sterile area or a further sterile unit arranged in the sterile area to the second connecting area of the sterile lock so that a direct transmission between the first transmitting means and the second transmitting means or a further second transmitting means of the further sterile unit is again possible. As a result, an easy coupling between the coupling unit and the sterile unit is possible, wherein the sterile unit, if necessary, can be separated from the sterile lock several times without contaminating the sterile area. This is guaranteed even when the second transmitting means has been contaminated, in particular by a contact with the first transmitting means.

In particular when the sterile unit is used only once, it does not have to have a sterile flap. The sterile unit is then immediately removed from the sterile area after separation from the sterile lock during a surgery.

However, it is advantageous when the sterile unit has at least one sterile flap which in a closed state shields the second transmitting means in a sterile manner. The lock flap and the sterile flap are each moved from the closed state into the open state when connecting the sterile unit to the sterile lock so that a direct transmission between the first transmitting means and the second transmitting means through an opening uncovered by the sterile flap and the lock flap in the open state is possible. When separating the sterile unit from the sterile lock, the lock flap and the sterile flap are each moved from the open state into the closed state so that after separation the first transmitting means is shielded from the sterile area by means of the lock flap and the second transmitting means is shielded from the sterile area by means of the sterile flap.

Here, it is advantageous when the opening of the sterile unit is closed by the sterile flap in its closed state such that the second transmitting means is arranged behind the sterile flap and when the sterile flap upon connection to the sterile lock is opened such that an access to the second transmitting means is possible. Preferably, the sterile flap is automatically opened when connecting the sterile unit to the second connecting area of the sterile lock. When separating the sterile unit from the second connecting area of the sterile lock, the sterile flap is automatically closed. As a result, a safe handling of the sterile unit and of the sterile lock together with a non-sterile coupling unit is possible.

Further, it is advantageous when the first transmitting means comprises at least one drive element and when the second transmitting means comprises at least one driven element. During connection of the sterile unit to the second connecting area of the sterile lock, the lock flap of the sterile lock and a sterile flap of the sterile unit are opened such that during connection of the sterile unit to the second connecting area the drive element is directly engaged with the driven element. In particular, this takes place without interconnecting further transmitting means, in particular without interconnecting a moved transmitting means so that a contamination of at least the outside of the sterile unit is safely prevented, as a result whereof the sterile unit, even after separation from the sterile lock, can simply remain in the sterile area and can be placed thereat.

Here, it is not a disadvantage when the sterile driven element is contaminated upon first contact with the drive element because the contaminated driven element is shielded by the sterile flap in a sterile manner while separating the sterile unit from the second connecting area. Preferably, when separating the sterile unit from the first connecting area both the lock flap and the sterile flap are closed and preferably locked such that each time an access area to the drive element and to the driven element are shielded in a sterile manner. Preferably, the sterile flap and the lock flap are mechanically locked in the closed state so that neither the lock flap nor the sterile flap can be opened manually. As a result, a sterile covering of non-sterile or contaminated elements of the coupling unit and of the sterile unit is guaranteed so that the sterile area is not contaminated even after separating the sterile unit from the sterile lock.

Altogether, an inventive method enables an easy and safe handling, in particular an easy and safe exchange of the sterile unit, in particular of an instrument unit comprising the sterile unit with a surgical instrument during a surgical intervention.

In all embodiments and developments, the sterile lock can have two lock flaps and the sterile unit can have two sterile flaps.

In all described embodiments, the sterile lock forms no part of the chain of functions for the transmission of electrical energy, of electrical or optical signals and/or mechanical energy between the manipulator arm and the sterile unit. Rather, the sterile lock can comprise a fixed form part and a lock flap system comprising at least the lock flap, which shields the non-sterile first transmitting means of the coupling unit such that this one and the entire coupling unit are covered in a sterile manner relative to the sterile surrounding after mounting the sterile cover with the sterile lock. The opening mechanism of the lock flap system is preferably designed such construction-wise that it cannot be opened from outside by inadvertent actuation. Further, also the second transmitting means are shielded by a sterile housing of the sterile unit and by the at least one sterile flap of the sterile unit in a sterile manner. These second transmitting means in particular comprise at least one driven element, preferably at least one driven element for taking up rotatory operating forces and a driven element for taking up translatory operating forces are provided.

In addition, at least one electrical connection for transmitting high-frequency energy for high-frequency surgery can be provided. It is particularly advantageous when the sterile unit has at least two driven elements for taking up rotatory operating forces and two driven elements for taking up translatory operating forces. The coupling unit of the manipulator arm then has two drive units as first transmitting means for generating rotatory operating forces, each of which being directly engaged with the complementary driven elements serving as second transmitting means for taking up the rotatory operating forces of the sterile unit. Further, the coupling unit has as a first transmitting means two drive elements for generating translatory operating forces which drive elements are directly engaged with driven elements serving as a second transmitting means for taking up translatory operating forces. A surgical instrument comprising the sterile unit is in particular a laparoscopic instrument.

Preferably, opening mechanisms of the sterile flap system and/or of the lock flap system are designed such construction-wise that they cannot be triggered from outside by inadvertent actuations but only in the case of a correct coupling of the sterile unit to the sterile lock. The opening mechanism of the sterile flap system and of the lock flap system are preferably designed such construction-wise that when connecting the sterile unit to the sterile lock the flaps of the lock flap system and of the sterile flap system are automatically unlocked and opened by corresponding engaging elements. In this way, the drive elements serving as transmitting means and the driven elements as well as electrical contact elements can be directly engaged or brought into contact with one another. Thus, a direct connection between the non-sterile drive elements of the coupling unit and the driven elements of the sterile unit of a surgical instrument can be established. As a result, the previously sterile driven elements of the sterile unit may be contaminated.

When the sterile unit is again separated from the sterile lock, both the lock flaps of the lock flap system of the sterile lock and the sterile flap of the sterile flap system of the sterile unit are again closed, in particular before the sterile unit has been completely removed from the sterile lock. Thus, it is guaranteed that at no point in time both the non-sterile parts of the coupling unit and the no longer sterile driven elements of the sterile unit and/or the electrical contacts of the sterile unit can come into contact with the sterile surgical field and the patient environment and could contaminate the same. As a result, the sterile unit with the closed sterile flap system can be directly placed in the sterile patient environment and thus be kept ready until a re-use, i.e. up to a re-connection to the first connecting area of the sterile lock without a contamination of the sterile patient environment.

The drive elements serving as first transmitting means and the driven elements serving as second transmitting means are preferably designed such that a laparoscopic surgical instrument can be moved in altogether four degrees of freedom, namely:
1. Rotation of the instrument shaft
2. Rotation of the instrument tip independent of the instrument shaft
3. Bending of the instrument tip relative to the instrument shaft
4. Actuation of the surgical instrument, in particular for generating a relative movement of two elements arranged movably to each other, such as the grasping motion of the instrument tip or of blades of scissors.

During the connection to the sterile lock, the sterile housing of the sterile unit is preferably pressed into a receiving area of the second connecting area and secured by means of a mechanical detent on the sterile lock against inadvertent removal. The mechanical detent thus creates a snap-in connection between the sterile lock and the sterile unit. For separating the sterile unit from the sterile lock an unlocking button is actuated manually so that the sterile unit is separated from the second connecting area, preferably can be removed from the receiving area of the second connecting area.

In general, an end of an arbitrary element facing the patient is considered as proximal. In general, an end of an element facing away from the patient is considered as distal.

Further features and advantages result from the following description which explains the invention in more detail on the basis of embodiments in connection with the enclosed Figures.

FIG. 17 shows a side view of the instrument unit.

FIG. 18 shows a sectional illustration of the instrument unit according to FIG. 17 along the sectional line E-E.

FIG. 19 shows a sectional illustration of the instrument unit according to FIG. 17 along the sectional line F-F.

FIG. 23 shows a sectional illustration of the sterile flap system according to FIG. 22 along the sectional line G-G.

FIG. 24 shows a top view of the sterile flap system according to FIGS. 22 and 23 with open sterile flaps.

FIG. 25 shows a sectional illustration of the sterile flap system according to FIG. 24 along the sectional line H-H.

FIG. 27 shows a top view of the guiding flap and the sterile flap according to FIG. 26 in a locked state.

FIG. 28 shows a top view of the sterile flap and the guiding flap in an unlocked state.

FIG. 30 shows a partial sectional illustration of an arrangement with the sterile unit and the sterile lock in a connected state.

FIG. 31 shows a sectional illustration of the arrangement according to FIG. 30 along the sectional line I-I.

FIG. 32 shows a sectional illustration of the arrangement according to FIG. 30 along the sectional line J-J.

FIG. 36 shows a side view of the arrangement according to FIGS. 30 to 35.

FIG. 37 shows a sectional illustration of the part of the arrangement according to FIG. 36 along the sectional line M-M.

FIG. 38 shows a sectional illustration of the arrangement according to FIG. 36 along the sectional line N-N.

Figure 1:
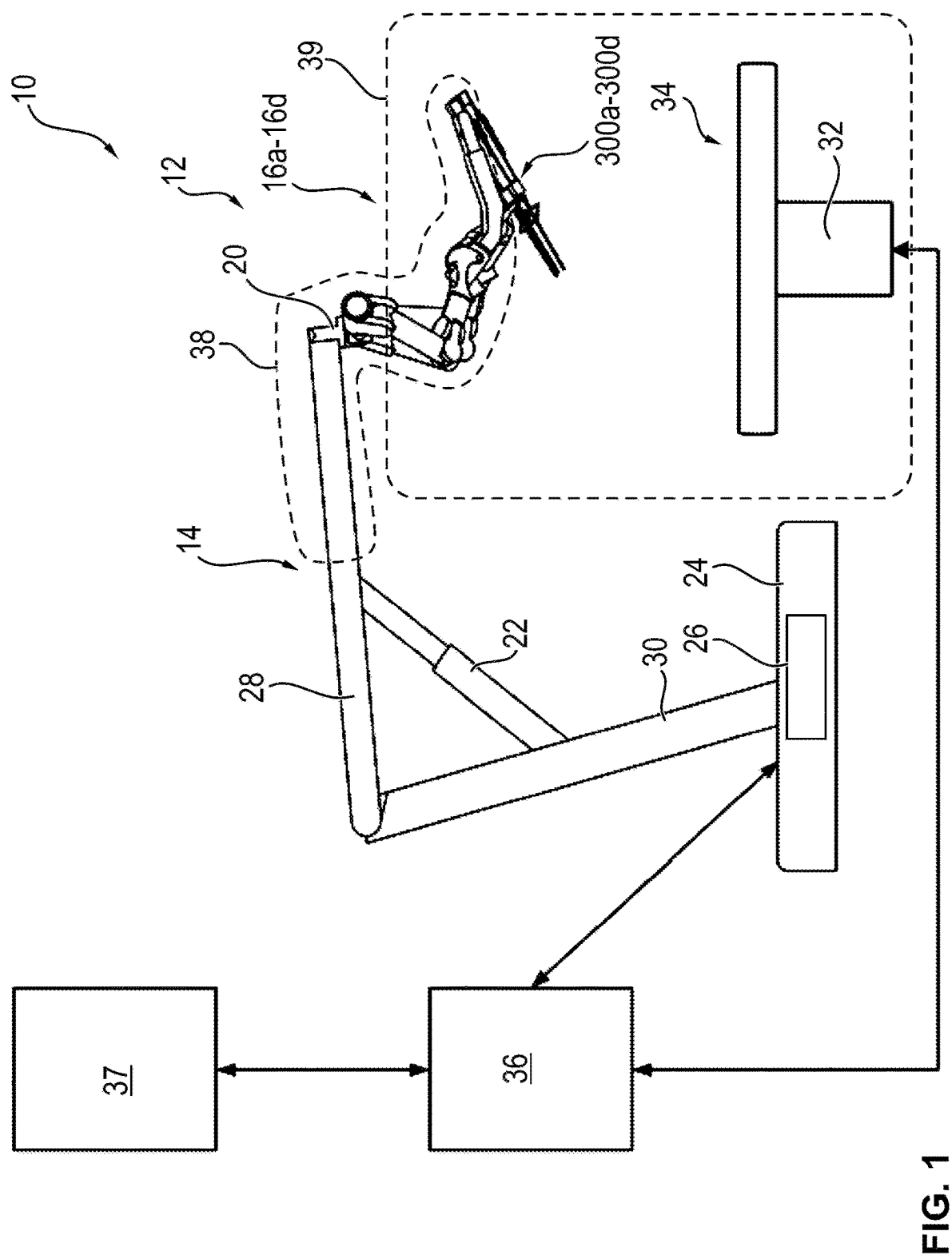
FIG. 1 shows a schematic illustration of a system for robot-assisted surgery comprising a manipulator having four manipulator arms to each of which one sterile unit of an instrument unit is connectable.

FIG. 1 shows a schematic illustration of a system 10 for robot-assisted surgery with a manipulator 12 having a mount 14 and four manipulator arms 16a to 16d. In other embodiments, the manipulator 12 can also have more or less manipulator arms 16a to 16d. Each manipulator arm 16a to 16d is connected to a sterile instrument unit 300a to 300d via a coupling unit of the manipulator arm 16a to 16d. The instrument unit 300a to 300d is sterile and comprises in addition to the sterile unit for coupling the instrument unit 300a to 300d to the coupling unit of the manipulator arm 16a to 16d, a surgical instrument, in particular an end effector, wherein the end effector can be moved and/or actuated by means of the coupling unit of the manipulator arm 16a to 16d. Alternatively to the surgical instrument, the instrument unit 300a to 300d can also comprise an optical instrument, in particular an endoscope, and/or a medical device, in particular for the application of a medicine, for dispensing a rinsing fluid and/or for aspiration of rinsing fluid and/or secretion.

The mount 14 has a mount base 24 standing on the floor of an operating room. The manipulator arms 16a to 16d are connected to a mount head 20 of the mount 14. In other embodiments, the mount can also be a ceiling mount.

The position of the mount head 20 is adjustable by means of a first drive unit 22 and by means of a second drive unit 26 arranged in the mount base 24. By means of the drive unit 22, mount arms 28, 30 are movable relative to each other. By means of the drive unit 26, the inclination of the mount arm 30 relative to the support surface of the mount base 24 can be changed and/or the mount arm 30 can be rotated about a vertical axis of rotation. In general, the positioning of the mount head 20 takes place prior to a surgery of a patient. During the surgery, the position of the mount head 20 relative to the column 32 of an operating table 34 normally remains unchanged. The manipulator 12 is controlled by means of a control unit 36. The control unit 36 is connected via a data and/or control line to an input and output unit 37 which in particular outputs an image of the operation field to a user in real time by means of at least one display unit. The user makes user inputs by which the instrument units 300a to 300d are positioned and actuated during the operation of the patient. The input and output unit 37 thus serves as a human machine interface.

The control unit 36 is further connected via a control and/or data connection to a non-illustrated control unit of the operating table 34. Via this control and/or data connection it is guaranteed that the position of the patient support surface or of segments of the patient support surface of the operating table 34 can only be changed when this is safely possible for a patient to be operated owing to the positioning of the instruments units 300a to 300d.

The operating table 34 as well as the instrument units 300a to 300d are arranged in a sterile operating area 39. The manipulator arms 16a to 16d and the mount 14 are not sterile. The areas of the manipulator 12 projecting into the sterile operating area 39, i.e. the manipulator arms 16a to 16d, the mount head 20 and a part of the mount arm 28 are packed in a sterile manner in a sterile flexible cover 38, such as a sterile foil, indicated by means of the broken line, so that they can be safely arranged in the sterile operating area 39. The input and output unit 37 is arranged outside the sterile area 39 and thus does not have to be packed in a sterile manner.

In a large number of surgeries the instrument units 300a to 300d have to be changed several times during the surgery owing to the course of the surgery. Thus, between the manipulator arm 16a to 16d and the instrument unit 300a to 300d a sterile interface has to be provided which guarantees that the non-sterile parts of the coupling unit of the manipulator arm 16a to 16d are covered in a sterile manner even after the separation of the instrument unit 300a to 300d. In addition, elements of the instrument unit 300a to 300d contaminated by a contact of the sterile elements of the coupling unit of the manipulator arm 16a to 16d have to be covered in a sterile manner after the separation of the instrument unit 300a to 300d from the manipulator arm 16a to 16d so that the instrument unit 300a to 300d can be placed in the sterile area 39 without contaminating further elements in the sterile area 39. According to the invention, a sterile lock is provided between the coupling unit of the manipulator arm 16a to 16d and the instrument unit 300a to 300d, which comprises at least one lock flap that is closed when no instrument unit 300a to 300d is connected to the sterile lock so that then the non-sterile coupling unit is shielded from the sterile area 39 by means of the flexible sterile cover 38 and the sterile lock integrated therein. The structure and the function of the sterile lock are still described in more detail in the following in connection with FIGS. 3 to 42.

Figure 2:
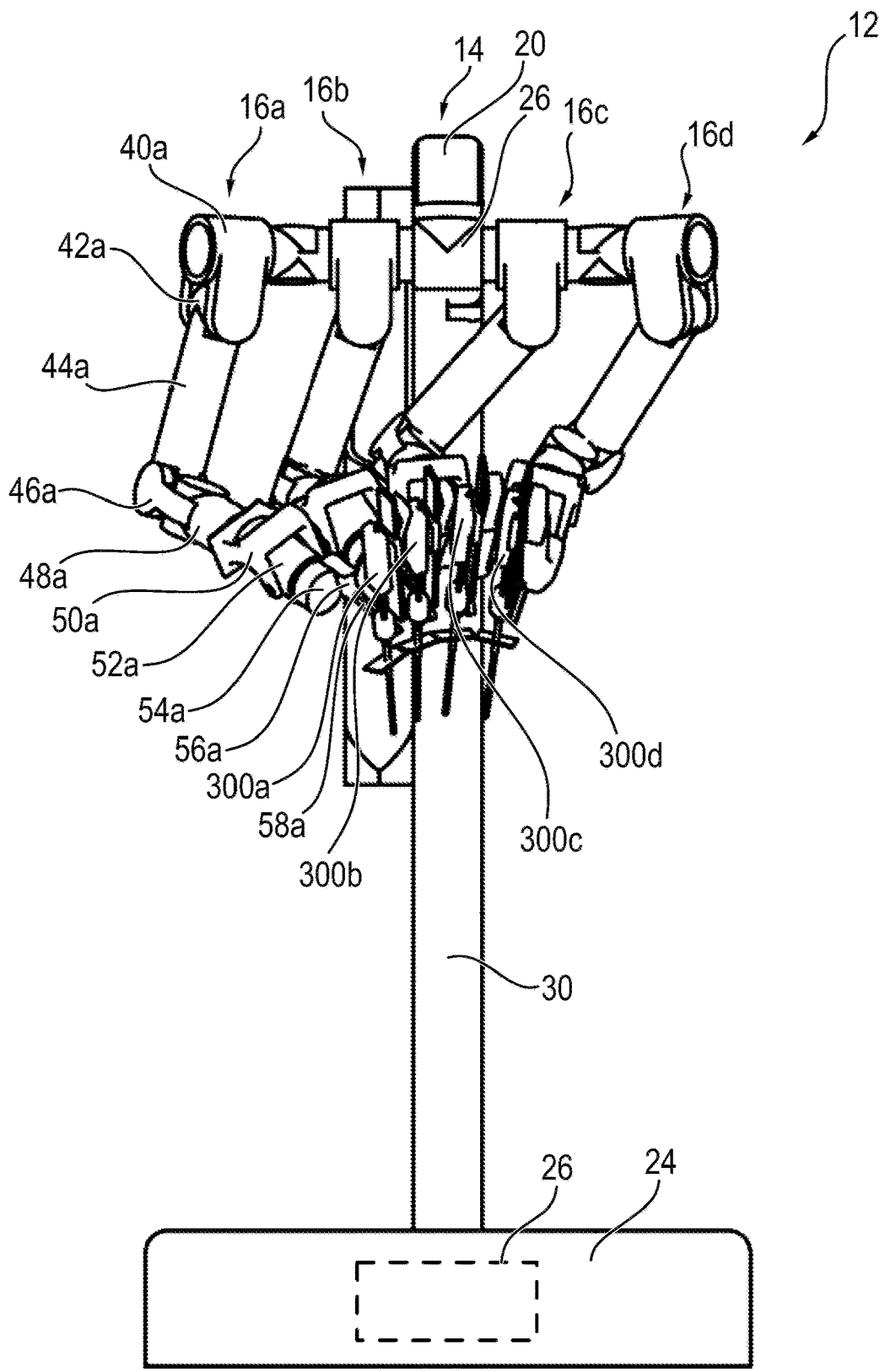
FIG. 2 shows a front view of the manipulator illustrated in FIG. 1.

In FIG. 2, a front view of the manipulator 12 according to FIG. 1 is shown. The manipulator arms 16a to 16d of the manipulator 12 each have several segments 40a to 58a which are movable relative to each other by means of integrated drive units so that the instrument units 300a to 300d can be positioned accurately without collision. The sterile covers 38 for shielding a part of the manipulator arms 16a to 16d are not illustrated in FIG. 2. The segments of the manipulator arm 16a are identified with the reference signs 40a to 58a. The further manipulator arms 16b to 16d have the same structure and have the segments 40b to 58b, 40c to 58c and 40d to 58d not identified in FIG. 2 for reasons of clarity. The same elements of the manipulator arms 16a to 16d are identified with the same reference sign and the additional letter for distinguishing the manipulator arms 16a to 16d. The statements made in the following description refer to the manipulator arm 16a and the instrument unit 300a which are identified in the following with manipulator arm 16 and instrument unit 300. The segments 40a to 58a of the manipulator arm 16a are identified in the following as segments 40 to 58. The explanations, however, apply in the same manner to the identically constructed manipulator arms 16b to 16d and the instrument units 300b to 300d. Elements having the same structure and/or the same function are identified with the same reference signs.

Figure 3:
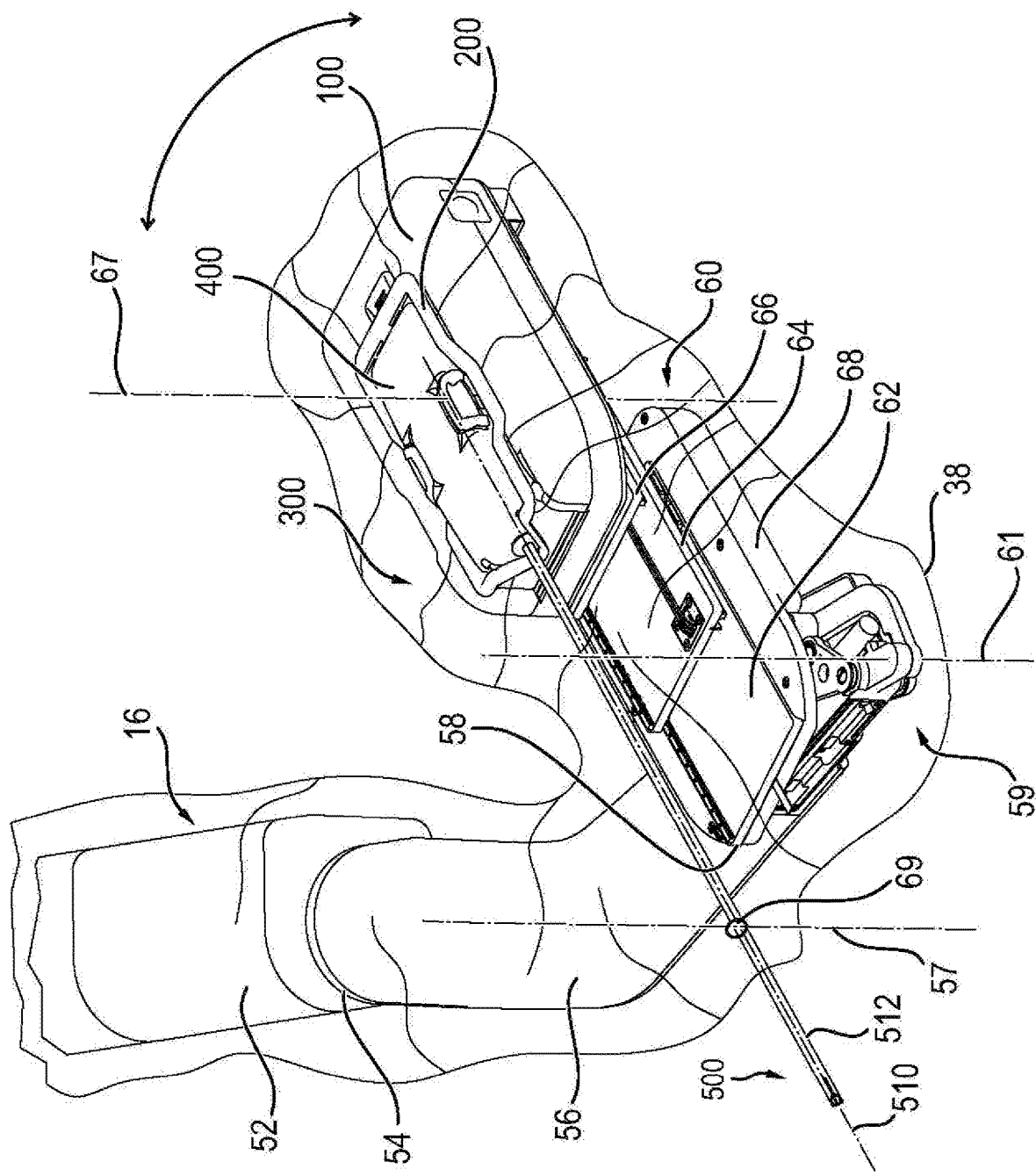
FIG. 3 shows a perspective illustration of a part of a manipulator arm with a coupling unit for coupling the manipulator arm to an instrument unit comprising a sterile unit, a sterile lock coupled to the coupling unit, and a sterile unit of the instrument unit coupled to the sterile lock.

FIG. 3 shows a perspective illustration of a part of the manipulator arm 16 with a coupling unit 100 for coupling the manipulator arm 16 to the instrument unit 300 comprising a sterile unit 400. For this, the coupling unit 100 is connected to a sterile lock 200 integrated in the sterile cover 38. The sterile lock 200 is couplable and again separable both to the coupling unit 100 and to the sterile unit 400. In FIG. 3, the sterile lock 200 is illustrated so as to be coupled both to the coupling unit 100 and to the sterile unit 400. The coupling unit 100 is arranged at the distal end of the telescopic arrangement 60.

The telescopic arrangement 60 has sections 62, 64, 66 movable to each other and is illustrated in FIG. 3 in an extended state. The sections 62, 64, 66 of the telescopic arrangement 60 can be retracted and extended by means of a drive unit 68 so that a surgical instrument 500 of the instrument unit 300 can be moved along the longitudinal axis 510 of the instrument shaft 512 together with the coupling unit 100, the sterile lock 200 and the sterile unit 400. By means of a drive unit integrated into the segment 52, the segment 54 can be rotated about the axis of rotation 57 together with the segment 56 designed as an articulated arm. The segment 58 is connected to the segment 56 via a coupling gear mechanism 59 so that the segment 58 can be pivoted about the axis of rotation 61 after activation of a drive unit connected to the coupling gear mechanism 59. Further, the coupling unit 100 is arranged rotatably about the axis of rotation 67 relative to the segment 66 via a coupling gear mechanism not visible in FIG. 3. This coupling gear mechanism, too, is drivable via a drive unit connected to this coupling gear mechanism so that when this drive unit is activated, the coupling unit 100 is rotated about the axis of rotation 67. Here, the drive units of the coupling gear mechanisms are driven such that the longitudinal axis 510 of the instrument shaft 512 is pivoted about a pivot point 69 fixed in space when the manipulator arm 16 and its segments are moved so that the longitudinal axis 510 of the instrument shaft 512 inserted into a patient preferably through a trocar during a surgery is then rotated about the pivot point 69 so that it is guaranteed that by a movement of the instrument 500 only a slight stress on the patient at the entrance point of the instrument 500 into the patient is exerted and in particular an injury of the patient at the point of entering of the instrument shaft 512 is prevented.

Figure 4:
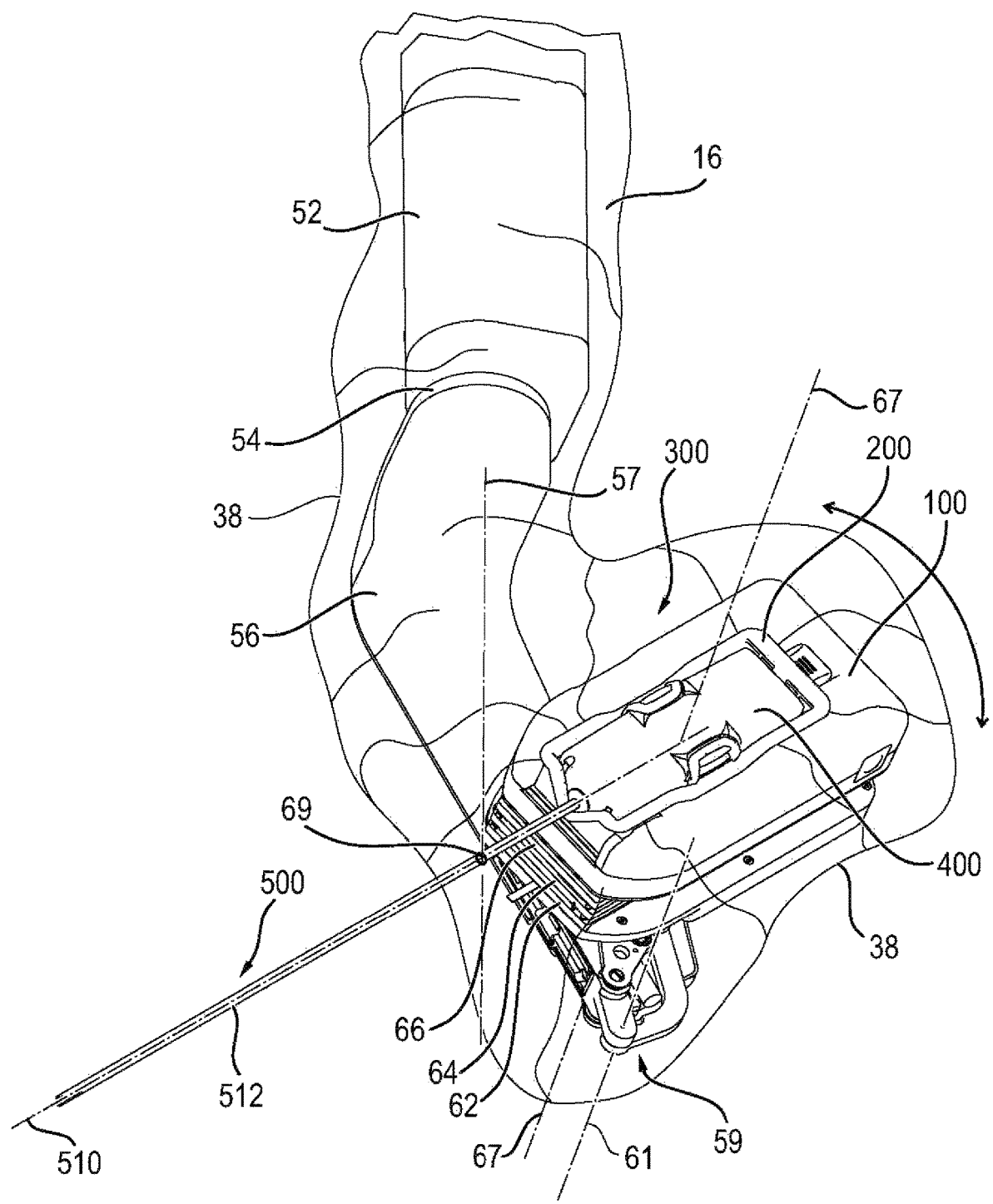
FIG. 4 shows a further perspective illustration of the arrangement according to FIG. 3.

In FIG. 4, a further perspective illustration of the arrangement according to FIG. 3 is shown, wherein the sections 62, 64, 66 of the telescopic arrangement 60 are illustrated in a retracted state in contrast to FIG. 3, as a result whereof the instrument unit 300 has been displaced in the direction of the longitudinal axis 510 of the instrument shaft 512 to the proximal end of the surgical instrument 500. Thus, by retracting the telescopic arrangement 60, the instrument unit 300 has been displaced in the direction of the proximal end of the instrument 500 along the longitudinal axis 510 of the instrument 500. In doing so, however, the position of the pivot point 69 has remained unchanged. Also given a rotation of the segments 56, 58, 60 about the axis of rotation 57, the pivot point 69 is maintained unchanged in its position in space by a corresponding drive of the drive units of the coupling gear mechanisms 59, in that a corresponding rotation of the segment 60 about the axis of rotation 61 and of the coupling unit 100 about the axis of rotation 67 takes place. Further, a virtual axis of rotation (not illustrated) which is parallel to the axes of rotation 61, 67 and orthogonal to the axis of rotation 57 and has been generated by a corresponding drive of the coupling gear mechanisms extends through the pivot point 69.

In the pivot point 69, the axis of rotation 57 of the segment 56 designed as an articulated arm and the longitudinal axis 510 of the instrument 500 intersect. The pivot point 69 is also referred to as pivotal point.

Figure 5:
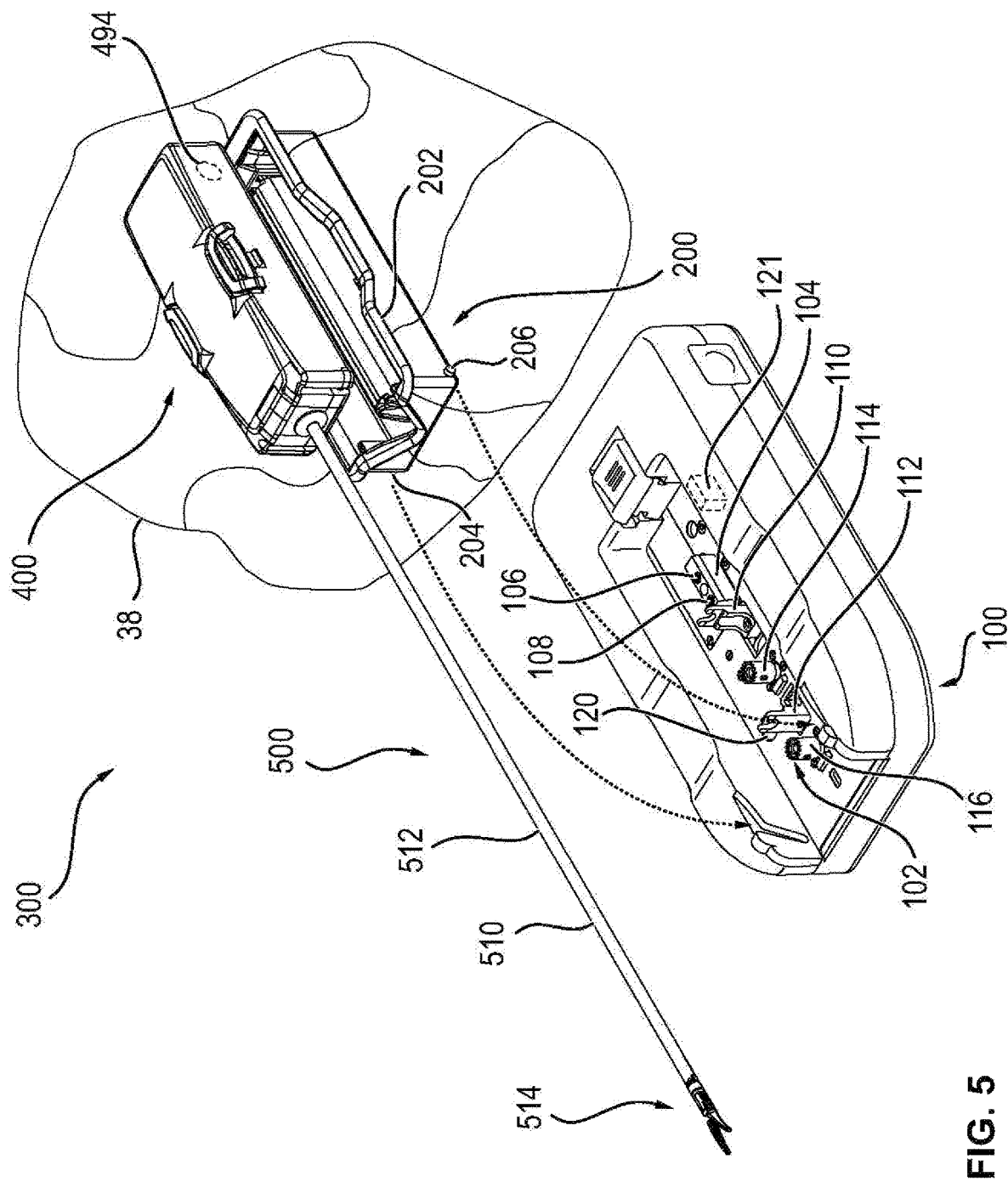
FIG. 5 shows an arrangement for connecting the instrument unit arranged in a sterile area to the non-sterile coupling unit of a manipulator arm.

FIG. 5 shows the coupling unit 100, the sterile lock 200 as well as the instrument unit 300 with the sterile unit 400 and the surgical instrument 500 having an end effector 514 prior to the connection of the sterile lock 200 to the coupling unit 100 and prior to the subsequent joining of the sterile unit 400 and the sterile lock 200. The flexible sterile cover 38 designed as a sterile foil is firmly connected to the sterile lock 200 along a circumferential connecting rim 202 of the sterile lock via a suitable connection, such as a clamping, adhesive and/or welding connection so that the sterile foil 38 forms together with the sterile lock 200 a closed sterile covering around the non-sterile elements 16, 100 to be shielded from the sterile area 39, as also shown in FIGS. 1, 3 and 4. For a better illustration, only a detail of the sterile foil 38 around the sterile lock 200 is illustrated in FIG. 5. In subsequent Figures, the sterile foil 38 is sometimes not shown.

For coupling the sterile unit 400 to the coupling unit 100 the sterile lock 200 is arranged between the sterile unit 400 and the coupling unit 100 and, in the coupled state of the sterile unit 400 to the coupling unit 100, it allows a direct coupling of a first transmitting means 102 of the coupling unit 100 and of a second transmitting means of the sterile unit 400. The second transmitting means is identified with the reference sign 406 in FIG. 15.

In the present embodiment, both mechanical energy and electrical energy is transmitted between the coupling unit 100 and the sterile unit 400 by means of the first transmitting means 102. For this, the first transmitting means 102 of the coupling unit 100 has at least four mechanical drive elements 110 to 116 and the second transmitting means 406 of the sterile unit 400 has four driven elements 412 to 418 illustrated in FIG. 15 which are complementary to the drive elements 110 to 116. Further, the first transmitting means 102 has an electrical transmitting element 104 with two electrical contacts 106, 108 and the second transmitting means 406 has an electrical transmitting element that is complementary to the electrical transmitting element 104 of the first transmitting means 102. The complementary electrical transmitting element comprises two electrical contacts 422, 423 illustrated in FIG. 11.

In other embodiments, the first and second transmitting means can also comprise more or less drive elements, driven elements and electrical transmitting elements, which transmit mechanical and/or electrical energy by direct coupling. A coupling of the transmitting means in which no further transmitting elements are provided between the first transmitting means and the second transmitting means for a transmission of mechanical and/or electrical energy and/or optical beams is regarded as a direct coupling, wherein in particular no electrical, mechanical or optical transmitting elements are provided in a sterile barrier, such as the sterile lock 200, arranged between the coupling unit 100 and the sterile unit 400. The coupling unit 100 further has an RFID read and write unit 121 by means of which an RFID transponder 494 of the sterile unit 400 is readable and/or writable.

Figure 6:
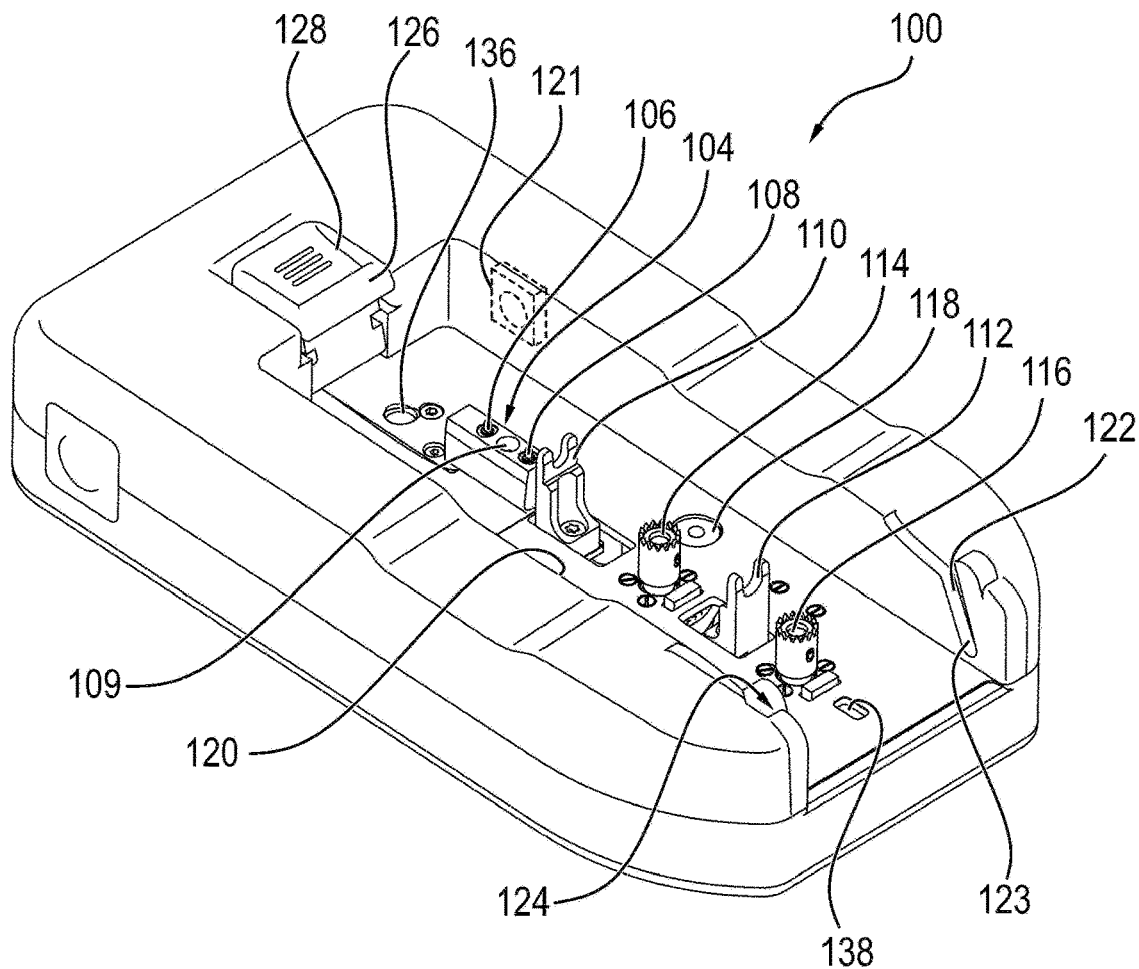
FIG. 6 shows a schematic illustration of the coupling unit of the manipulator arm.
Figure 15:
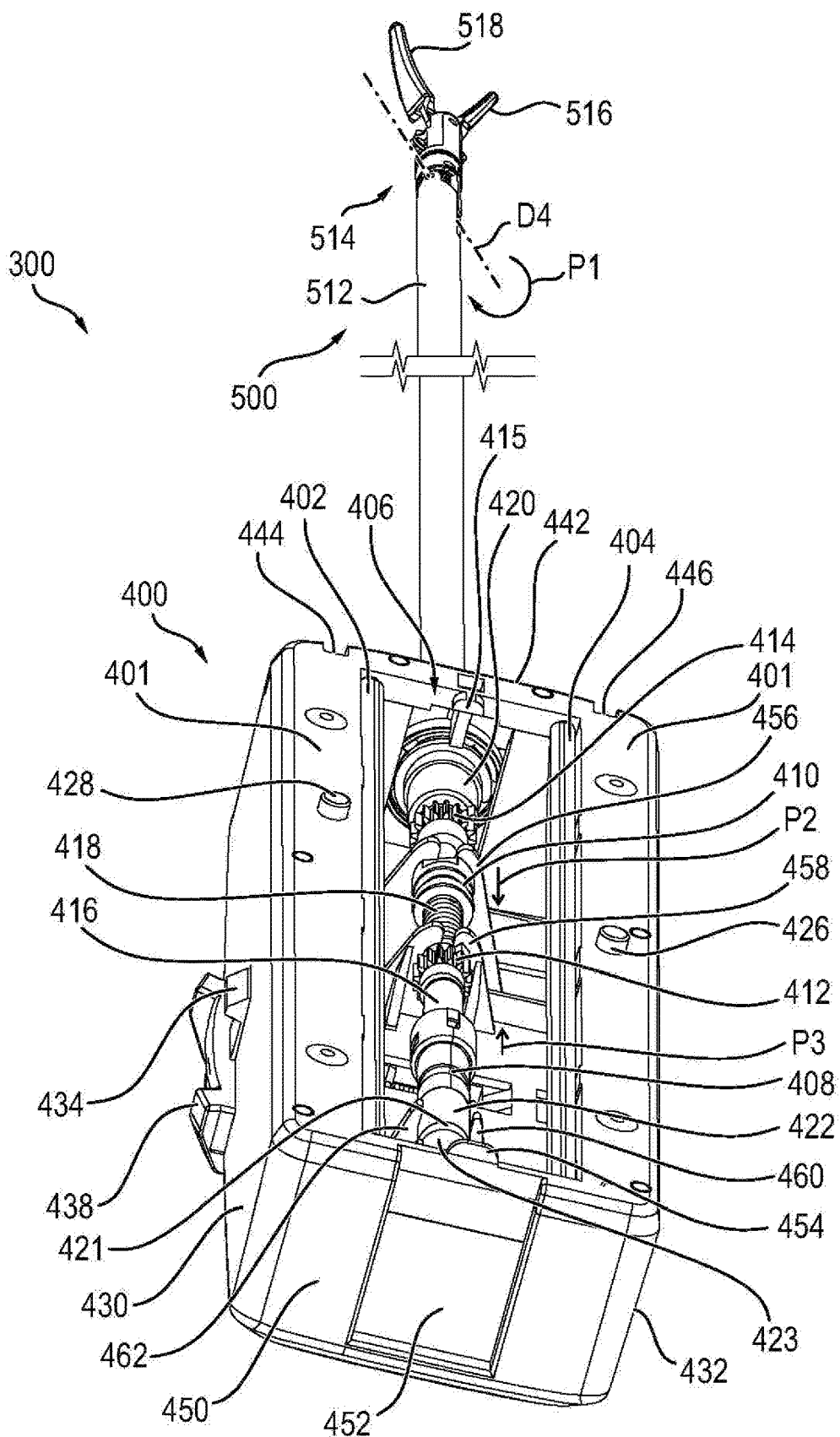
FIG. 15 shows a perspective illustration of the instrument unit with open sterile flaps of the sterile unit.

FIG. 6 shows a schematic perspective illustration of the coupling unit 100 of the manipulator arm 16. The first transmitting means 102 of the coupling unit 100 has an electrical transmitting element 104 with two electrical contacts 106, 108, an optical transmitting means 109 for transmitting light and/or optical signals, a first translatory drive element 110 and a second translatory drive element 112, each of which for transmitting a translatory movement, as well as a first rotatory drive element 114 and a second rotatory drive element 116 for transmitting a rotary motion. The first and the second translatory drive element 110, 112 are each designed as a linear lift fork and the first and the second rotatory drive element 114, 116 are designed as drive pinions with end-side teeth. Further, the coupling unit 100 has a first coupling sensor 118 arranged in a recess and detecting a first detection element formed by a first detection pin projecting from the sterile unit 400 when the sterile lock 200 is correctly coupled to the coupling unit 100 and when the sterile unit 400 is correctly coupled to the sterile lock 200. In this case, a first detection pin of the sterile unit 400 projects into the recess in which the first coupling sensor 118 is arranged so that it detects the presence of the first detection pin serving as a first detection element. The first detection pin is shown in FIG. 15 and is identified with the reference sign 426 therein.

Figure 10:
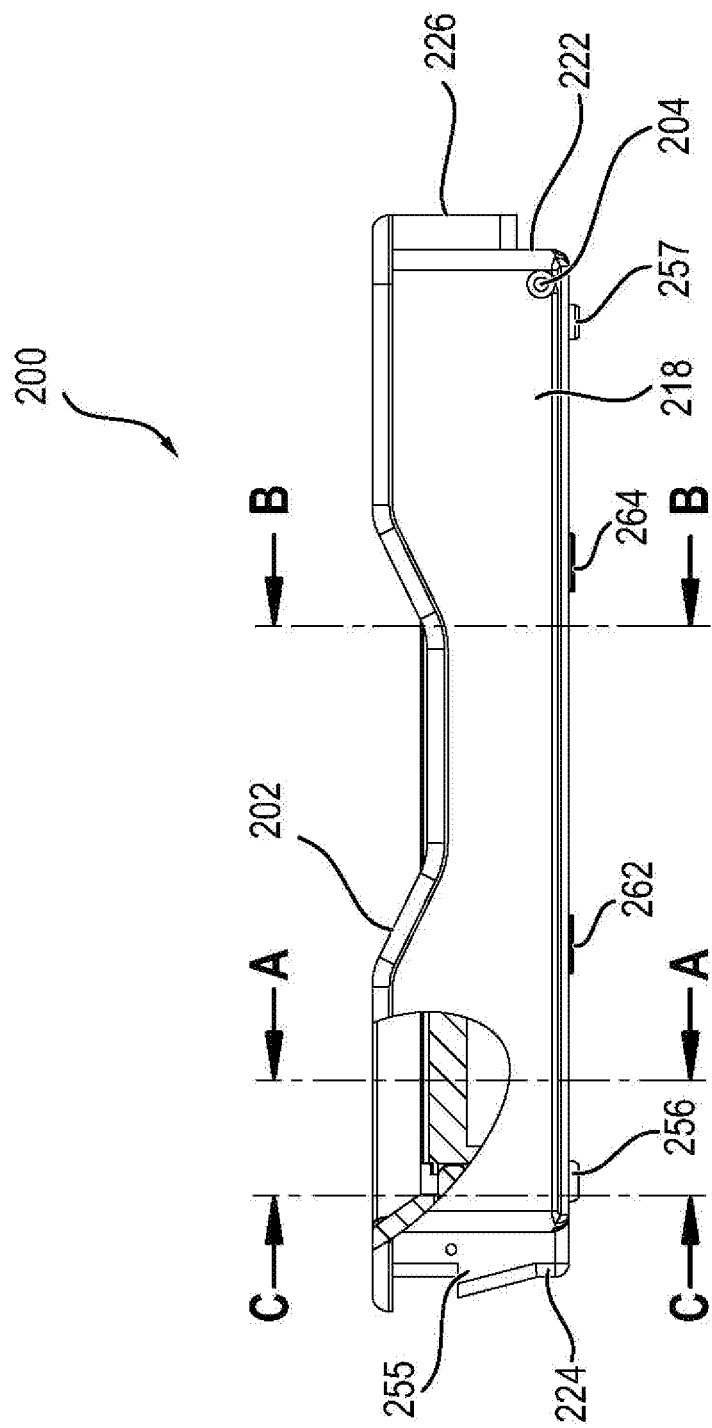
FIG. 10 shows a partial sectional side view of the sterile lock.
Figure 11:
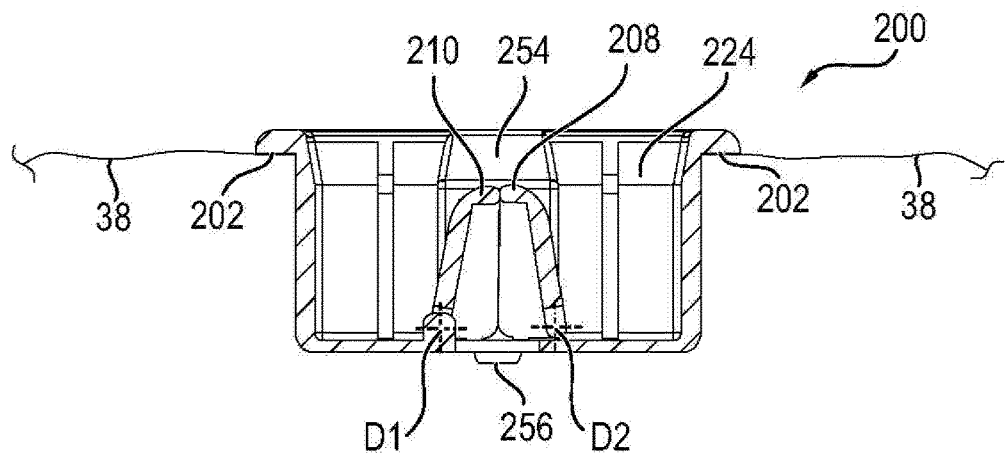
FIG. 11 shows a sectional illustration of the sterile lock according to FIG. 10 along the sectional line A-A.

The coupling unit 100 has a second coupling sensor 120 which is arranged laterally next to the drive elements 112, 114 in a further recess, as can be seen more clearly in FIG. 5. The second coupling sensor 120 detects a second detection element formed by a second detection pin of the sterile unit 400 when both the coupling unit 100 is correctly coupled to the sterile lock 200 and the sterile lock 200 is correctly coupled to the sterile unit 400. The second detection pin is shown in FIG. 11 and identified therein with the reference sign 428. Thus, it is reliably determined by means of the coupling sensors 118, 120 whether the sterile unit 400 is correctly coupled to the coupling unit 100 so that a direct transmission between the first transmitting means 102 of the coupling unit 100 and the second transmitting means of the sterile unit 400 is possible. For connecting the coupling unit 100 to the sterile lock 200, the coupling unit 100 has opposite guiding grooves 122, 124 into which the guiding pins 204, 206 of the sterile lock 200 are inserted until they have reached the front end 123, 125 of the respective guiding groove 122, 124, as shown in FIG. 10. At a first end of the sterile lock 200, the guiding pins 204, 206 project outward on opposite sides, as can be seen in FIGS. 5 and 10. Thereafter, the opposite second end of the sterile lock 200 is pushed downward so that the sterile lock 200 is rotated about an axis of rotation running through the guiding pins 204, 206 until a snap-in nose 126 of a snap-in element 128 engages with a complementary snap-in area of the sterile lock 200.

Figure 7:
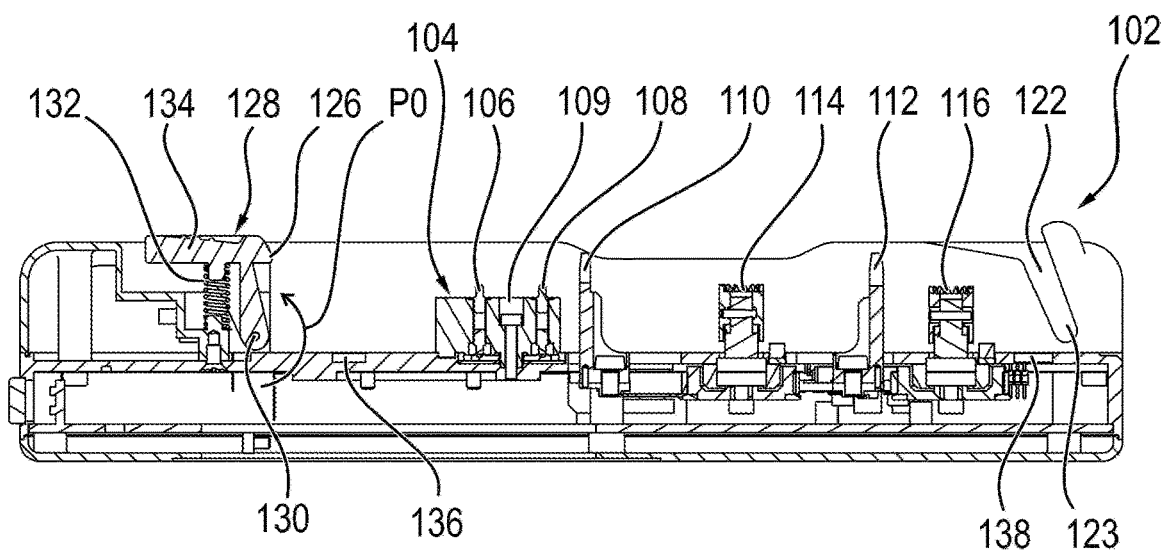
FIG. 7 shows a longitudinal section of the coupling unit according to FIG. 6.

FIG. 7 shows a longitudinal section through the coupling unit 100. The unlocking button 128 is swivel-mounted about an axis of rotation 130 and is held in its snap-in position shown in FIG. 7 by a spring 132. For disconnecting the snap-in connection, an unlocking button 134 of the snap-in element 128 is pressed by a finger so that a spring 132 is tensioned and the snap-in element 128 together with the snap-in nose 126 is rotated in the direction of the arrow P0 so that the snap-in nose 126 is disengaged from the complementary snap-in element of the sterile lock 200. As a result, the second end of the sterile lock 200 previously engaged with the snap-in nose 126 can be pivoted out of the coupling unit 100. After this second end of the sterile lock 200 has been pivoted out of the coupling unit 100, the sterile lock 200 can be completely separated from the coupling unit 100 in that the sterile lock 200 is pulled out of the guiding grooves 122, 124 along the latter together with the guiding pins 204, 206 engaged with the guiding grooves 122, 124 until the guiding elements 204, 206 are no longer engaged with the guiding grooves 122, 124. Between the guiding grooves 122, 124 and the snap-in element 128 a receiving area formed by a corresponding recess in the housing of the coupling unit 100 is provided, which in the present embodiment surrounds the sterile lock 200 on three sides and at least in part on the bottom side.

Figure 8:
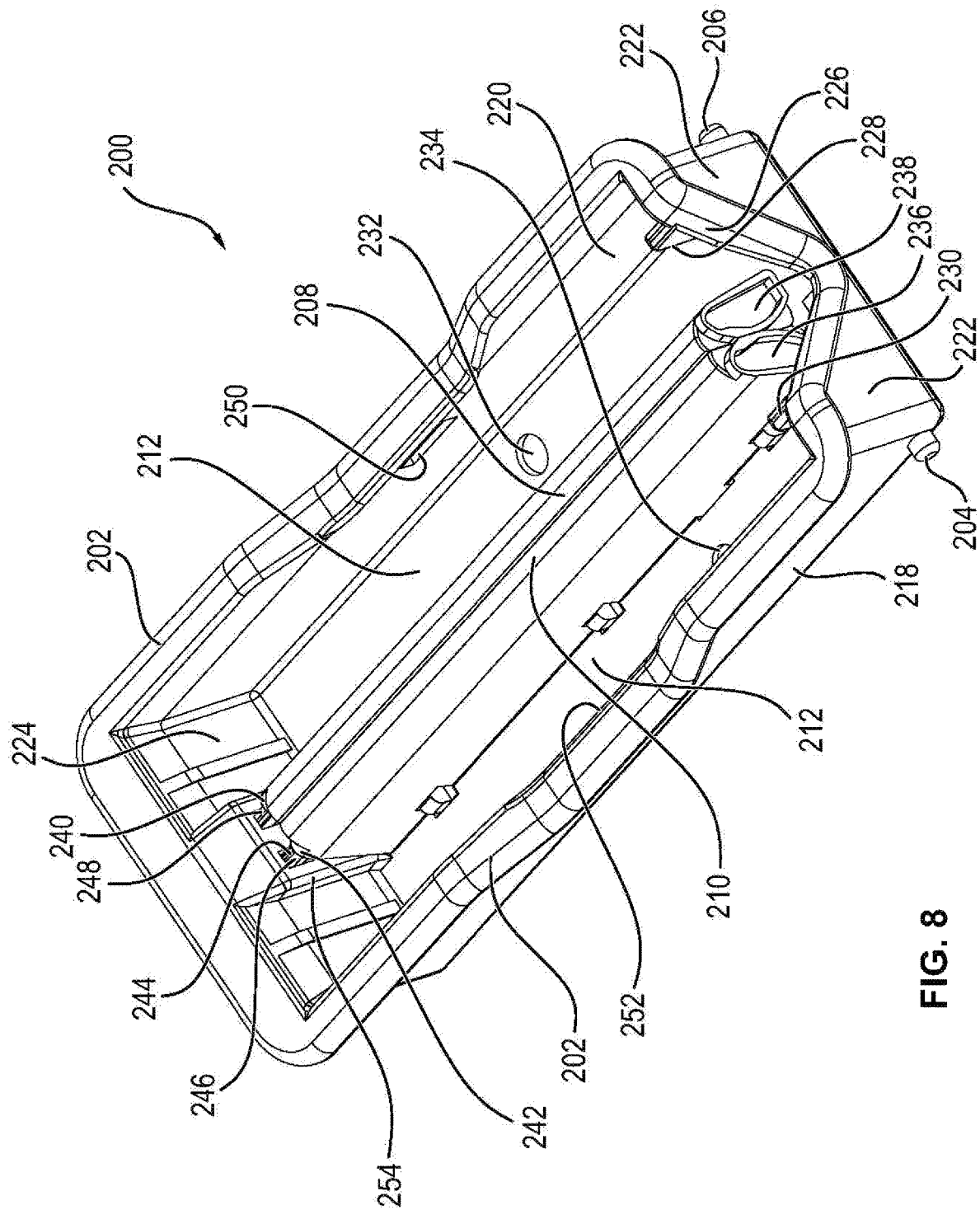
FIG. 8 shows a perspective illustration of the sterile lock with closed and locked sterile flaps.
Figure 9:
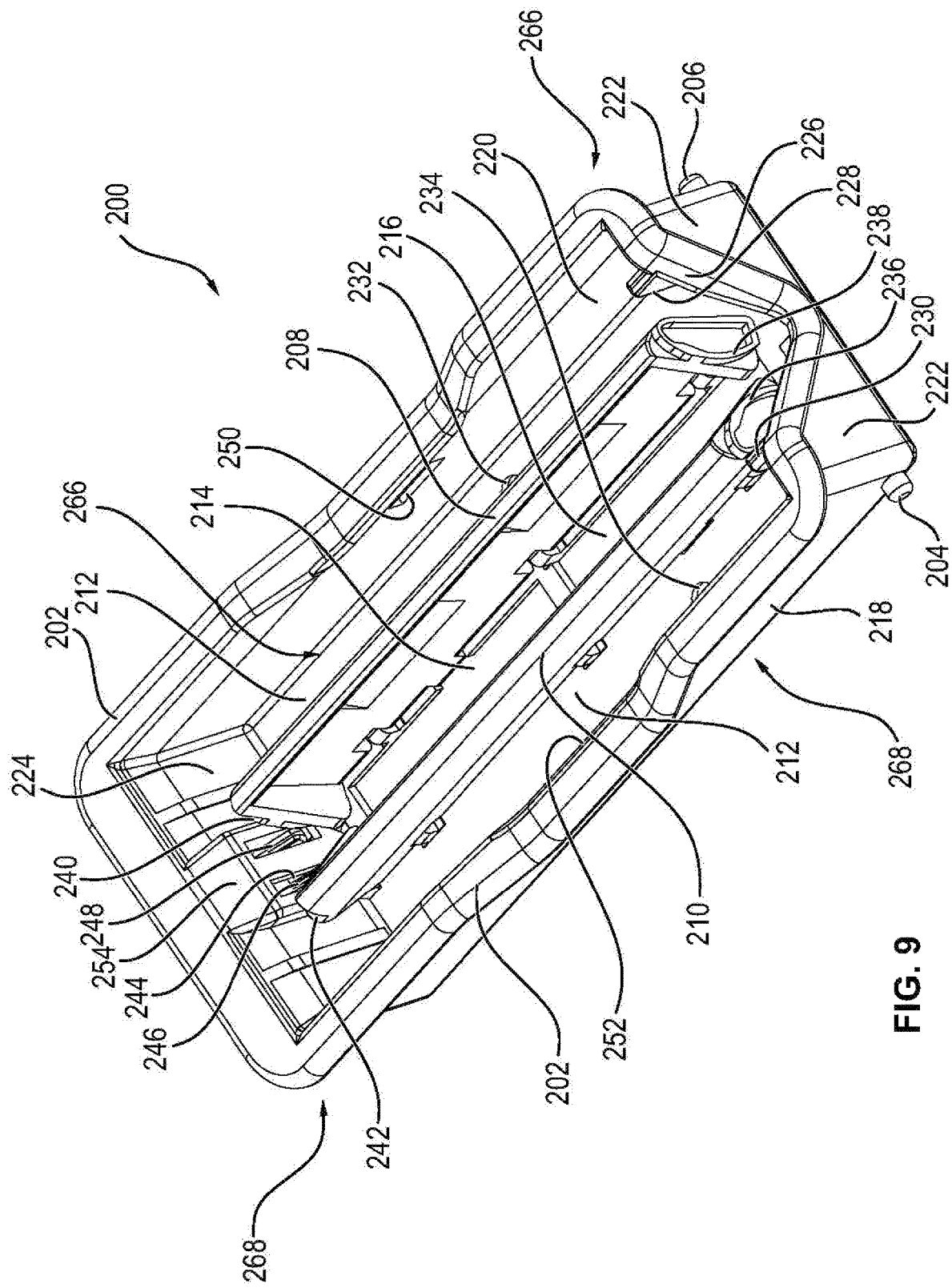
FIG. 9 shows a perspective illustration of the sterile lock according to FIG. 8 with open sterile flaps.

FIG. 8 shows a perspective view of the sterile lock 200 with closed lock flaps 208, 210. FIG. 9 shows a perspective view of the sterile lock 200 with open lock flaps 208, 210. The sterile lock 200 has a bottom 212 in which two openings 214, 216 are provided which can be covered by means of the lock flaps 208, 210. The lock flaps 208, 210 are pivotally connected to the bottom 212 via hinges. By means of these hinges the lock flaps 208, 210 are pivotable from the closed state shown in FIG. 8 into the open state shown in FIG. 9. In the open state of the lock flaps 208, 210 a direct coupling of the first transmitting means 102 of the coupling unit 100 with the second transmitting means of the sterile unit 400 can be accomplished.

The sterile lock 200 further has two side walls 218, 220, a front end wall 222 and a rear end wall 224. On the outsides of the side walls 218, 220 and the end walls 222, 224 the circumferential edge 202 is formed with which, as already described in connection with FIG. 5, the sterile foil of the sterile cover 38 is connected in a suitable manner.

On the inside of the front end wall 222 two guiding and unlocking webs 228, 230 are firmly arranged on each side next to a V-shaped recess 226 of the end wall 222, which webs serve as unlocking elements for unlocking the sterile flaps of the sterile unit 400 when connecting the sterile lock 200 to the sterile unit 400, as will still be described in more detail in the following.

In the bottom 212 of the sterile lock 200, a first detection window 232 and a second detection window 234, each in the form of a through hole, are provided, through which the already mentioned detection elements 426, 428 of the sterile unit 400 are passed so that they can be detected by the first coupling sensor 118 and by the second coupling sensor 120 of the coupling unit 100.

At the front and rear end of the lock flaps 208, 210, one guiding bead 236 to 242 each is provided. The front guiding beads 236, 238 have no function. In the closed state of the lock flaps 208, 210, the tines 246, 248 of a guiding fork 244 engage with the rear guiding beads 240, 242. The guiding fork 244 is pushed into its upper position shown in FIG. 8 by means of a spring and closes the lock flaps 208, 210 by way of engagement of its tines 246, 248 into the guiding beads 240, 242 and keeps them in their closed position. As a result of the engagement of the fork tines 246, 248, the lock flaps 208, 210 cannot be pushed apart so that the non-sterile transmitting means 102 of the coupling unit 100 is reliably covered when the lock flaps 208, 210 are closed and the non-sterile elements of the coupling unit 100 are reliably shielded from the sterile area 39.

The lock flaps 208, 210 are identical in construction so that for a both-sided use each time one guiding bead 236 to 242 is provided on both front ends of the lock flaps 208, 210. In other embodiments, the lock flaps 208, 210 can also be formed differently and have a guiding bead 240, 242 on one side only into which the tines 246, 248 of the guiding fork 244 engage.

Figure 16:
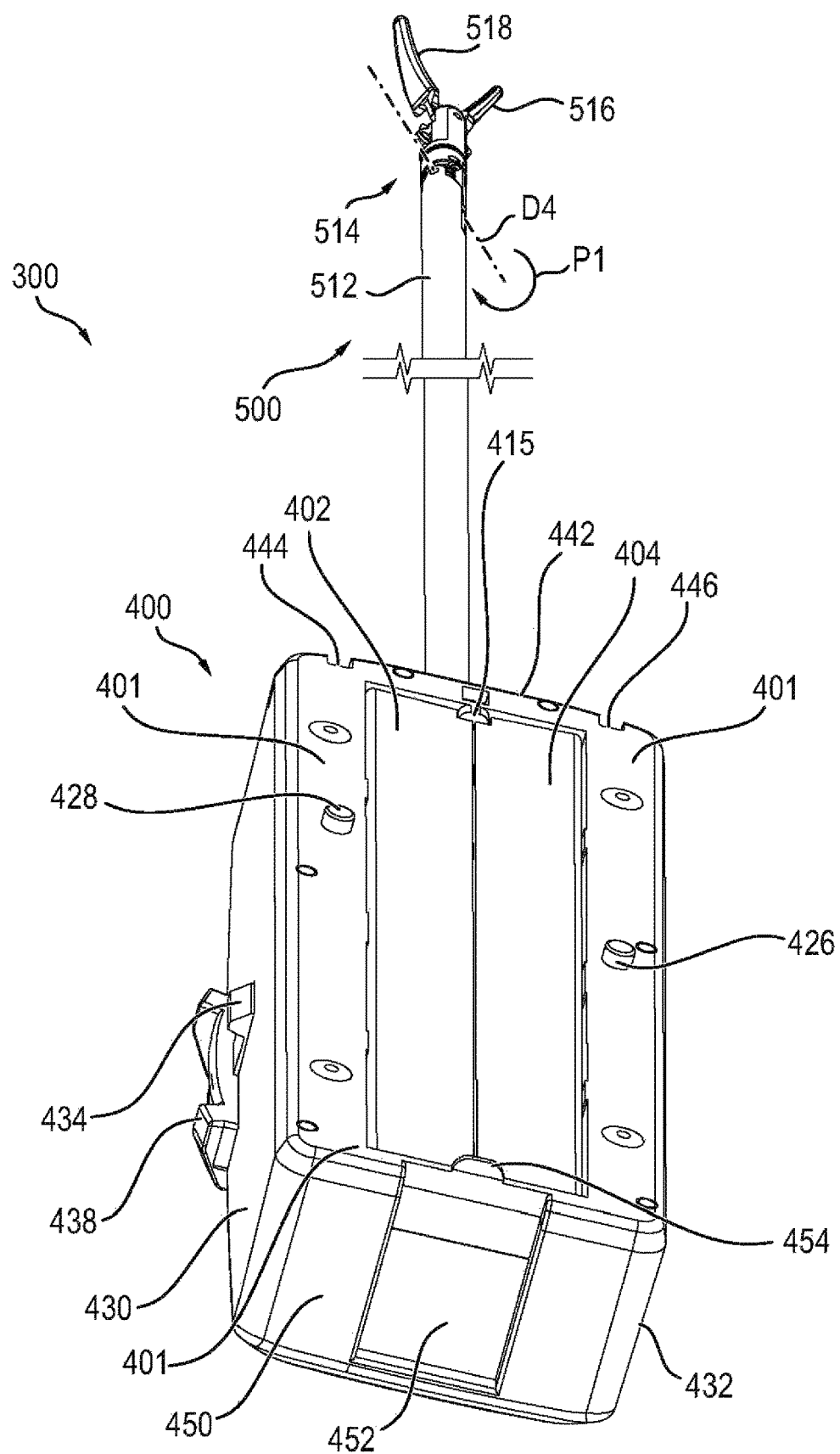
FIG. 16 shows a perspective illustration of the instrument unit according to FIG. 15 with closed sterile flaps.

In the side walls 218, 220, one snap-in bead 250, 252 each is provided into which a snap-in element of the sterile unit 400 engages when connecting the sterile lock 200 to the sterile unit 400. At the rear end wall 224 of the sterile lock 200 a guiding web 254 is provided which engages into a guiding groove 452 of the sterile unit 400 when connecting the sterile lock 200 to the sterile unit 400, as shown in FIG. 16.

FIG. 10 shows a partial sectional side view of the sterile lock 200. On the outside of the rear end wall 224 of the sterile lock 200 a snap-in nose 255 is formed into which the snap-in nose 126 of the snap-in element 128 of the coupling unit 100 engages when the coupling unit 100 is connected to the sterile lock 200.

For a correct positioning of the sterile lock 200 in the receiving area of the coupling unit 100, two positioning elements 256, 257 projecting from the bottom are provided which engage with corresponding openings 136, 138 in the bottom of the receiving area of the coupling unit 100. The positioning elements 256, 257 are chamfered or alternatively conical, so that they can easily be inserted into the openings 136, 138 of the coupling unit 100 shown in FIG. 7.

The detection windows 232 and 234 are each covered with a foil 262, 264 which still shields the detection elements 426, 428 of the sterile unit 400 in a sterile manner even when these project through the detection windows 232, 234 up into the recesses of the sensors 118, 120 of the coupling unit 100. In doing so, the foil 262, 264 is elastically and/or plastically deformed and does not tear apart.

FIG. 11 shows a sectional illustration of the sterile lock 200 according to FIG. 10 along the sectional line A-A. In this Figure, the axis of rotation about which the lock flap 110 is pivoted from the closed into the open state and vice versa is identified with D1 and the axis of rotation about which the lock flap 208 is pivoted is identified with D2.

Figure 12:
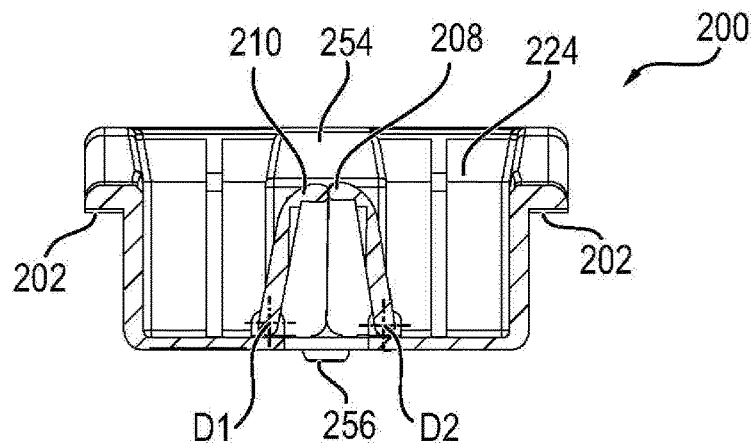
FIG. 12 shows a sectional illustration of the sterile lock according to FIG. 10 along the sectional line B-B.
Figure 13:
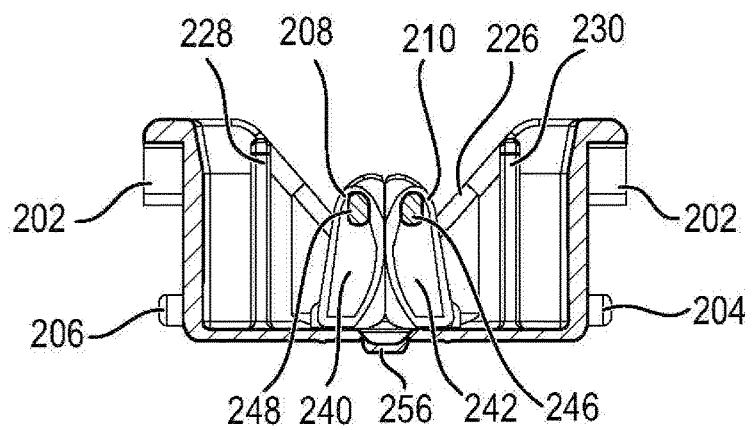
FIG. 13 shows a sectional illustration of the sterile lock according to FIG. 10 along the sectional line C-C.

FIG. 12 shows a sectional illustration of the sterile lock 200 according to FIG. 10 along the sectional line B-B and FIG. 13 shows a sectional illustration of the sterile lock 200 according to FIG. 10 along the sectional line C-C. As can be seen from FIGS. 8 to 13, the side walls 218, 220, the end walls 222, 224 and the bottom 218 form a housing trough into which the sterile unit 400 is insertable at least in part for connecting the sterile unit 400 to the coupling unit 100. The housing trough thus generally serves as a first connecting area 266 of the sterile lock 200. The outside of the sterile lock 200 serves as a second connecting area 268 with which the sterile lock 200 is connectable to the coupling unit 100.

As can be seen in FIG. 13, the front ends of the tines 246, 248 of the guiding fork 244 engage with the guiding beads 240, 242. The facing side walls of the guiding beads 240, 242 form together with the front ends of the tines 246, 248 of the guiding fork 244 a slotted guide by which the lock flaps 208, 210 are closed when the front ends of the tines 246, 248 of the fork 244 are pivoted upward.

Figure 14:
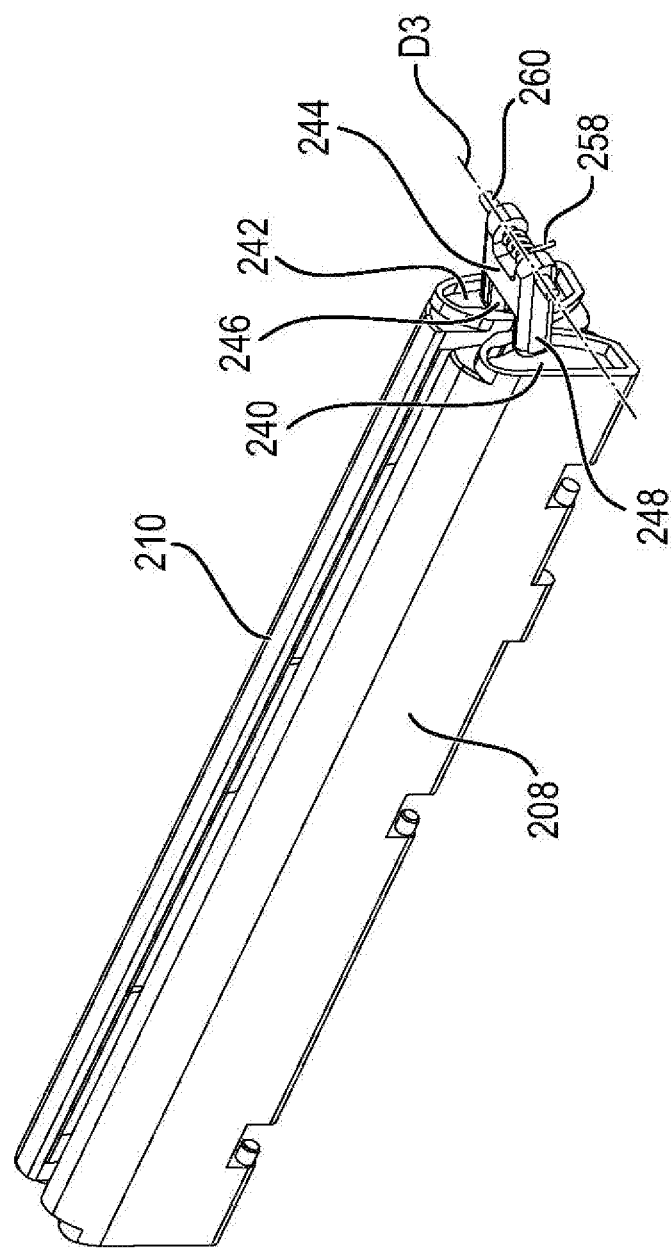
FIG. 14 shows a detailed view with partially open sterile flaps and with a guiding fork engaged with the sterile flaps.

FIG. 14 shows a detailed view with partially open lock flaps 208, 210 and the tines 246, 248 of the guiding fork 244 engaged with the guiding beads 240, 242. In the horizontal illustration of the sterile lock 200 shown in FIGS. 8 to 14, the guiding fork 244 is pivoted upward by means of a guiding fork spring 258 about an axis of rotation D3 formed by a guiding pin 260 mounted in the rear end wall 224 so that the lock flaps 208, 210 are closed by means of the spring force of the guiding fork spring 258 and are held in a closed position. The guiding pin 260 serves to guide and mount the spring 258 as well as to mount the guiding fork 244. When inserting the sterile unit 400 into the sterile lock 200, then the guiding fork 244 is pivoted downward against the spring force of the guiding fork spring 258 so that the sterile flaps 208, 210 are pivoted from the closed state into the open state by engaging elements provided on the sterile unit 400.

FIG. 15 shows a perspective illustration of the instrument unit 300 with the sterile unit 400 and the surgical instrument 500. At the proximal end of the rotatable outer instrument shaft 512 the bendable and rotatable end effector 514 with actuatable gripping arms 516, 518 is arranged. The movements of the end effector 514 can be performed by means of the drive elements 110 to 116 of the coupling unit 100 and the driven elements 408 to 414 of the sterile unit 400 when the sterile unit 400 is connected to the coupling unit 100 via the sterile lock 200. The sterile unit 400 has sterile flaps 402, 404, which are shown in an open state in FIG. 15 and in a closed state in FIG. 16. Inside the sterile unit 400, the second transmitting means is arranged which is visible when the sterile flaps 402, 404 are open and is identified with the reference sign 406. When coupled to the coupling unit, the second transmitting means 406 comprises a first translationally driven element 408 engaged with the first translatory drive element 110 and a second translationally driven element 410 engaged with the second translatory drive element 112 of the coupling unit 100, each time for transmitting a translation. Further, a first rotationally driven element 412 couplable to the first rotatory drive element 114 of the coupling unit 100 as well as a second rotationally driven element 414 engaged with the second rotatory drive element 116 of the coupling unit 100 are provided for transmitting a rotary motion each. In the surgical instrument 500 connected to the coupling unit 400, the end effector 514 is pivoted about the tilt axis D4 in the arrow direction P1 by up to 90° when the second translationally driven element 410 of the sterile unit 400 is moved by the second translatory drive element 112 of the coupling unit 100 in the direction of the arrow P2. When moving the first translationally driven element 408 in the direction of the arrow P3, the gripping arms 516, 518 of the end effector 514 are moved apart and moved towards each other in opposite directions. When driving the first rotationally driven element 412 of the sterile unit 400 with the aid of the first rotatory drive element 114 of the coupling unit 100, the end effector 514 can be rotated independent of the instrument shaft 512. By means of the second rotationally driven element 414, given a coupling and a drive by means of the second rotatory drive element 116 of the coupling unit 100, a rotation of the instrument shaft 512 about its longitudinal axis 510 can be produced to rotate the position of the tilt axis D4 of the end effector 514 about the axis of rotation 510 of the outer instrument shaft 512 without the end effector 514 itself being rotated.

Further, a first spring 416 is provided which pushes the first translationally driven element 408 of the sterile unit 400 opposite to the direction of the arrow P3 into its end position. Further, a second spring 418 is provided which pushes the second translationally driven element 410 of the sterile unit 400 opposite to the direction of the arrow P2 into its end position. Further, the sterile unit 400 has a bearing 420 for rotatably mounting the outer instrument shaft 512 in the sterile unit 400. As an alternative to the surgical instrument 500, also other instruments, such as a pair of scissors, a needle holder, optical instruments, rinsing units, aspiration units, instruments of high-frequency surgery and other instruments used in operations, in particular in laparoscopic surgeries can be coupled to the sterile unit 400, wherein the second transmitting means 406 are designed for the implementation of the corresponding functions.

According to the embodiment, the second transmitting means 406 further comprises an electrical transmitting element with a first electrical contact 422 designed as a slip ring and a second electrical contact 423 designed as a slip ring, which, when coupling the sterile unit 400 to the coupling unit 100 via the sterile lock 200, establish an electrical connection with the electrical contacts 106, 108 of the coupling unit 100 for transmitting high-frequency electrical energy for high-frequency surgery. In other embodiments, also no electrical transmitting means may be provided.

The sterile unit 400 has two projecting cams 415, 417 which upon insertion of the sterile unit 400 into the sterile lock 200 push the unlocked sterile flaps 208, 210 apart at least until the cams 415, 417 are arranged between the sterile flaps 208, 210. Upon further insertion of the sterile unit 400 into the sterile lock 200, wedge-shaped engaging elements 456 to 462 of the sterile unit 400 push the sterile flaps 208, 210 further apart until they are arranged in their open position shown in FIG. 9.

The bottom plate 401 of the sterile unit 400 facing upward in FIGS. 15 and 16 has, as already mentioned, two detection elements 426, 428 formed as projecting detection pins. When coupling the sterile unit 400 to the coupling unit 100 with the sterile lock 200 arranged between the sterile unit 400 and the coupling unit 100, the detection element 426 projects through the first detection window 232 of the sterile lock 200 into the recess of the first coupling sensor 118 of the coupling unit 100 and the second detection element 428 projects through the second detection window 234 into the recess of the second coupling sensor 120 of the coupling unit 100. When the detections elements 426, 428 are detected by means of the coupling sensors 118, 120, a correct coupling of the sterile lock 200 to the coupling unit 100 and of the sterile unit 400 to the sterile lock 200 can be detected so that only after a detection of the detection elements 426, 428 with the aid of the coupling sensors 118, 120 a drive of the transmitting elements 110 to 116 is enabled by a control unit. Further, the transmission of high-frequency energy is only enabled after the correct detection of the detection elements 426, 428 by means of the coupling sensors 118, 120 via the transmitting elements 106, 108.

Further, the sterile unit 400 has two snap-in elements 434, 436 arranged on opposite side walls 430, 432, which snap-in elements are actuatable by means of an actuating element 438, 440 projecting from the side wall 430, 432. The snap-in elements 434, 436 engage with the snap-in beads 250, 252 provided in the side walls 218, 220 of the sterile lock 200 when the sterile unit 400 is correctly connected to the sterile lock 200.

The front end wall 442 of the sterile unit 400 has two grooves 444, 446 into which the guiding and unlocking webs 228, 230 of the sterile lock 200 are inserted when connecting the sterile unit 400 to the sterile lock 200 and, in doing so, unlock the sterile flaps 402, 404, as will still be explained in more detail in the following.

Further, the guiding web 254 of the sterile lock 200 engages into the guiding groove 452 present on the rear end side 450 of the sterile unit 400. At the lower end of the guiding groove 452, an actuating web 454 projects outward from the bottom plate 401 and pushes the guiding fork 244 downward when inserting the sterile unit 400 into the sterile lock 200 and thus unlocks the lock of the lock flaps 208, 210 by the guiding fork 244.

FIG. 17 shows a side view of the sterile unit 400 with a part of the instrument shaft 512 of the surgical instrument 500. FIG. 18 shows a sectional view of the sterile unit according to FIG. 17 along the sectional line E-E. As can be seen from this sectional illustration, the sterile flap 402 is engaged with a guiding flap 464 provided in the sterile unit 400. The sterile flap 404 is engaged with a guiding flap 464 arranged inside the sterile unit 400. For opening the sterile flap 402, the sterile flap is arranged pivotally about the axis of rotation D5 and the guiding flap 464 is arranged pivotally about the axis of rotation D6. For opening the sterile flap 404, this sterile flap is arranged pivotally about the axis of rotation D7 and the guiding flap 464 is arranged pivotally about the axis of rotation D8. In the closed state, the sterile flaps 402, 404 are locked by means of the guiding flaps 464, 466 and are unlocked for opening the sterile flaps 402, 404, as will still be explained in more detail in the following in connection with FIGS. 22 to 28.

In FIG. 19, a sectional view of the sterile unit 400 according to FIG. 17 along the sectional line F-F is shown. In FIG. 19, a spring 468 is visible, by means of which the actuating elements 438, 440 and together therewith the snap-in noses 434, 436 are pressed outward so that the snap-in noses 434, 436 are pressed into the snap-in beads 250, 252 of the sterile lock 200 when the sterile unit 400 has correctly been inserted into the sterile lock 200.

Figure 20:
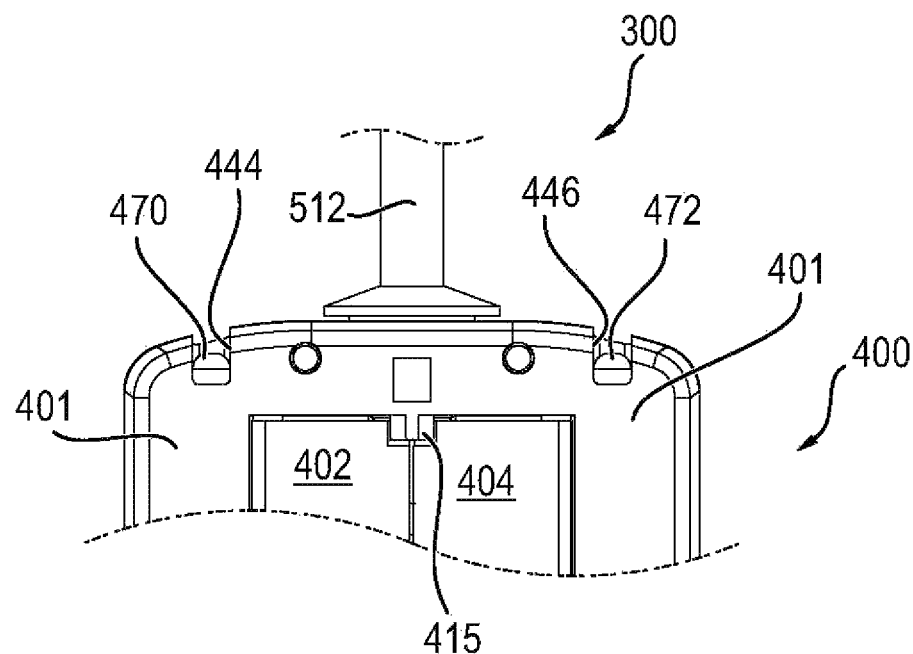
FIG. 20 shows a detail of a bottom view of the instrument unit with closed and locked sterile flaps.
Figure 21:
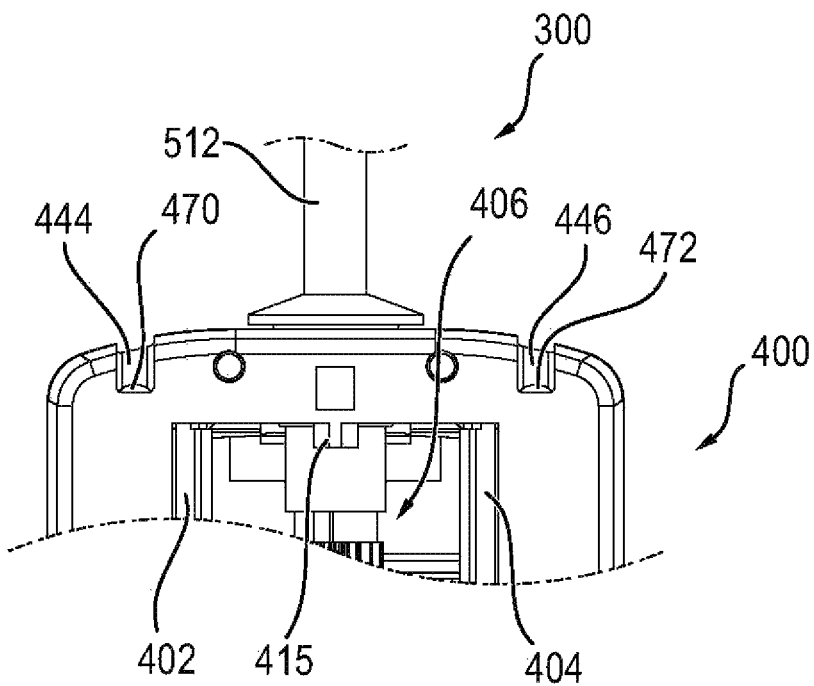
FIG. 21 shows the detail of the instrument unit according to FIG. 20 with unlocked and open sterile flaps.

FIG. 20 shows a detail of a bottom view of the instrument unit 300 with closed sterile flaps 402, 404 of the sterile unit 400. In this illustration, an unlocking pin 470 of the guiding flap 464 and an unlocking pin 472 of the guiding flap 466 are visible. The unlocking pin 470 projects into the guiding and unlocking groove 444 and the unlocking pin 472 projects into the unlocking and guiding groove 446. When connecting the sterile unit 400 to the sterile lock 200, the guiding and unlocking webs 228, 230 of the sterile lock 200 are inserted into the guiding grooves 444, 446 and press the unlocking pins 470, 472 from the locked position shown in FIG. 20 into the unlocked position shown in FIG. 21. In FIG. 21, the sterile flaps 202, 204 and the guiding flaps 464, 466 are illustrated in an unlocked and open state.

Figure 22:
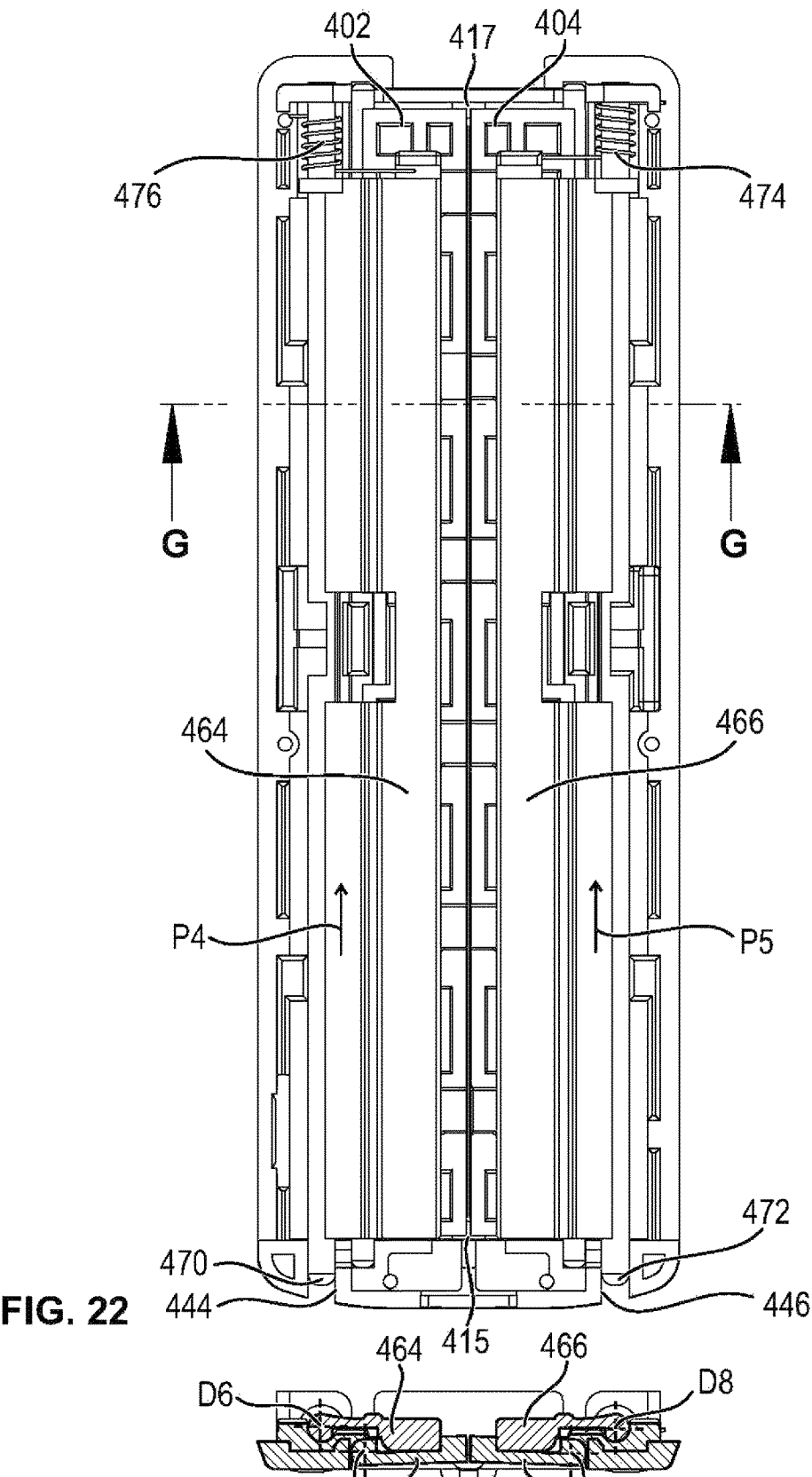
FIG. 22 shows a top view of the sterile flap system of the sterile unit with closed sterile flaps.

FIG. 22 shows a top view of the sterile flap system of the sterile unit 400 with closed sterile flaps 402, 404 and closed and locked guiding flaps 464, 466. The sterile flap system has in addition to the sterile flaps 402, 404 and the guiding flaps 464, 466 a spring 474 which is biased and keeps the guiding flap 466 and the sterile flap 404 engaged with the guiding flap 466 in the closed state shown in FIG. 22. After unlocking the guiding flap 466, the guiding flap 466 and the sterile flap 404 can be opened against the spring force of the spring 474. The sterile flap system further has a spring 476 which is biased and keeps the guiding flap 464 and the sterile flap 402 in their closed state. The guiding flap 464 and the sterile flap 402 can be opened against the spring force of the spring 476 when the guiding flap 464 has been unlocked. For unlocking the guiding flaps 464, 466, the unlocking pins 470, 472 are moved by the guiding and unlocking webs 228, 230 in the direction of the arrows P4, P5 within their little clearance up to the position illustrated in FIG. 24. In doing so, the sterile flaps 402, 404 are not or only slightly moved in the direction of the arrows P4, P5 so that for unlocking a relative movement of the guiding flaps 464, 466 relative to the sterile flaps 402, 404 in the direction of the arrows P4, P5 takes place. FIG. 23 is a sectional illustration of the sterile flap system according to FIG. 22 along the sectional line G-G with closed guiding flaps 464, 466 and closed sterile flaps 402, 404.

In FIG. 24, the guiding flaps 464, 466 and the sterile flaps 402, 404 are illustrated in their open position. FIG. 25 is a sectional illustration of the sterile flap system according to FIG. 24 along the sectional line H-H with open guiding flaps 464, 466 and open sterile flaps 402, 404.

Figure 26:
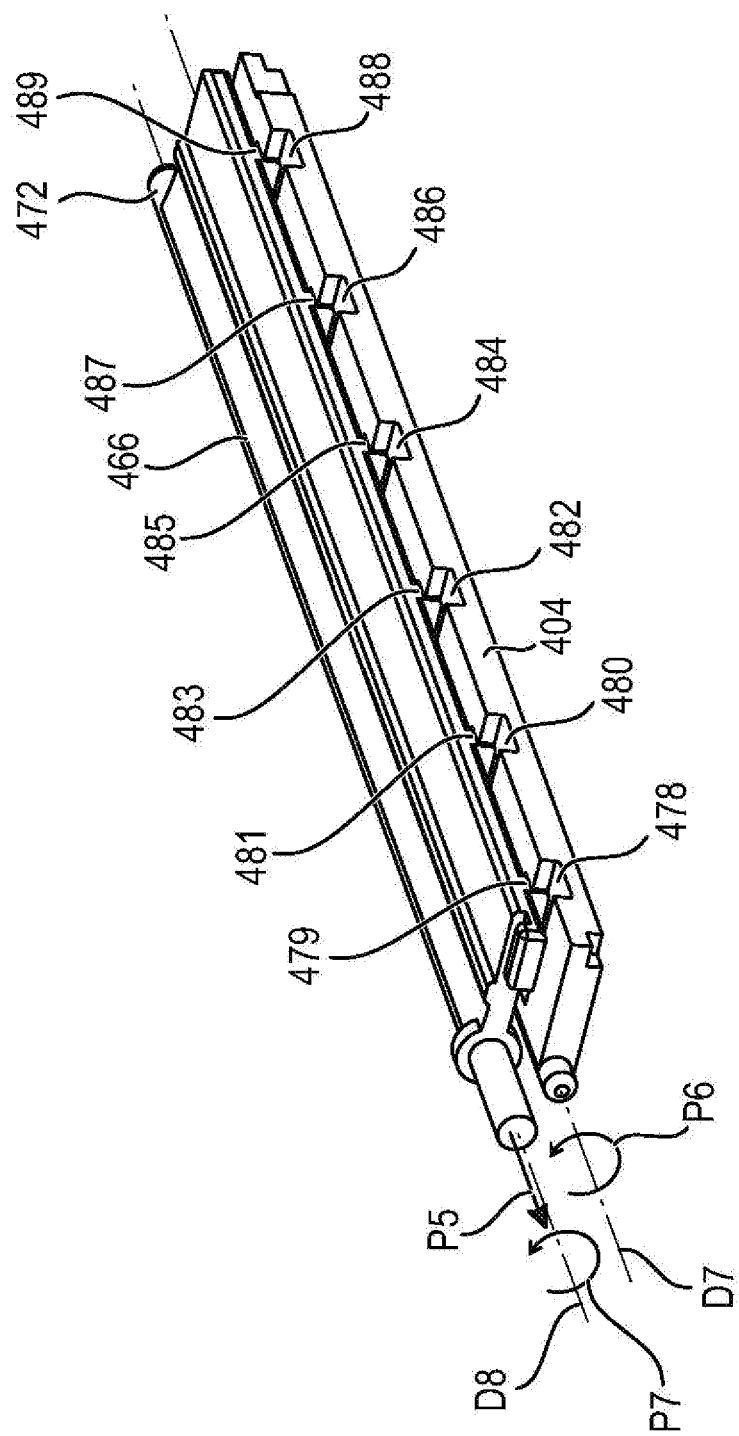
FIG. 26 shows a perspective detailed view of the sterile flap with a guiding flap of the sterile unit.

FIG. 26 shows a perspective detailed view of the sterile flap 404 and the sterile flap 404 engaged therewith in a closed locked position. In addition, the spring 474 not illustrated in FIG. 26 presses the guiding flap 466 opposite to the arrow P5 into its locked position and the spring 474 presses the guiding flap 466 additionally opposite to the direction of the arrow P4 into its locked position so that for unlocking the guiding flaps 464, 466 the unlocking pins 470, 472 are moved against the spring force of the springs 474, 476 in the direction of the arrows P4, P5.

On the side facing the guiding flap 466, the sterile flap 404 has seven guiding and locking grooves 478 to 488 into each of which one guiding and locking web 479 to 489 of the guiding flap 466 engages. The guiding and locking webs 479 to 489 are arranged on the side of the guiding flap 466 facing the sterile flap 404. The sterile flap 404 and the guiding flap 466 are illustrated in their locked position in FIG. 26. In this locked state, the guiding and locking webs 479 to 489 are each arranged behind a projection of the guiding and locking grooves 478 to 488 so that, as a result thereof, a rotation of the sterile flap 404 and of the guiding flap 466 about the axes of rotation D5, D6 in the direction of the arrows P6 and P7 is prevented. For unlocking the guiding flap 466, this guiding flap is moved in the direction of the arrow P5 by means of the unlocking pin 472 so that the guiding and locking webs 479 to 489 are moved out of the projections of the guiding and locking grooves 478 to 488 so that the guiding flap 466 and the sterile flap 404 can be moved about the axes of rotation D7, D8 in the direction of the arrows P6 and P7.

The sterile flap arrangement of the sterile flap 402 and of the guiding flap 464 are mirror-symmetrically with respect to the flap arrangement of the sterile flap 404 and the guiding flap 466 shown in FIG. 26 so that their locking and unlocking is accomplished in the same manner as described for the sterile flap 404 and the guiding flap 466.

FIG. 27 shows a top view of the guiding flap 466 and the lock flap 404 in a partial sectional illustration in the closed and locked state. In the sectional area, the guiding and locking groove 480 of the guiding flap 466 is visible.

The guiding and locking groove 480 is arranged behind the projection 490 of the guiding and locking groove 480 serving as a blocking nose so that in the case of a torque acting on the guiding flap 466 and/or on the sterile flap 404 for a rotary motion of the guiding flap 466 in the direction of the arrow P7 or the sterile flap 404 in the direction of the arrow P6, the guiding and locking element 480 would be pressed against the blocking nose 490. As a result, neither a rotation of the guiding flap 466 about the axis of rotation D8 in the direction of the arrow P7 nor a rotation of the sterile flap 404 about the axis of rotation D7 in the direction of the arrow P6 is possible. Only after the guiding flap 466 has been moved in the direction of the arrow P5, as illustrated in FIG. 28, the guiding flap 466 is rotatable about the axis of rotation D8 in the direction of the arrow P7 and the sterile flap 404 is rotatable about the axis of rotation D7 in the direction of the arrow P6. Further, in doing so, the guiding flap 466 is moved in the arrow direction P8 relative to the sterile flap 404. By moving the guiding flap 466 in the direction of the arrow P5, the guiding flap 466 has been moved relative to the sterile flap 404 so that the guiding and locking web 481 is no longer arranged behind the projection 490 but in the area of the guiding groove 480 open to the outside. As a result, the sterile flap 404 can be rotated in the direction of the arrow P6 and the guiding flap 466 can be rotated in the direction of the arrow P7 so that the sterile flap 404 and the guiding flap 466 can be moved into their open position, respectively. The further guiding and locking webs 479 to 489 are moved together with the guiding and locking web 481 out of the blocking area of the respective guiding and locking groove 478 to 488 formed by the projection, as this has been explained with respect to the guiding and locking web 481 and the guiding and locking groove 480.

Figure 29:
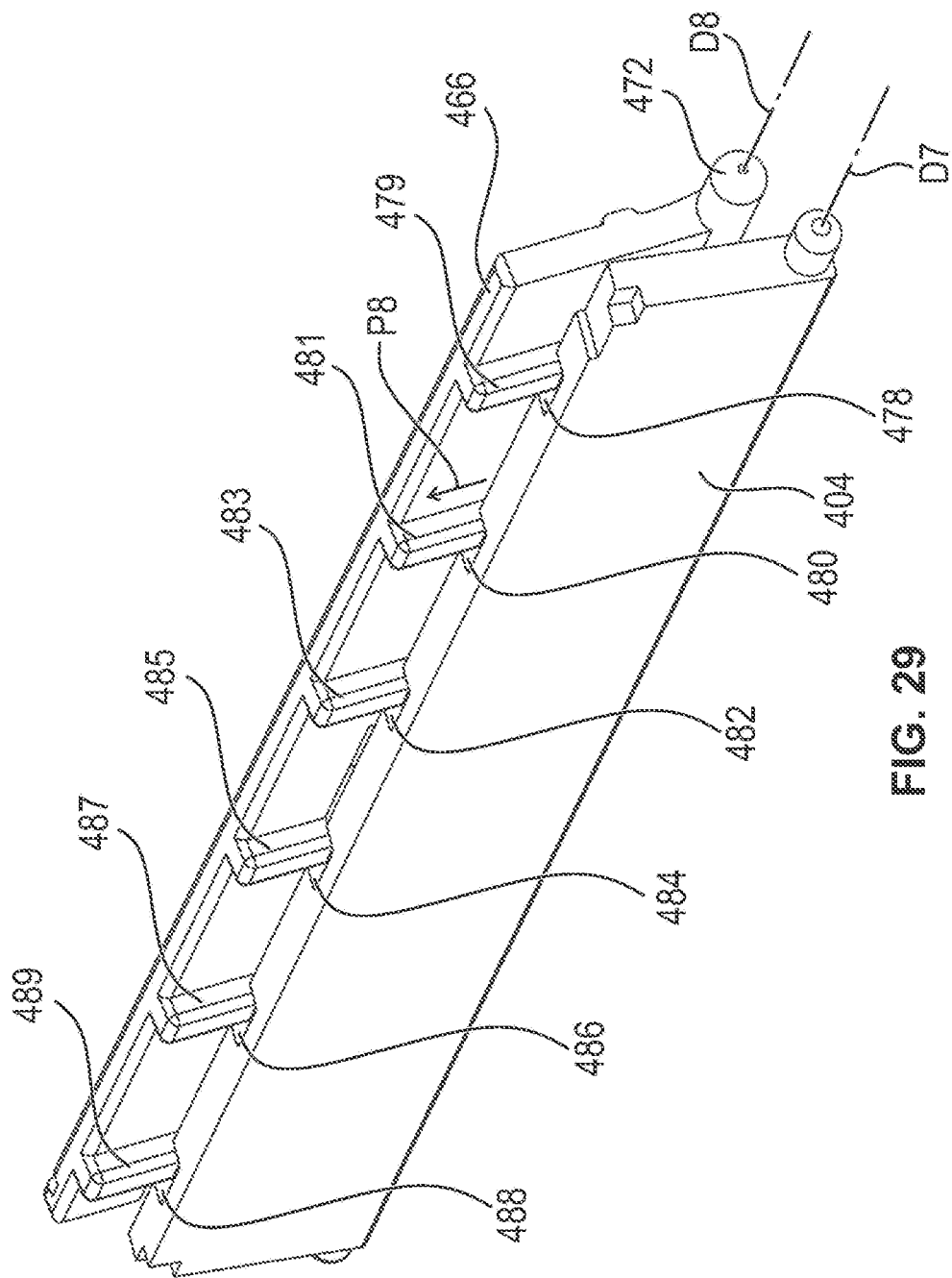
FIG. 29 shows a perspective illustration of the sterile flap and of the guiding flap in the open state.
Figure 33:
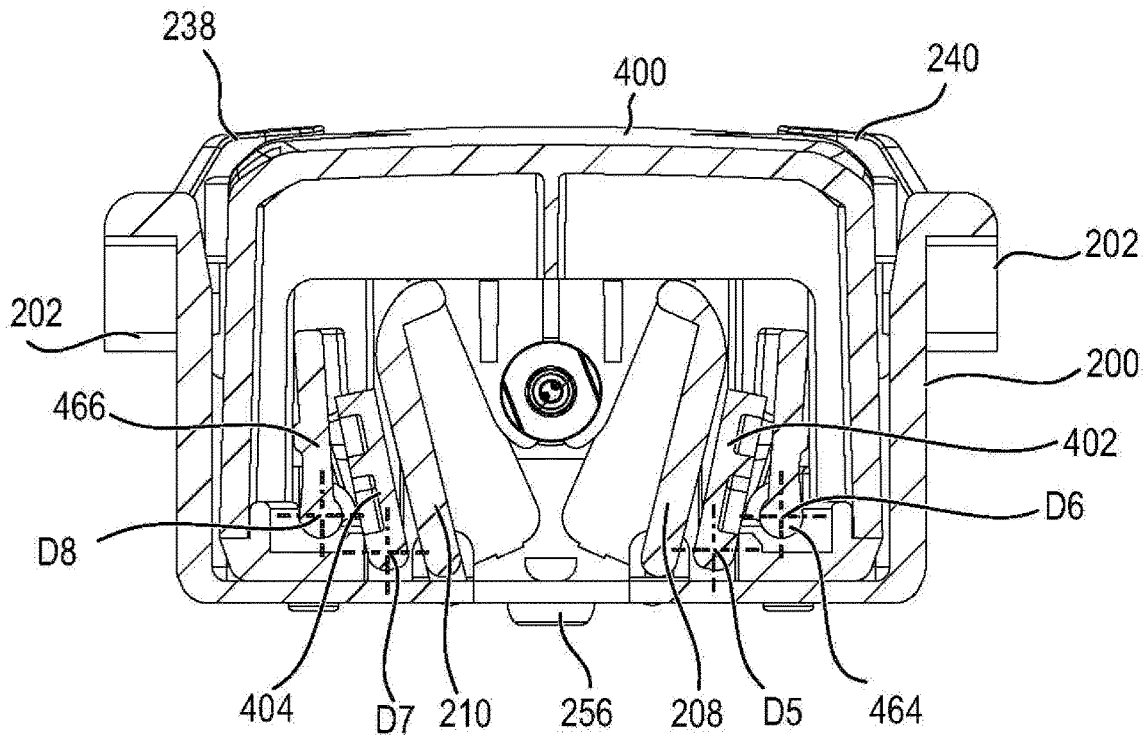
FIG. 33 shows a sectional illustration of the arrangement according to FIG. 30 along the sectional line K-K.

In FIG. 29, the guiding flap 466 and the sterile flap 404 are illustrated in their open position, in which the guiding and locking webs 479 to 489 project partially from the guiding ad locking grooves 478 to 488 by way of the relative movement in the arrow direction P8.

FIG. 30 shows a partial sectional illustration of an arrangement with a sterile lock 200 and a sterile unit 400 connected to the sterile lock 200. FIG. 31 shows a sectional illustration of the arrangement according to FIG. 30 along the sectional line I-I, FIG. 32 a sectional illustration of the arrangement according to FIG. 30 along the sectional line J-J, FIG. 33 a sectional illustration of the arrangement according to FIG. 30 along the sectional line K-K and FIG. 34 a sectional illustration of the arrangement according to FIG. 30 along the sectional line L-L. As can be seen in FIG. 31, the sterile unit 400 has an RFID transponder 494 in which preferably at least one unambiguous identification of the sterile unit 400 and preferably information about the surgical instrument 500 coupled with the sterile unit 400 are stored. In addition, further information such as information on the manufacturer of the sterile unit 400, batch information, durability information, can be stored preferably in an area of the RFID transponder 494 that cannot be overwritten. In a memory area of the RFID transponder 494 that can preferably be written only once information on the first use of the sterile unit 400, in particular the point in time of the first use and/or an unambiguous surgery identification of the surgery in which the first use of the sterile unit 400 took place can be stored, so that by way of this information it can be prevented that the sterile unit 400 is used in a further surgery, in particular in a further patient. The identification of the RFID transponder 494 and/or the information stored in the RFID transponder 494 can be read by means of the RFID read and write unit 121 of the coupling unit 100 and if necessary information in the form of data can be stored in the RFID transponder 494.

FIG. 32 shows that in the case of a connection of the sterile unit 400 to the sterile lock 200 both the lock flaps 208, 210 and the guiding flaps 464, 466 and the sterile flaps 402, 404 are open so that the second transmitting means 406 of the sterile unit 400 can be brought into direct contact with the first transmitting means 102 through the flaps 208, 210, 402, 404, 464, 466. In particular, both a direct electrical connection between the electrical contact elements 106, 108 of the coupling unit 100 and the electrical contact elements 422, 423 of the sterile unit 400 can be established and a direct engagement of the mechanical transmitting means 110 to 116 of the coupling unit 100 with the transmitting elements 408 to 414 of the sterile unit 400 can be accomplished. Thus, no additional electrical and/or mechanical transmitting elements between the coupling unit 100 and the sterile unit 400 are required. This is both more cost-efficient and less susceptible to failure than the provision of additional transmitting elements, in particular mechanical transmitting elements, between the coupling unit 100 and the sterile unit 400, as for example used in the prior art.

As can be well seen in FIG. 32, the sterile flaps 208, 210 have been pushed apart by means of the V-shaped elements 456 to 462 up into their position shown in FIG. 32, after they have been pushed apart by means of the cams 415, 417 already so far that the V-shaped elements 456 to 462 engage with the opening gap created in this way and the push the lock flaps 208, 210 as well as the sterile flaps 402, 404 together with the guiding flaps 464, 466 each time in their open position.

In the open state, the sterile outside of the sterile flap 402 and the sterile outside of the lock flap 208 are arranged opposite to each other. In the same way, the sterile outside of the sterile flap 404 and the sterile outside of the lock flap 210 are arranged opposite to each other so that even in the case of a direct contact of the sterile flap 402 with the lock flap 208 and a direct contact of the sterile flap 404 with the lock flap 210, respectively, neither a contamination of the lock flaps 208, 210 nor a contamination of the sterile flaps 402, 404 takes place.

Thus, only sterile non-contaminated areas of the sterile lock 200 come into contact with sterile non-contaminated areas of the sterile unit 400 so that after a separation of the sterile unit 400 from the sterile lock 200 there is no risk of a contamination of the sterile area 39.

Figure 34:
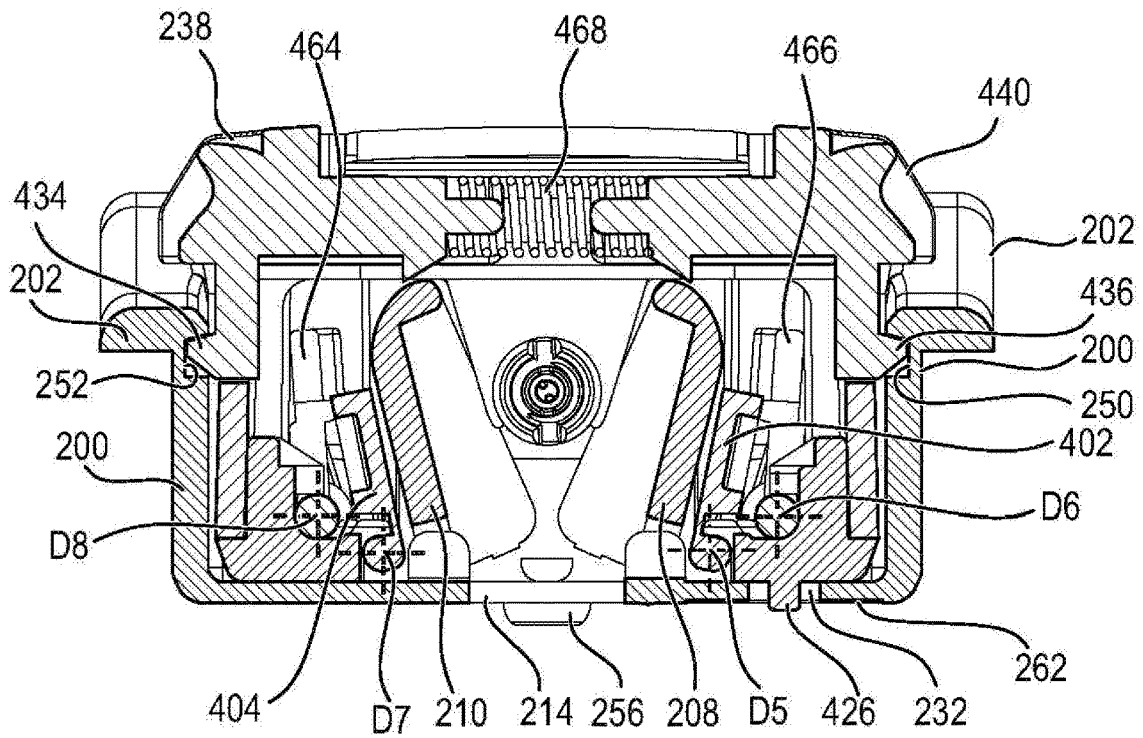
FIG. 34 shows a sectional illustration of the arrangement according to FIG. 30 along the sectional line L-L.

In FIG. 34 it is shown how the snap-in elements 434, 436 of the sterile unit 400 engage with the snap-in beads 250, 252 of the sterile lock 200 when the sterile unit 400 is correctly connected to the sterile lock 200. Further, it can be seen in FIG. 34 how the detection element 426 projects through the first detection window 232, the detection element 426 projecting into the recess of the first sensor 118 of the coupling unit 100 when the sterile lock 200 is connected to the coupling unit 100 so that the sensor detects the detection element 426. Further, in FIG. 34, the foil 162 is illustrated which is elastically and/or plastically deformed by the detection element 426 and thus covers the detection element 426 in a sterile manner.

Figure 35:
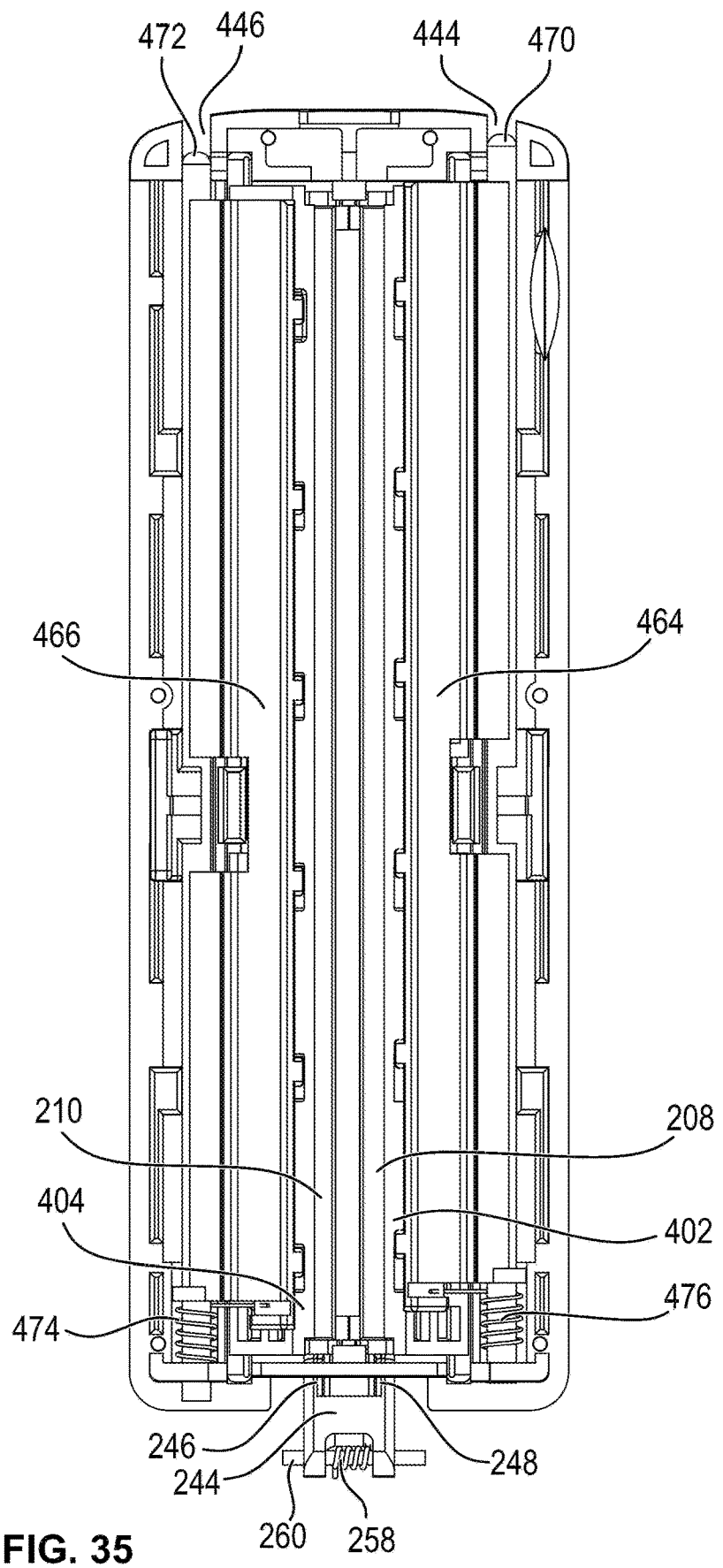
FIG. 35 shows elements of a sterile flap system of the sterile unit and of a lock flap system of the sterile lock of the arrangement according to FIGS. 30 to 34.

FIG. 35 shows elements of the sterile flap system with the sterile flaps 402, 404 and the guiding flaps 464, 466 and elements of the lock flap system of the sterile lock 200 with the lock flaps 208, 210. As already explained, the tines 246, 248 of the guiding fork 244 engage with the guiding beads 240, 242 in the closed state of the lock flaps 208, 210 so that via this engagement there is a positive connection which prevents that the lock flaps 208, 210 are pushed open. In the position of the guiding fork 244 shown in FIG. 35, its tines 246, 248 are no longer engaged with the guiding beads 240, 242 of the lock flaps 208, 210 so that these can be opened further by the V-shaped engaging elements 456 to 462 of the sterile unit 400. In FIG. 35, the lock flaps 208, 210 and the guiding flaps 464, 466 as well as the sterile flaps 202, 204 are illustrated in a position before the lock flaps 208, 210 are opened further by means of the V-shaped engaging elements 456 to 462. In doing so, both the lock flaps 208, 210 and the guiding flaps 464, 466 and the sterile flaps 402, 404 are opened further up to the position shown in FIGS. 33, 34. In order to illustrate the differences between the locked position and the unlocked position of the unlocking pins 470, 472, the locking pin 470 is illustrated in its locked position and the unlocking pin 472 is illustrated in its unlocked position in FIG. 35. Here, it has to be taken into account that the guiding flap 464 and the sterile flap 402, despite the arrangement of the unlocking pin 470 in the locked position, have been pivoted about their axes of rotation D5, D6 up to the partially open position shown in FIG. 35, although this would not be possible in case of an actual locking.

In FIG. 36, a side view of the arrangement according to FIGS. 30 to 35 is shown and in FIG. 37 a sectional illustration of a portion of the arrangement according to FIG. 36 along the sectional line M-M is shown. In FIG. 38, a sectional illustration of the arrangement according to FIG. 36 along the sectional line N-N is shown.

Figure 39:
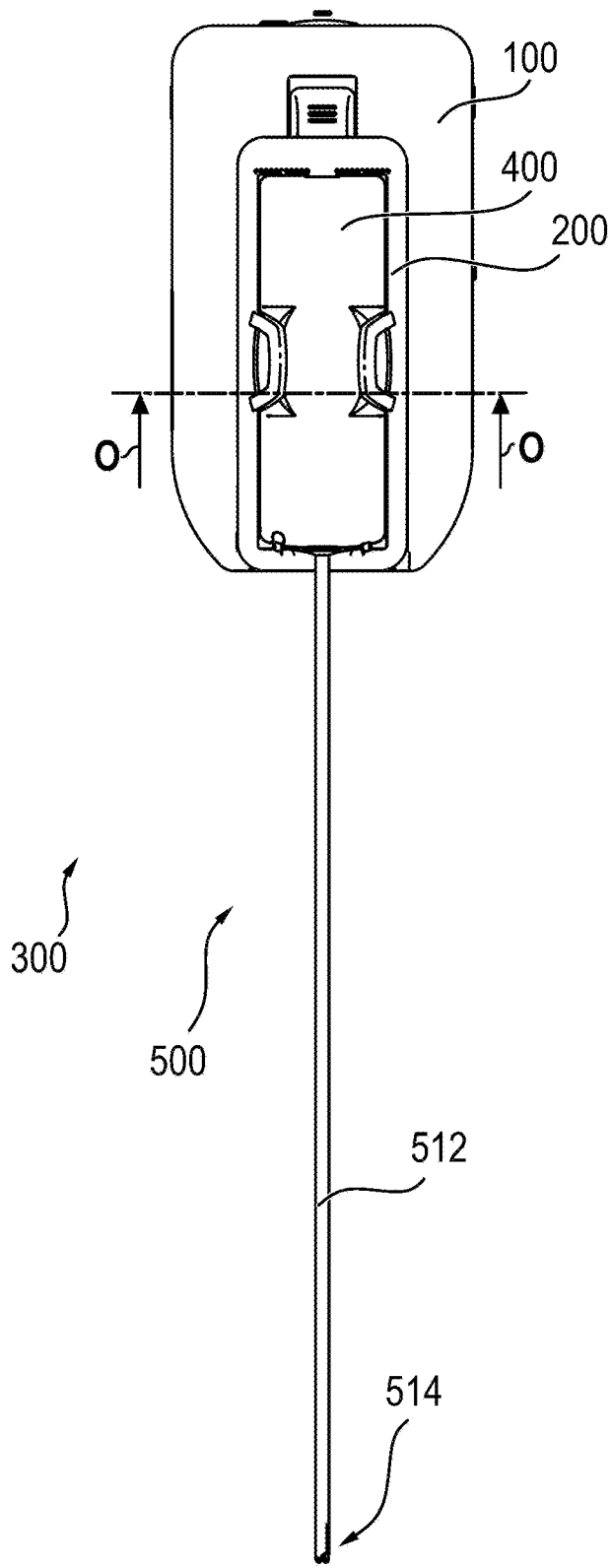
FIG. 39 shows a top view of an arrangement of the coupling unit, sterile lock and instrument unit.
Figure 40:
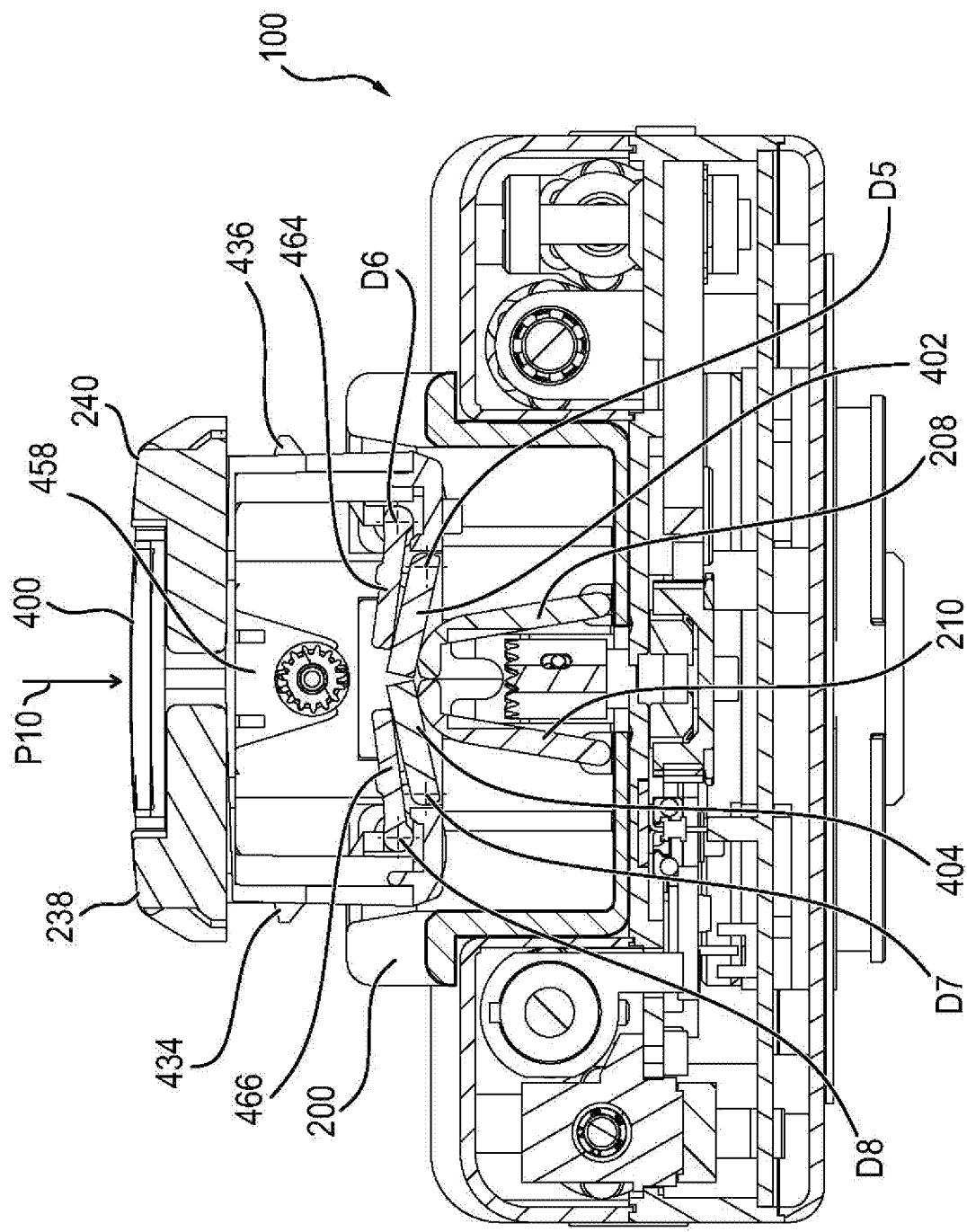
FIG. 40 shows a sectional illustration of the arrangement according to FIG. 39 along the sectional line O-O in a first position for connecting the instrument unit to the sterile lock coupled to the coupling unit.
Figure 41:
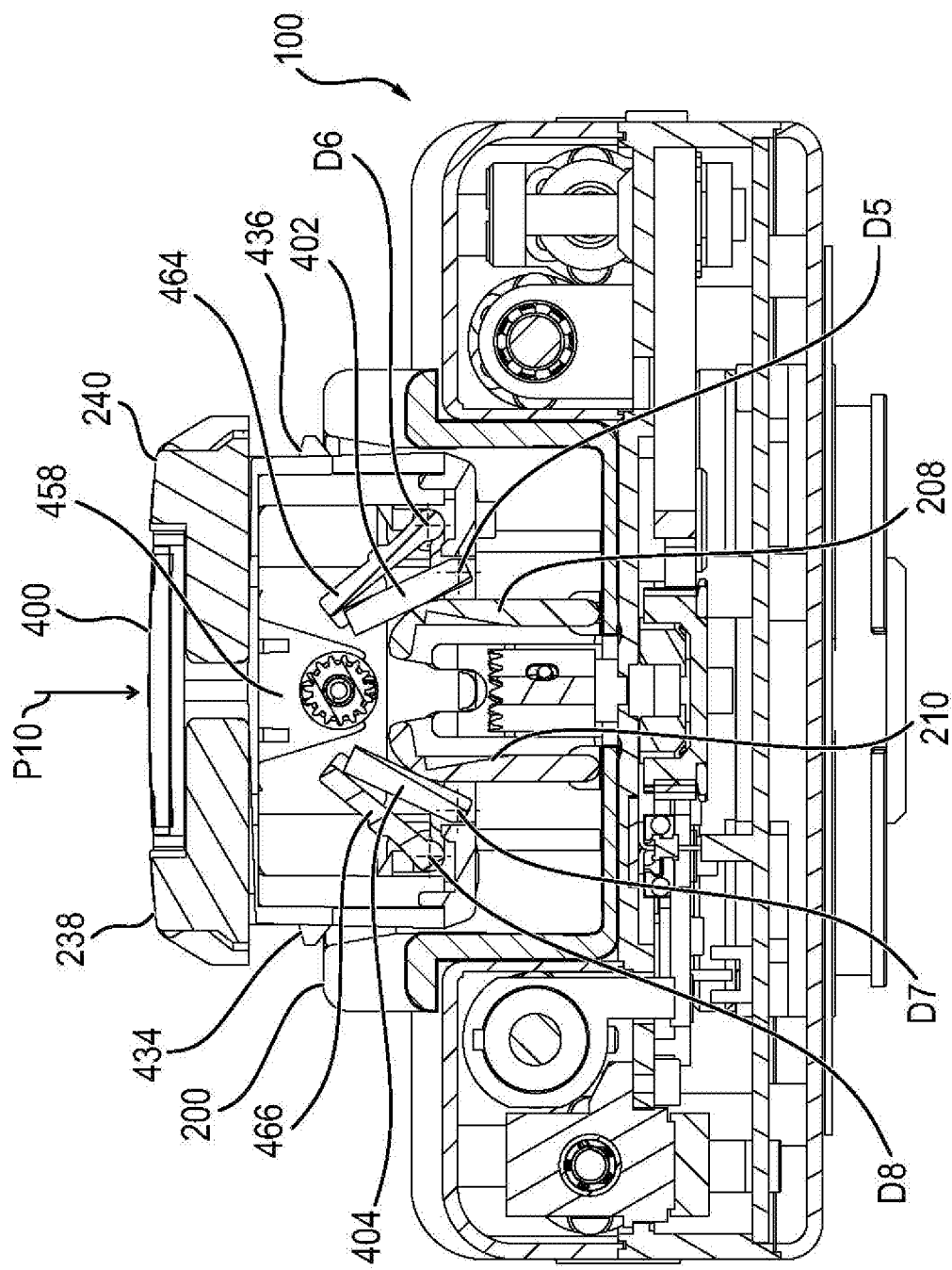
FIG. 41 shows a sectional illustration of the arrangement according to FIG. 39 along the sectional line O-O in a second position for connecting the instrument unit to the sterile lock coupled to the coupling unit.
Figure 42:
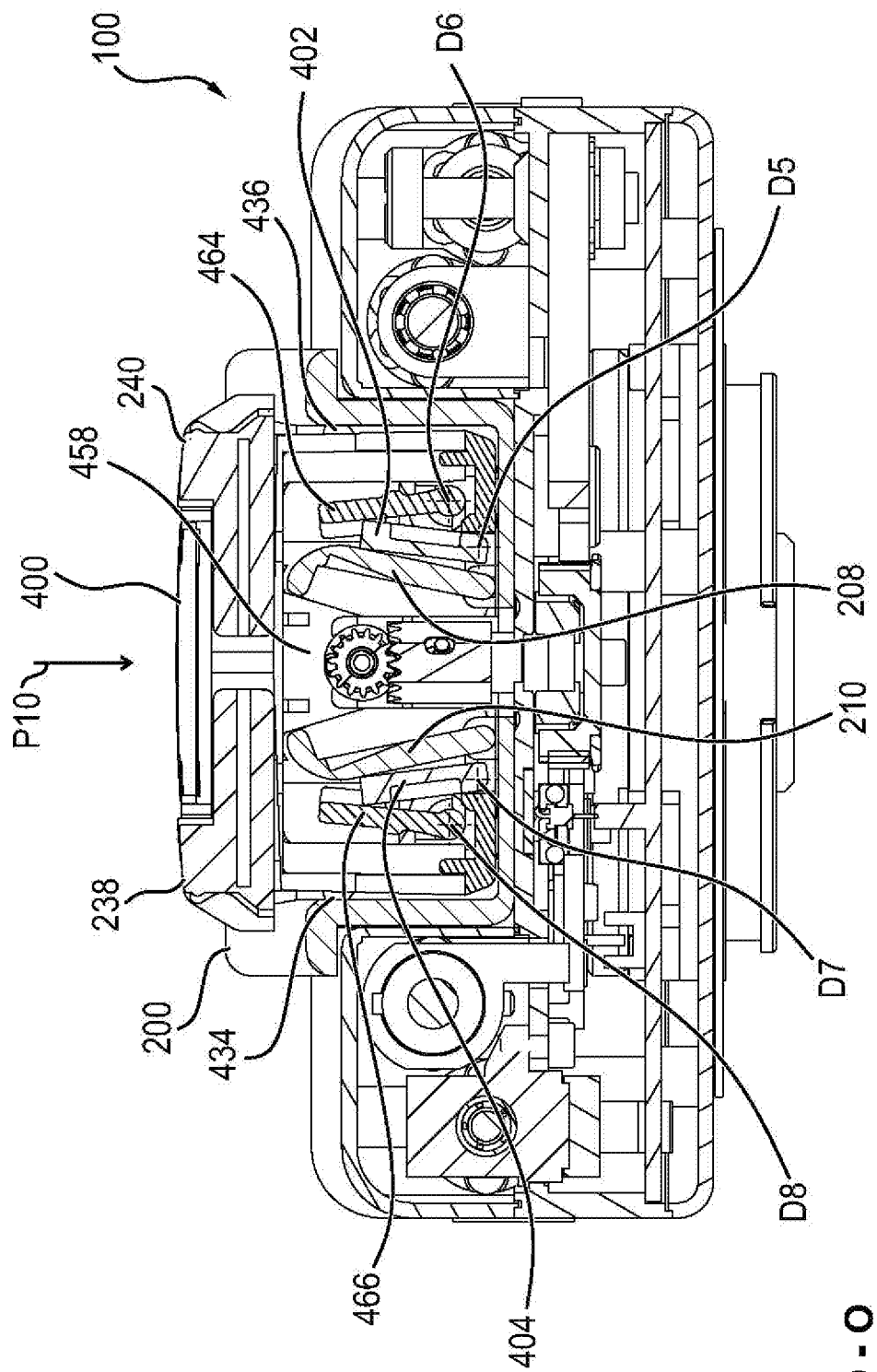
FIG. 42 shows a sectional illustration of the arrangement according to FIG. 39 along the sectional line O-O in a third position for connecting the instrument unit to the sterile lock coupled to the coupling unit.

FIG. 39 shows a top view of an arrangement with the coupling unit 100, the sterile lock 200 and the instrument unit 300 comprising the sterile unit 400 and the sterile surgical instrument 500. FIG. 40 shows a sectional illustration of the arrangement according to FIG. 39 along the sectional line O-O in a first position immediately before connecting the sterile unit 400 of the instrument unit 300 to the sterile lock 200 already coupled to the coupling unit 100. FIG. 41 shows a sectional illustration of the arrangement according to FIG. 39 along the sectional line O-O in a second position for connecting the sterile unit 400 of the instrument unit 300 to the sterile lock 200 already coupled to the coupling unit 100. FIG. 42 shows a sectional illustration of the arrangement according to FIG. 39 along the sectional line O-O in a third position in which the sterile unit 400 of the instrument unit 300 is connected to the sterile lock 200 coupled to the coupling unit 100 so that the first transmitting means 102 of the coupling unit 100 are engaged with the transmitting elements of the second transmitting means 406 for direct coupling.

In the position shown in FIG. 40, the guiding flaps 464, 466 have been moved by the insertion of the guiding and unlocking webs 228, 230 into the grooves 444, 446 and thus have already been moved along their axis of rotation D6, D8 in the direction of the arrows P4, P5 from their locked position into their unlocked position so that the sterile flaps 402, 404 together with the guiding flaps 464, 466 have been pushed open by a movement of the sterile unit 400 in the direction of the arrow P10 and the contact of the sterile flaps 402, 404 with the lock flaps 208, 210 caused thereby. As a result, the sterile unit 400 gets deeper into the receiving area of the sterile lock 200 provided for receiving the sterile unit 400 so that the actuating web 454 comes into engagement with the guiding fork 244 and pivots the same against the spring force of the guiding fork spring 258. As a result, the tines 246, 248 of the guiding fork 244 are engaged with the guiding beads 240, 242 such that the lock flaps 208, 210 can be pushed apart by the cams 415, 417 and thus be opened. When the sterile unit 400 is further moved in the direction of the arrow P10, the V-shaped engaging elements 458 to 462 come into engagement with the lock flaps 208, 210 and push these and the sterile flaps 402, 404 together with the guiding flaps 464, 466 further outward into their fully open position shown in FIG. 42. By the contact of the lock flaps 208, 210 with the sterile flaps 402, 404, these are opened further together with the guiding flaps 464, 466 until all flaps 208, 210, 402, 404, 464, 466 are arranged in the open position shown in FIG. 42.

In the case of a reversed movement of the sterile unit 400, when the sterile unit 400 is removed from the sterile lock 200, i.e. from the position shown in FIG. 42 into the position shown in FIG. 40 opposite to the direction of the arrow P10, a reversed sequence of motion of the sterile, guiding and lock flaps takes place so that these flaps are in particular closed by the spring force of the springs 474, 476 and the tines 246, 248 of the guiding fork 244 are again engaged with the guiding beads 240, 242 and completely close the lock flaps 208, 210. By the positive connection between the fork tines 246, 248 and the guiding beads 240, 244 caused in this way, the lock flaps 208, 210 are reliably held in their closed position so that the lock flaps 208, 210 cannot be opened from outside. Further, the guiding flaps 464, 466 are completely closed and moved into their locked position by means of the springs 474, 476 when the sterile unit 400 is removed from the sterile lock 200 so that afterwards these cannot be opened even when an external force is applied on the sterile flaps 402, 404.

Figure 43:
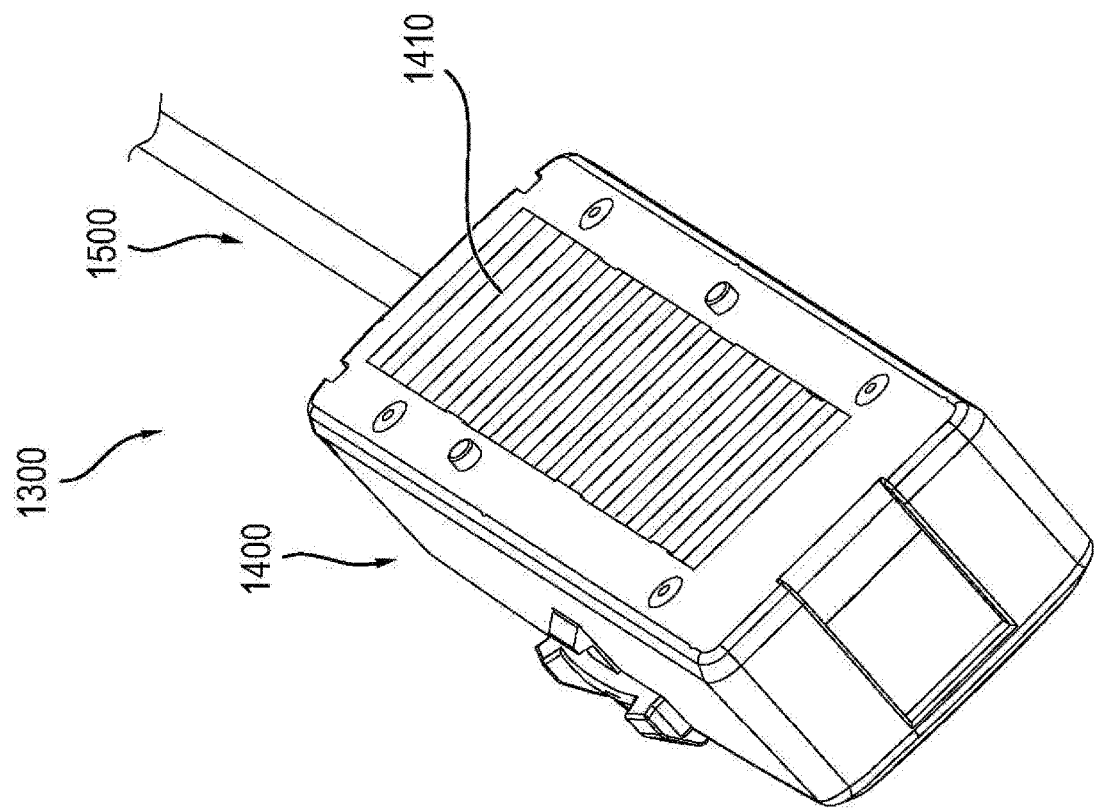
FIG. 43 shows a detail of an instrument unit according to a second embodiment.

FIG. 43 shows a detail of an instrument unit 1300 with a sterile unit 1400 and a surgical instrument 1500 according to a second embodiment. In contrast to the instrument unit 300, the sterile unit 1400 of the instrument unit 1300 has no sterile flaps but a jalousie 1410 for covering the driven elements in a sterile manner. The further structure and the function of the instrument unit 1300 corresponds to the structure and the function of the instrument unit 300 according to FIGS. 1 to 42.

Figure 44:
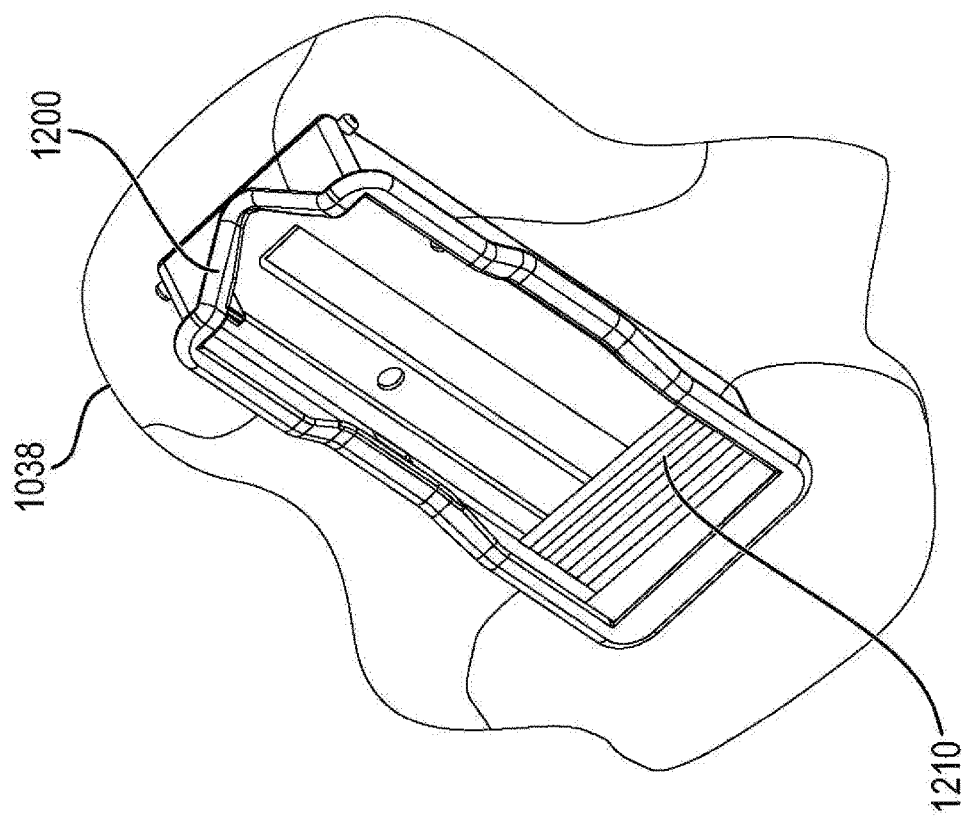
FIG. 44 shows a sterile cover with a sterile lock according to a second embodiment.

FIG. 44 shows a detail of a sterile covering 1038 with a sterile lock 1200 which in contrast to the sterile lock 200 has no sterile flaps but a jalousie 1210 for shielding drive elements of the coupling unit 100 in a sterile manner. The jalousie 1410 of the coupling unit 1400 and the jalousie 1210 of the sterile lock 1200 are opened in a suitable manner by a mechanical engagement when connecting the sterile unit 1400 to the sterile lock 1200 or the sterile unit 1400 to the sterile lock 200 or the sterile unit 400 to the sterile lock 1200, respectively. Alternatively, active drive elements, such as one electric motor each, for opening and closing the respective jalousie 1410, 1210 can be provided.

Figure 45:
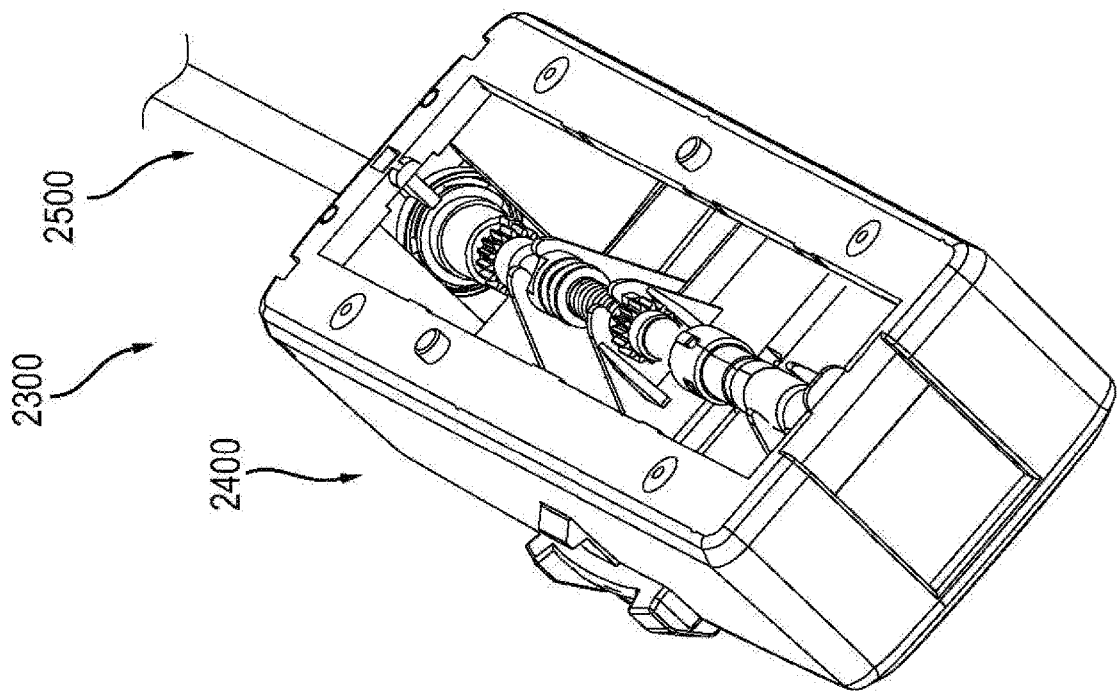
FIG. 45 shows a detail of an instrument unit according to a third embodiment.

In FIG. 45, a detail of an instrument unit 2300 with a sterile unit 2400 according to a third embodiment is shown. The sterile unit 2400 has no elements for covering the driven elements in a sterile manner so that this instrument unit 2400 is immediately removed from the sterile area 39 after separation from the sterile lock 200, 1200 or after separation from a further sterile lock 2200 shown in FIG. 46.

Figure 46:
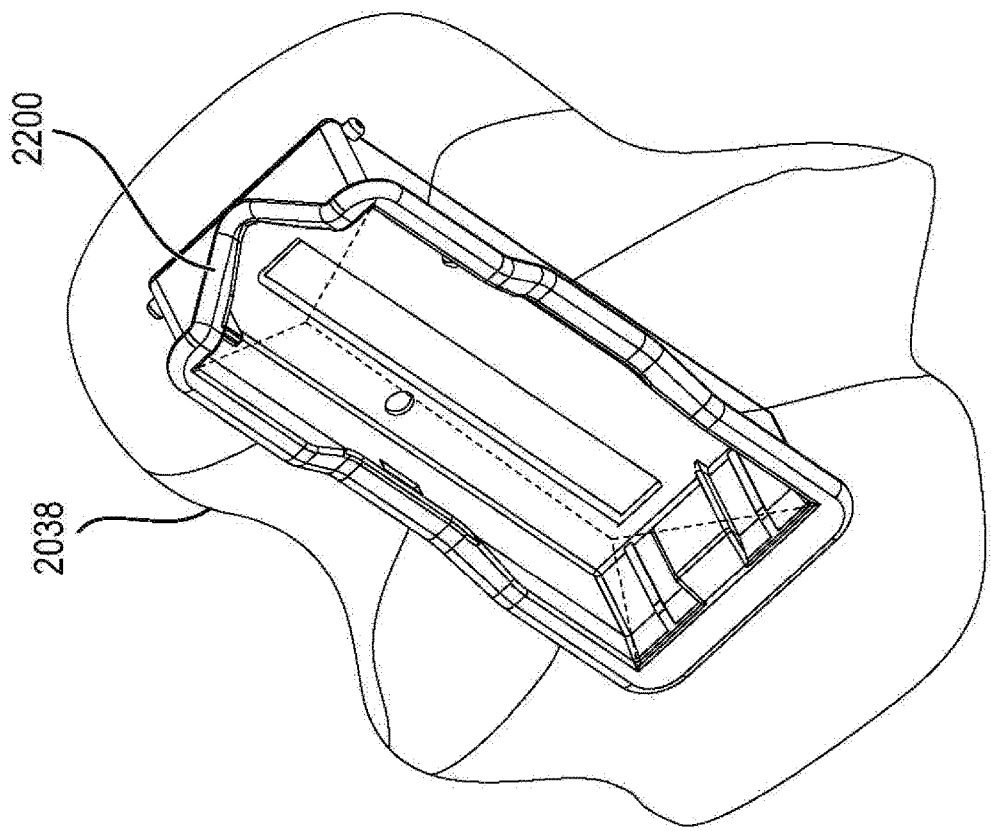
FIG. 46 shows a sterile cover with a sterile lock according to a third embodiment.

The sterile cover 2038 shown in FIG. 46 comprises a sterile lock 2200 which is couplable to the coupling unit 100 just like the sterile unit 200. In contrast to the sterile lock 200, the sterile lock 2200 has no lock flaps but comprises a foil provided with predetermined breaking points indicated by means of dotted lines, which foil is torn open along the predetermined breaking points when connecting a sterile unit 400, 1400, 2400 to the sterile lock 2200 so that a direct coupling of the drive elements 110 to 116 of the coupling unit 100 with the driven elements 408 to 414 is easily possible. Preferably, when using the sterile lock 2200, the sterile unit 400, 1400, 2400 is not separated during a surgery but only after the surgery has been terminated.

The invention claimed is:

1. A device for robot-assisted surgery comprising:
   at least one non-sterile manipulator arm having a coupling unit which has at least one first transmitting means,
   at least one sterile unit arranged in a sterile area and having at least one second transmitting means,
   a sterile cover for shielding at least a part of the non-sterile manipulator arm from the sterile area,
   wherein the sterile cover comprises a sterile lock with which the coupling unit and the sterile unit are each connectable, the sterile lock having at least one lock flap movable relative to the sterile lock between an open state uncovering an opening in the sterile lock and a closed state covering the opening in the sterile lock and lock and shielding the first transmitting means in a sterile manner,
   so that as the sterile unit is connected to the sterile lock the at least one lock flap moves from the closed state into the open state allowing a direct transmission between the first transmitting means and the second transmitting means through the opening, and
   as the sterile unit is separated from the sterile lock the at least one lock flap moves from the open state into the closed state wherein the lock flap shields the first transmitting means from the sterile area.

2. The device according to claim 1, characterized in that the sterile unit has at least one sterile flap which in a closed state shields the second transmitting means in a sterile manner; so that when connecting the sterile unit to the sterile lock each time a movement of the lock flap and of the sterile flap from the closed state into the open state takes place, a direct transmission between the first transmitting means and the second transmitting means through an opening uncovered by the lock flap and the sterile flap in the open state is possible; and so that when separating the sterile unit from the sterile lock, a movement of the lock flap and of the sterile flap each time from the open state into the closed state takes place after separation, the lock flap shields the first transmitting means from the sterile area and the sterile flap shields the second transmitting means from the sterile area.

3. The device according to claim 1, characterized in that the first transmitting means of the coupling unit comprises at least one of at least one drive element, at least one first electrical transmitting element interface, or at least one optical transmitting element,
   the second transmitting means of the sterile unit comprises at least one of at least one driven element, at least one electrical contact), or at least one optical transmitting element, and
   the sterile lock is connectable to the coupling unit and the sterile unit such that at least one of the at least one drive element is directly engaged with the at least one driven element, the first transmitting means is coupled with the electrical contact, or the optical transmitting element of the coupling unit is directly coupled with the optical transmitting element of the sterile unit.

4. The device according to claim 3 wherein the at least one optical transmitting element of the coupling unit and the at least one sterile unit form an optical interface between the coupling unit and the at least one sterile unit.

5. The device according to claim 1, characterized in that the coupling unit is arranged at a proximal end of the non-sterile manipulator arm,
   the sterile unit forms part of at least one of a surgical instrument, an endoscope, or a medical device, wherein the sterile unit is arranged at a distal end of at least one of the surgical instrument, the endoscope, or the medical device,
   the coupling unit is connectable to a first connecting area of the sterile lock,
   the sterile unit is connectable to a second connecting area of the sterile lock, and
   the first connecting area and the second connecting area are arranged on sides of the sterile lock facing away from each other.

6. The device according to claim 5, characterized in that the sterile outside of the sterile flap and the sterile outside of the lock flap are arranged opposite to each other when connecting the sterile unit to the second connecting area, when both the sterile flap and the lock flap are open, wherein the sterile outsides of the sterile flap and the lock flap face each other in the open state.

7. The device according to claim 1, characterized in that the first connecting area of the sterile lock is connectable to the coupling unit via a first releasable snap-in connection and the second connecting area of the sterile lock is connectable to the sterile unit via a second releasable snap-in connection.

8. The device according to claim 1, characterized in that the coupling unit comprises at least one coupling sensor which detects the presence of a sterile unit that is connected to the sterile lock,
the device has a control unit which only allows a transmission between the first transmitting means and the second transmitting means when a sterile unit that is connected to the sterile lock has been detected by means of the coupling sensor.

9. The device according to claim 1, characterized in that the coupling unit has several drive elements as first transmitting means, the sterile unit has several driven elements, wherein the drive elements are engaged with the driven elements for a mechanical coupling of the coupling unit with the sterile unit when the sterile unit is coupled with the sterile lock and when the coupling unit is coupled with the sterile lock.

10. The device according to claim 1, characterized in that the lock flap separates the first connecting area from the second connecting area, automatically opens when connecting the sterile unit to the second connecting area, and automatically closes when separating the sterile unit from the second connecting area.

11. The device according to claim 10, characterized in that the lock flap is automatically unlocked when connecting the sterile unit to the second connecting area and is automatically locked when separating the sterile unit from the second connecting area.

12. The device according to claim 1, characterized in that the sterile unit has at least one sterile flap which covers the at least one second transmitting means, automatically opens when connecting the sterile unit to the second connecting area, and automatically closes when separating the sterile unit from the second connecting area.

13. The device according to claim 12, characterized in that the sterile flap is automatically unlocked when connecting the sterile unit to the second connecting area and is automatically locked when separating the sterile unit from the second connecting area.

14. An arrangement for robot-assisted surgery, comprising:
at least one device according to claim 1,
at least one display unit which outputs at least one image of the operating area in real time,
at least one input device for the input of at least one input command, and
a control unit which positions the non-sterile manipulator arm and the sterile unit connected via the sterile lock to the coupling unit of the non-sterile manipulator arm dependent on the input command by means of at least one drive unit.

15. The device according to claim 1 wherein the coupling unit has at least one electrical contact as the first transmitting means and the sterile unit has at least one complementary electrical contact as the second transmitting means, wherein the at least one electrical contact of the coupling unit and the at least one complimentary electrical contact of the sterile unit establish an electrical connection between the coupling unit and the sterile unit for transmitting at least high-frequency electrical energy when the coupling unit is coupled with the sterile lock and when the sterile unit is coupled with the sterile lock.

16. A sterile lock comprising:
a first connecting area for connecting the sterile lock to a non-sterile coupling unit,
a second connecting area for connecting the sterile lock to a sterile unit arranged in a sterile area,
a circumferential third connecting area for connecting the sterile lock to a flexible sterile cover for shielding the sterile area from the non-sterile elements,
wherein the sterile lock has at least one lock flap, movable relative to the sterile lock between a closed state and an open state,
that in the closed state closes an opening between the first connecting area and the second connecting area in a sterile manner, and
that in the open state uncovers the opening between the first connecting area and the second connecting area.

17. The sterile lock according to claim 16, configured so that as the sterile lock is connected to the coupling unit, the lock flap moves from the closed state into the open state allowing a direct transmission between a first transmitting means of the coupling unit and a second transmitting means of the sterile unit through the opening, and
as the sterile unit is separated from the sterile lock the lock flap moves from the open state into the closed state shielding the first transmitting means from the sterile area, and is locked in the closed state.

18. A method for robot-assisted surgery in which a non-sterile manipulator arm is shielded from a sterile area by means of a sterile cover and a sterile lock integrated in the cover, characterized in that a non-sterile coupling unit of the non-sterile manipulator arm is connected to a first connecting area of the sterile lock so that in a closed state a lock flap of the sterile lock closes an opening to at least one first transmitting means arranged in the coupling unit in a sterile manner,
a sterile unit arranged in the sterile area is connected to a second connecting area of the sterile lock, wherein the lock flap is automatically opened, wherein the opening connects the first connecting area to the second connecting area so that a transmission between the first transmitting means of the coupling unit and a second transmitting means of the sterile unit is possible, and
the sterile unit is separated from the second connecting area, wherein the lock flap is automatically closed and closes the opening in a sterile manner.

19. The method according to claim 18, characterized in that the sterile unit has at least one sterile flap; that the second transmitting means is shielded by the sterile flap in its closed state in a sterile manner; that the lock flap and the sterile flap are each moved from the closed state into the open state when connecting the sterile unit to the sterile lock so that a direct transmission between the first transmitting means and the second transmitting means through an opening uncovered by the lock flap and the sterile flap in the open state is possible, and that when separating the sterile unit from the sterile lock, the lock flap and the sterile flap are each moved from the open state into the closed state so that after the separation the first transmitting means is shielded from the sterile area by means of the lock flap and the second transmitting means is shielded from the sterile area by means of the sterile flap.

* * * * *

UNITED STATES PATENT AND TRADEMARK OFFICE
CERTIFICATE OF CORRECTION

PATENT NO. : 11,103,321 B2  
APPLICATION NO. : 15/527139  
DATED : August 31, 2021  
INVENTOR(S) : Braun et al.

Page 1 of 1

It is certified that error appears in the above-identified patent and that said Letters Patent is hereby corrected as shown below:

In the Claims

At Column 27, Lines 62-66, Claim 1 reads:
"...the sterile lock having at least one lock flap movable relative to the sterile lock between an open state uncovering an opening in the sterile lock and a closed state covering the opening in the sterile lock and lock and shielding the first transmitting means in a sterile manner,"
And should read:
"...the sterile lock having at least one lock flap movable relative to the sterile lock between an open state uncovering an opening in the sterile lock and a closed state covering the opening in the sterile lock and shielding the first transmitting means in a sterile manner,"

Signed and Sealed this  
Fourteenth Day of December, 2021

Drew Hirshfeld  
*Performing the Functions and Duties of the*  
*Under Secretary of Commerce for Intellectual Property and*  
*Director of the United States Patent and Trademark Office*